United States Patent
Gu et al.

(10) Patent No.: US 9,045,551 B2
(45) Date of Patent: Jun. 2, 2015

(54) ANTI-DLL4/VEGF DUAL VARIABLE DOMAIN IMMUNOGLOBULIN AND USES THEREOF

(71) Applicant: AbbVie Inc., North Chicago, IL (US)

(72) Inventors: Jijie Gu, Shrewsbury, MA (US); Dominic J. Ambrosi, Worcester, MA (US); Susan E. Lappe, Riverwoods, IL (US); Yingchun Li, Buffalo Grove, IL (US); Jonathan A. Hickson, Lake Villa, IL (US); Deanna L. Haasch, Grayslake, IL (US); Supriya Gupta, Sunnyvale, CA (US); Ravi Chari, Worcester, MA (US); Camellia Zamiri, Fremont, CA (US); Louie Naumovski, Los Altos, CA (US); Xianhua Cao, Hawthorn Woods, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 14/301,546

(22) Filed: Jun. 11, 2014

(65) Prior Publication Data

US 2014/0348835 A1  Nov. 27, 2014

Related U.S. Application Data

(62) Division of application No. 14/068,976, filed on Oct. 31, 2013.

(60) Provisional application No. 61/721,072, filed on Nov. 1, 2012, provisional application No. 61/787,927, filed on Mar. 15, 2013.

(51) Int. Cl.

| | |
|---|---|
| C07K 16/00 | (2006.01) |
| C12P 21/08 | (2006.01) |
| A61K 39/395 | (2006.01) |
| A61K 39/40 | (2006.01) |
| C07K 16/46 | (2006.01) |
| A61K 45/06 | (2006.01) |
| C07K 16/22 | (2006.01) |
| A61K 31/513 | (2006.01) |
| A61K 31/7068 | (2006.01) |
| A61K 31/337 | (2006.01) |
| A61K 31/4745 | (2006.01) |
| A61K 31/495 | (2006.01) |
| A61K 31/525 | (2006.01) |
| C07K 16/28 | (2006.01) |
| C07K 1/00 | (2006.01) |
| A61K 39/00 | (2006.01) |

(52) U.S. Cl.
CPC .......... C07K 16/468 (2013.01); A61K 45/06 (2013.01); C07K 16/22 (2013.01); A61K 2039/505 (2013.01); C07K 2317/76 (2013.01); C07K 2317/92 (2013.01); A61K 39/395 (2013.01); A61K 39/39591 (2013.01); C07K 2317/24 (2013.01); C07K 2317/31 (2013.01); C07K 2317/56 (2013.01); C07K 2317/94 (2013.01); A61K 31/513 (2013.01); A61K 31/7068 (2013.01); A61K 31/337 (2013.01); A61K 31/4745 (2013.01); A61K 31/495 (2013.01); A61K 31/525 (2013.01); A61K 39/3955 (2013.01); C07K 16/28 (2013.01); C07K 2317/565 (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,554,101 A | 11/1985 | Hopp |
| 4,699,784 A | 10/1987 | Shih et al. |
| 4,753,894 A | 6/1988 | Frankel et al. |
| 4,816,567 A | 3/1989 | Cabilly et al. |
| 4,943,533 A | 7/1990 | Mendelsohn et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,294,404 A | 3/1994 | Grandone et al. |

(Continued)

FOREIGN PATENT DOCUMENTS

| | | |
|---|---|---|
| CN | 1276428 A | 12/2000 |
| CN | 101058609 A | 10/2007 |

(Continued)

OTHER PUBLICATIONS

Marques et al., "Mediation of the Cytokine Network in the Implantation of Orthopedic Devices," Chapter 21, In *Biodegradable Systems in Tissue Engineering and Regenerative Medicine*, (Reis et al., eds.) (CRC Press LLC, Boca Raton, 2005) pp. 377-397.
"Adalimumab," in *The Merck Index*. 14th Ed., John Wiley & Sons, 2006; pp. 26-27.
"Cetuximab," in *The Merck Index*. 14th Ed., John Wiley & Sons, 2006; p. 335.
"Infliximab," in *The Merck Index*. 14th Ed., John Wiley & Sons, 2006; p. 863.
"Rituximab," in *The Merck Index*. 14th Ed., John Wiley & Sons, 2006; p. 1422.
"Trastuzumab," in *The Merck Index*. 14th Ed., John Wiley & Sons, 2006; p. 1646.
'T Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Alegre et al., "An Anti-Murine CD3 Monoclonal Antibody with a Low Affinity for Fcγ Receptors Suppresses Transplantation Responses While Minimizing Acute Toxicity and Immunogenicity," *J. Immunol.*, 155: 1544-1555 (1995).
Baslund et al., "Targeting interleukin-15 in patients with rheumatoid arthritis," *Arthritis Rheum.*, 52(9): 2686-2692 (2005).

(Continued)

*Primary Examiner* — Chun Dahle

(74) *Attorney, Agent, or Firm* — Finnegan, Henderson, Farabow, Garrett & Dunner, LLP

(57) ABSTRACT

Disclosed herein are multivalent and multispecific binding proteins, methods of making the binding proteins, and their uses in the diagnosis, monitoring, inhibition, prevention and/or treatment of cancers, tumors, and/or other angiogenesis-dependent diseases characterized by aberrant DLL4 and/or VEGF expression or activity.

11 Claims, 1 Drawing Sheet

(56) References Cited

U.S. PATENT DOCUMENTS

| | | |
|---|---|---|
| 5,403,484 A | 4/1995 | Ladner et al. |
| 5,427,908 A | 6/1995 | Dower et al. |
| 5,500,362 A | 3/1996 | Robinson et al. |
| 5,516,637 A | 5/1996 | Huang et al. |
| 5,530,101 A | 6/1996 | Queen et al. |
| 5,558,864 A | 9/1996 | Bendig et al. |
| 5,565,332 A | 10/1996 | Hoogenboom et al. |
| 5,565,352 A | 10/1996 | Hochstrasser et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,641,870 A | 6/1997 | Rinderknecht et al. |
| 5,648,260 A | 7/1997 | Winter et al. |
| 5,656,272 A | 8/1997 | Le et al. |
| 5,658,727 A | 8/1997 | Barbas et al. |
| 5,677,171 A | 10/1997 | Hudziak et al. |
| 5,679,377 A | 10/1997 | Bernstein et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman et al. |
| 5,733,743 A | 3/1998 | Johnson et al. |
| 5,736,137 A | 4/1998 | Anderson et al. |
| 5,763,192 A | 6/1998 | Kauffman et al. |
| 5,766,886 A | 6/1998 | Studnicka et al. |
| 5,776,456 A | 7/1998 | Anderson et al. |
| 5,780,225 A | 7/1998 | Wigler et al. |
| 5,789,554 A | 8/1998 | Leung et al. |
| 5,795,965 A | 8/1998 | Tsuchiya et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,846,765 A | 12/1998 | Matthews et al. |
| 5,849,500 A | 12/1998 | Breitling et al. |
| 5,855,913 A | 1/1999 | Hanes et al. |
| 5,863,765 A | 1/1999 | Berry et al. |
| 5,874,064 A | 2/1999 | Edwards et al. |
| 5,891,996 A | 4/1999 | Mateo de Acosta del Rio et al. |
| 5,912,015 A | 6/1999 | Bernstein et al. |
| 5,916,597 A | 6/1999 | Lee et al. |
| 5,916,771 A | 6/1999 | Hori et al. |
| 5,929,212 A | 7/1999 | Jolliffe et al. |
| 5,934,272 A | 8/1999 | Lloyd et al. |
| 5,939,598 A | 8/1999 | Kucherlapati et al. |
| 5,959,083 A | 9/1999 | Bosslet et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,588 A | 11/1999 | Breitling et al. |
| 5,985,615 A | 11/1999 | Jakobovits et al. |
| 5,989,463 A | 11/1999 | Tracy et al. |
| 5,989,830 A | 11/1999 | Davis et al. |
| 5,998,209 A | 12/1999 | Jokobovits et al. |
| 6,019,968 A | 2/2000 | Platz et al. |
| 6,054,297 A | 4/2000 | Carter et al. |
| 6,057,098 A | 5/2000 | Buechler et al. |
| 6,066,719 A | 5/2000 | Zapata |
| 6,075,181 A | 6/2000 | Kucherlapati et al. |
| 6,090,382 A | 7/2000 | Salfeld et al. |
| 6,091,001 A | 7/2000 | Jakobovits et al. |
| 6,114,598 A | 9/2000 | Kucherlapati et al. |
| 6,127,132 A | 10/2000 | Breitling et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,214,984 B1 | 4/2001 | Zapata |
| 6,235,883 B1 | 5/2001 | Jakobovits et al. |
| 6,239,259 B1 | 5/2001 | Davis et al. |
| 6,258,562 B1 | 7/2001 | Salfeld et al. |
| 6,350,861 B1 | 2/2002 | Co et al. |
| 6,387,627 B1 | 5/2002 | Breitling et al. |
| 6,491,916 B1 | 12/2002 | Bluestone et al. |
| 6,506,883 B2 | 1/2003 | Meteo de Acosta del Rio et al. |
| 6,509,015 B1 | 1/2003 | Salfeld et al. |
| 6,639,055 B1 | 10/2003 | Carter et al. |
| 6,660,843 B1 | 12/2003 | Feige et al. |
| 6,699,473 B2 | 3/2004 | Raisch et al. |
| 6,699,658 B1 | 3/2004 | Wittrup et al. |
| 6,730,483 B2 | 5/2004 | Breitling et al. |
| 6,818,392 B2 | 11/2004 | Lou et al. |
| 6,884,879 B1 | 4/2005 | Baca et al. |
| 6,914,128 B1 | 7/2005 | Salfeld et al. |
| 6,986,890 B1 | 1/2006 | Shitara et al. |
| 7,060,269 B1 | 6/2006 | Baca et al. |
| 7,060,808 B1 | 6/2006 | Goldstein et al. |
| 7,070,775 B2 | 7/2006 | Le et al. |
| 7,179,892 B2 | 2/2007 | Basi et al. |
| 7,202,343 B2 | 4/2007 | Gudas et al. |
| 7,247,301 B2 | 7/2007 | van de Winkel et al. |
| 7,247,304 B2 | 7/2007 | van de Winkel et al. |
| 7,258,857 B2 | 8/2007 | Stern et al. |
| 7,262,028 B2 | 8/2007 | Van Berkel et al. |
| 7,317,091 B2 | 1/2008 | Lazar et al. |
| 7,419,821 B2 | 9/2008 | Davis et al. |
| 7,429,486 B2 | 9/2008 | Van Berkel et al. |
| 7,438,911 B2 | 10/2008 | Shitara et al. |
| 7,446,175 B2 | 11/2008 | Gram et al. |
| 7,446,179 B2 | 11/2008 | Jensen et al. |
| 7,449,616 B2 | 11/2008 | Pons et al. |
| 7,491,516 B2 | 2/2009 | Collinson et al. |
| 7,528,236 B2 | 5/2009 | Fong et al. |
| 7,566,772 B2 | 7/2009 | Green et al. |
| 7,592,429 B2 | 9/2009 | Paszty et al. |
| 7,612,181 B2 | 11/2009 | Wu et al. |
| 7,682,833 B2 | 3/2010 | Miller et al. |
| 7,727,527 B2 | 6/2010 | Shelton |
| 7,790,858 B2 | 9/2010 | Presta |
| 7,863,419 B2 | 1/2011 | Taylor et al. |
| 7,928,205 B2 | 4/2011 | Dillon et al. |
| 8,258,268 B2 | 9/2012 | Wu et al. |
| 8,388,965 B2 | 3/2013 | Rao et al. |
| 8,389,237 B2 | 3/2013 | Skerry et al. |
| 8,586,714 B2 | 11/2013 | Ghayur et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 8,835,610 B2 | 9/2014 | Hsieh et al. |
| 8,858,941 B2 | 10/2014 | Gurney et al. |
| 2002/0004587 A1 | 1/2002 | Miller et al. |
| 2002/0127231 A1 | 9/2002 | Schneck et al. |
| 2002/0136719 A1 | 9/2002 | Shenoy et al. |
| 2002/0137134 A1 | 9/2002 | Gerngross |
| 2003/0039645 A1 | 2/2003 | Adair et al. |
| 2003/0091561 A1 | 5/2003 | van de Winkel et al. |
| 2003/0092059 A1 | 5/2003 | Salfeld et al. |
| 2003/0118583 A1 | 6/2003 | Emery et al. |
| 2003/0165496 A1 | 9/2003 | Basi et al. |
| 2003/0186374 A1 | 10/2003 | Hufton et al. |
| 2003/0206898 A1 | 11/2003 | Fischkoff et al. |
| 2003/0226155 A1 | 12/2003 | Sadeghi et al. |
| 2004/0018577 A1 | 1/2004 | Emerson Campbell et al. |
| 2004/0018590 A1 | 1/2004 | Gerngross et al. |
| 2004/0038339 A1 | 2/2004 | Kufer et al. |
| 2004/0133357 A1 | 7/2004 | Zhong et al. |
| 2004/0162411 A1 | 8/2004 | Lanzavecchia |
| 2004/0219144 A1 | 11/2004 | Shelton |
| 2004/0237124 A1 | 11/2004 | Pons et al. |
| 2004/0241745 A1 | 12/2004 | Honjo et al. |
| 2005/0026881 A1 | 2/2005 | Robinson et al. |
| 2005/0038231 A1 | 2/2005 | Fahrner et al. |
| 2005/0042664 A1 | 2/2005 | Wu et al. |
| 2005/0095246 A1 | 5/2005 | Shafer |
| 2005/0118643 A1 | 6/2005 | Burgess et al. |
| 2005/0147610 A1 | 7/2005 | Ghayur et al. |
| 2005/0215769 A1 | 9/2005 | Breece et al. |
| 2005/0260204 A1 | 11/2005 | Allan |
| 2006/0002923 A1 | 1/2006 | Uede et al. |
| 2006/0024300 A1 | 2/2006 | Adams et al. |

(56) References Cited

U.S. PATENT DOCUMENTS

| | | |
|---|---|---|
| 2006/0041058 A1 | 2/2006 | Yin et al. |
| 2006/0067930 A1 | 3/2006 | Adams et al. |
| 2006/0078967 A1 | 4/2006 | Medlock et al. |
| 2006/0093599 A1 | 5/2006 | Gazit-Bornstein et al. |
| 2006/0104968 A1 | 5/2006 | Bookbinder et al. |
| 2006/0134105 A1 | 6/2006 | Lazar et al. |
| 2006/0160164 A1 | 7/2006 | Miller et al. |
| 2006/0233791 A1 | 10/2006 | Tedder et al. |
| 2006/0246071 A1 | 11/2006 | Green et al. |
| 2006/0253100 A1 | 11/2006 | Burright et al. |
| 2006/0280747 A1 | 12/2006 | Fuh et al. |
| 2007/0041905 A1 | 2/2007 | Hoffman et al. |
| 2007/0042458 A1 | 2/2007 | DeFrees et al. |
| 2007/0071675 A1 | 3/2007 | Wu et al. |
| 2007/0071745 A1 | 3/2007 | Umana et al. |
| 2007/0072225 A1 | 3/2007 | Alving |
| 2007/0092507 A1 | 4/2007 | Balthasar et al. |
| 2007/0092520 A1 | 4/2007 | Dennis et al. |
| 2007/0110747 A1 | 5/2007 | Paszty et al. |
| 2007/0123479 A1 | 5/2007 | Kufer et al. |
| 2007/0196376 A1 | 8/2007 | Raeber et al. |
| 2007/0232556 A1 | 10/2007 | Montine et al. |
| 2007/0286858 A1 | 12/2007 | Clancy et al. |
| 2007/0292420 A1 | 12/2007 | Giles-Komar et al. |
| 2008/0014196 A1 | 1/2008 | Yan |
| 2008/0015194 A1 | 1/2008 | Errico et al. |
| 2008/0038257 A1 | 2/2008 | Han et al. |
| 2008/0112888 A1 | 5/2008 | Wang |
| 2008/0118506 A1 | 5/2008 | An et al. |
| 2008/0118978 A1 | 5/2008 | Sato et al. |
| 2008/0171014 A1 | 7/2008 | Wu et al. |
| 2008/0175847 A1 | 7/2008 | Yan et al. |
| 2008/0187966 A1 | 8/2008 | Simmons |
| 2008/0193455 A1 | 8/2008 | Stassen et al. |
| 2008/0219971 A1 | 9/2008 | Smith et al. |
| 2008/0241163 A1 | 10/2008 | Burkly et al. |
| 2009/0028851 A1 | 1/2009 | Stuhmer et al. |
| 2009/0030308 A1 | 1/2009 | Bradford et al. |
| 2009/0035308 A1 | 2/2009 | Gill et al. |
| 2009/0042214 A1 | 2/2009 | Cooke et al. |
| 2009/0048122 A1 | 2/2009 | Glaser et al. |
| 2009/0053243 A1 | 2/2009 | Kurosawa et al. |
| 2009/0068195 A1 | 3/2009 | Vugmeyster et al. |
| 2009/0081234 A1 | 3/2009 | Heavner et al. |
| 2009/0148513 A1 | 6/2009 | Fraunhofer et al. |
| 2009/0155257 A1 | 6/2009 | Adams et al. |
| 2009/0155275 A1 | 6/2009 | Wu et al. |
| 2009/0191225 A1 | 7/2009 | Chang et al. |
| 2009/0208490 A1 | 8/2009 | Pavone et al. |
| 2009/0215992 A1 | 8/2009 | Wu et al. |
| 2009/0239259 A1 | 9/2009 | Hsieh |
| 2009/0259026 A1 | 10/2009 | Tomlinson et al. |
| 2009/0304693 A1 | 12/2009 | Ghayur et al. |
| 2009/0311253 A1 | 12/2009 | Ghayur et al. |
| 2010/0028340 A1 | 2/2010 | Mueller et al. |
| 2010/0040537 A1 | 2/2010 | Gu et al. |
| 2010/0047239 A1 | 2/2010 | Wu et al. |
| 2010/0056762 A1 | 3/2010 | Old |
| 2010/0074900 A1 | 3/2010 | Ghayur et al. |
| 2010/0076178 A1 | 3/2010 | Ghayur et al. |
| 2010/0104573 A1 | 4/2010 | Burkly et al. |
| 2010/0105569 A1 | 4/2010 | Hsieh et al. |
| 2010/0158901 A1 | 6/2010 | Tedder et al. |
| 2010/0190247 A1 | 7/2010 | Lazar et al. |
| 2010/0233079 A1 | 9/2010 | Jakob et al. |
| 2010/0260668 A1 | 10/2010 | Ghayur et al. |
| 2010/0266531 A1 | 10/2010 | Hsieh et al. |
| 2011/0008766 A1 | 1/2011 | Ghayur et al. |
| 2011/0044980 A1 | 2/2011 | Ghayur et al. |
| 2011/0091372 A1 | 4/2011 | Ghayur et al. |
| 2011/0091463 A1 | 4/2011 | Ghayur et al. |
| 2011/0117079 A1 | 5/2011 | Benatuil et al. |
| 2011/0142761 A1 | 6/2011 | Wu et al. |
| 2011/0150870 A1 | 6/2011 | Rader et al. |
| 2011/0189176 A1 | 8/2011 | Skokos |
| 2011/0212094 A1 | 9/2011 | Ghayur et al. |
| 2011/0217237 A1 | 9/2011 | Chen et al. |
| 2011/0229476 A1 | 9/2011 | Liu et al. |
| 2011/0263827 A1 | 10/2011 | Ghayur et al. |
| 2011/0318349 A1 | 12/2011 | Ghayur et al. |
| 2012/0014957 A1 | 1/2012 | Ghayur et al. |
| 2012/0034160 A1 | 2/2012 | Ghayur et al. |
| 2012/0087858 A1 | 4/2012 | Ghayur et al. |
| 2012/0258108 A1 | 10/2012 | Ghayur et al. |
| 2012/0263722 A1 | 10/2012 | Ghayur et al. |
| 2013/0004416 A1 | 1/2013 | Wu et al. |
| 2013/0171059 A1 | 7/2013 | Ghayur et al. |
| 2013/0171096 A1 | 7/2013 | Hsieh et al. |
| 2013/0195871 A1 | 8/2013 | Ghayur et al. |
| 2013/0236458 A1 | 9/2013 | Hsieh et al. |
| 2014/0093521 A1 | 4/2014 | Benatuil et al. |
| 2014/0134171 A1 | 5/2014 | Ghayur et al. |
| 2014/0134172 A1 | 5/2014 | Gu et al. |
| 2014/0213772 A1 | 7/2014 | Ghayur et al. |
| 2014/0219912 A1 | 8/2014 | Ghayur et al. |
| 2014/0234208 A1 | 8/2014 | Ghayur et al. |
| 2014/0271457 A1 | 9/2014 | Ghayur et al. |
| 2014/0271458 A1 | 9/2014 | Ghayur et al. |
| 2014/0308286 A1 | 10/2014 | Ghayur et al. |
| 2014/0356281 A1 | 12/2014 | Ghayur et al. |
| 2015/0017095 A1 | 1/2015 | Ghayur et al. |
| 2015/0017168 A1 | 1/2015 | Ghayur et al. |

FOREIGN PATENT DOCUMENTS

| | | |
|---|---|---|
| EP | 0 148 075 A | 7/1985 |
| EP | 0 517 024 A2 | 12/1992 |
| EP | 0 592 106 A1 | 4/1994 |
| EP | 0 239 400 B1 | 8/1994 |
| EP | 1 176 195 A1 | 1/2002 |
| EP | 1 454 917 A2 | 9/2004 |
| EP | 0 592 106 B1 | 11/2004 |
| EP | 0 519 596 B1 | 2/2005 |
| RU | 2 273 664 C2 | 4/2006 |
| WO | WO 89/06692 A1 | 7/1989 |
| WO | WO 90/02809 A1 | 3/1990 |
| WO | WO 90/05144 A1 | 5/1990 |
| WO | WO 90/05183 A1 | 5/1990 |
| WO | WO 90/14424 A1 | 11/1990 |
| WO | WO 90/14430 A1 | 11/1990 |
| WO | WO 90/14443 A1 | 11/1990 |
| WO | WO 91/05548 A1 | 5/1991 |
| WO | WO 91/09967 A1 | 7/1991 |
| WO | WO 91/10737 A1 | 7/1991 |
| WO | WO 91/10741 A1 | 7/1991 |
| WO | WO 91/17271 A1 | 11/1991 |
| WO | WO 91/18983 A1 | 12/1991 |
| WO | WO 92/01047 A1 | 1/1992 |
| WO | WO 92/02551 A1 | 2/1992 |
| WO | WO 92/03461 A1 | 3/1992 |
| WO | WO 92/09690 A2 | 6/1992 |
| WO | WO 92/11272 A1 | 7/1992 |
| WO | WO 92/15679 A1 | 9/1992 |
| WO | WO 92/16553 A1 | 10/1992 |
| WO | WO 92/18619 A1 | 10/1992 |
| WO | WO 92/19244 A2 | 11/1992 |
| WO | WO 92/20791 A1 | 11/1992 |
| WO | WO 92/22324 A1 | 12/1992 |
| WO | WO 92/22653 A1 | 12/1992 |
| WO | WO 93/01288 A1 | 1/1993 |
| WO | WO 93/06213 A1 | 4/1993 |
| WO | WO 93/11161 A1 | 6/1993 |
| WO | WO 93/11236 A1 | 6/1993 |
| WO | WO 94/02602 A1 | 2/1994 |
| WO | WO 94/11026 A1 | 5/1994 |
| WO | WO 94/18219 A1 | 8/1994 |
| WO | WO 95/01997 A1 | 1/1995 |
| WO | WO 95/09917 A1 | 4/1995 |
| WO | WO 95/14780 A2 | 6/1995 |
| WO | WO 95/15982 A2 | 6/1995 |
| WO | WO 95/16026 A1 | 6/1995 |
| WO | WO 95/20045 A1 | 7/1995 |
| WO | WO 95/20401 A1 | 8/1995 |
| WO | WO 95/24918 A1 | 9/1995 |

(56) References Cited

FOREIGN PATENT DOCUMENTS

| | | |
|---|---|---|
| WO | WO 95/25167 A1 | 9/1995 |
| WO | WO 96/20698 A2 | 7/1996 |
| WO | WO 96/33735 A1 | 10/1996 |
| WO | WO 96/34096 A1 | 10/1996 |
| WO | WO 96/40210 A1 | 12/1996 |
| WO | WO 97/20032 A1 | 6/1997 |
| WO | WO 97/29131 A1 | 8/1997 |
| WO | WO 97/32572 A2 | 9/1997 |
| WO | WO 97/44013 A1 | 11/1997 |
| WO | WO 98/16654 A1 | 4/1998 |
| WO | WO 98/24893 A2 | 6/1998 |
| WO | WO 98/31346 A1 | 7/1998 |
| WO | WO 98/31700 A1 | 7/1998 |
| WO | WO 98/45331 A2 | 10/1998 |
| WO | WO 98/50433 A2 | 11/1998 |
| WO | WO 99/06834 A2 | 2/1999 |
| WO | WO 99/15154 A1 | 4/1999 |
| WO | WO 99/20253 A1 | 4/1999 |
| WO | WO 99/23221 A2 | 5/1999 |
| WO | WO 99/45031 A2 | 9/1999 |
| WO | WO 99/53049 A1 | 10/1999 |
| WO | WO 99/54342 A1 | 10/1999 |
| WO | WO 99/57134 A1 | 11/1999 |
| WO | WO 99/66903 A2 | 12/1999 |
| WO | WO 00/09560 A2 | 2/2000 |
| WO | WO 00/37504 A2 | 6/2000 |
| WO | WO 00/56772 A1 | 9/2000 |
| WO | WO 00/78815 A1 | 12/2000 |
| WO | WO 01/00244 A2 | 1/2001 |
| WO | WO 01/32712 A2 | 5/2001 |
| WO | WO 01/58956 A2 | 8/2001 |
| WO | WO 01/62300 A2 | 8/2001 |
| WO | WO 01/62931 A2 | 8/2001 |
| WO | WO 01/71005 A2 | 9/2001 |
| WO | WO 01/77342 A1 | 10/2001 |
| WO | WO 01/83525 A2 | 11/2001 |
| WO | WO 01/88138 A1 | 11/2001 |
| WO | WO 02/02773 A2 | 1/2002 |
| WO | WO 02/02781 A1 | 1/2002 |
| WO | WO 02/12502 A2 | 2/2002 |
| WO | WO 02/16436 A2 | 2/2002 |
| WO | WO 02/053596 A2 | 7/2002 |
| WO | WO 02/072636 A2 | 9/2002 |
| WO | WO 02/097048 A2 | 12/2002 |
| WO | WO 03/016466 A2 | 2/2003 |
| WO | WO 03/035835 A2 | 5/2003 |
| WO | WO 03/039486 A2 | 5/2003 |
| WO | WO 03/068801 A2 | 8/2003 |
| WO | WO 03/086458 A1 | 10/2003 |
| WO | WO 03/089614 A2 | 10/2003 |
| WO | WO 03/100008 A2 | 12/2003 |
| WO | WO 03/102132 A2 | 12/2003 |
| WO | WO 2004/016286 A2 | 2/2004 |
| WO | WO 2004/024866 A2 | 3/2004 |
| WO | WO 2004/050683 A2 | 6/2004 |
| WO | WO 2004/058184 A2 | 7/2004 |
| WO | WO 2004/078140 A2 | 9/2004 |
| WO | WO 2005/016970 A2 | 2/2005 |
| WO | WO 2005/017107 A2 | 2/2005 |
| WO | WO 2005/044853 A2 | 5/2005 |
| WO | WO 2005/061540 A2 | 7/2005 |
| WO | WO 2005/061547 A2 | 7/2005 |
| WO | WO 2005/100584 A2 | 10/2005 |
| WO | WO 2005/118635 A2 | 12/2005 |
| WO | WO 2005/120557 A2 | 12/2005 |
| WO | WO 2006/001965 A2 | 1/2006 |
| WO | WO 2006/013107 A1 | 2/2006 |
| WO | WO 2006/015373 A2 | 2/2006 |
| WO | WO 2006/020258 A2 | 2/2006 |
| WO | WO 2006/024867 A2 | 3/2006 |
| WO | WO 2006/031370 A2 | 3/2006 |
| WO | WO 2006/044908 A2 | 4/2006 |
| WO | WO 2006/047350 A2 | 5/2006 |
| WO | WO 2006/066171 A1 | 6/2006 |
| WO | WO 2006/089133 A2 | 8/2006 |
| WO | WO 2006/099698 A2 | 9/2006 |
| WO | WO 2006/110883 A2 | 10/2006 |
| WO | WO 2006/116269 A2 | 11/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/131951 A2 | 12/2006 |
| WO | WO 2006/136159 A2 | 12/2006 |
| WO | WO 2007/005955 A2 | 1/2007 |
| WO | WO 2007/024715 A9 | 3/2007 |
| WO | WO 2007/042261 A2 | 4/2007 |
| WO | WO 2007/048849 A1 | 5/2007 |
| WO | WO 2007/053447 A2 | 5/2007 |
| WO | WO 2007/056470 A2 | 5/2007 |
| WO | WO 2007/059136 A2 | 5/2007 |
| WO | WO 2007/062037 A2 | 5/2007 |
| WO | WO 2007/062852 A2 | 6/2007 |
| WO | WO 2007/077028 A2 | 7/2007 |
| WO | WO 2007/117749 A2 | 10/2007 |
| WO | WO 2007/120651 A2 | 10/2007 |
| WO | WO 2007/120828 A1 | 10/2007 |
| WO | WO 2007/124299 A2 | 11/2007 |
| WO | WO 2007/143098 A2 | 12/2007 |
| WO | WO 2007/147901 A1 | 12/2007 |
| WO | WO 2008/011348 A2 | 1/2008 |
| WO | WO 2008/022152 A2 | 2/2008 |
| WO | WO 2008/024188 A2 | 2/2008 |
| WO | WO 2008/042236 A2 | 4/2008 |
| WO | WO 2008/057240 A2 | 5/2008 |
| WO | WO 2008/079326 A2 | 7/2008 |
| WO | WO 2008/100624 A2 | 8/2008 |
| WO | WO 2008/145338 A2 | 12/2008 |
| WO | WO 2008/150841 A1 | 12/2008 |
| WO | WO 2009/020654 A1 | 2/2009 |
| WO | WO 2009/052400 A1 | 4/2009 |
| WO | WO 2009/077993 A2 | 6/2009 |
| WO | WO 2009/089004 A1 | 7/2009 |
| WO | WO 2009/136382 A2 | 11/2009 |
| WO | WO 2009/155324 A2 | 12/2009 |
| WO | WO 2010/096434 A2 | 8/2010 |
| WO | WO 2010/102251 A2 | 9/2010 |
| WO | WO 2011/039370 A1 | 4/2011 |
| WO | WO 2011/084714 A2 | 7/2011 |
| WO | WO 2011/143562 A2 | 11/2011 |
| WO | WO 2012/061374 A2 | 5/2012 |

OTHER PUBLICATIONS

Baumgartner et al., "Double blind, placebo controlled trial of tumor necrosis factor receptor fusion protein (TNFR:Fc) in active rheumatoid arthritis," Biomedicine '96. Medical Research from Bench to Bedside. Washington, DC, May 3-6, 1996. *J. Invest. Med.*, 44(3):235A (Mar. 1996) (Abstract) (1 page).

Boado et al., "Fusion Antibody for Alzheimer's Disease with Bidirectional Transport Across the Blood-Brain Barrier and Aβ Fibril Disaggregation," *Bioconj. Chem.*, 18(2): 447-455 (2007).

Bornemann et al., "Aβ-induced Inflammatory Processes in Microglia Cells of APP23 Transgenic Mice," *Am. J. Pathol.*, 158(1): 63-73 (2001).

Bree et al., "IL-13 blockade reduces lung inflammation after *Ascaris suum* challenge in cynomolgus monkeys," *J. Allergy Clin. Immunol.*, 119(5): 1251-1257 (2007).

Buras et al., "Animal Models of Sepsis: Setting the Stage," *Nat. Rev. Drug. Discovery*, 4: 854-865 (2005).

Calandra et al., "Protection from septic shock by neutralization of macrophage migration inhibitory factor," *Nature Med.*, 6(2): 164-170 (2000).

Caron et al., "Chondroprotective Effect of Intraarticular Injections of Interleukin-1 Receptor Antagonist in Experimental Osteoarthritis," *Arthritis Rheum.*, 39: 1535-1544 (1996).

Chikanza et al., "Treatment of patients with rheumatoid arthritis with RP73401 phosphodiesterase Type IV inhibitor," (Abstract No. 1527), *Arthritis Rheum.*, 39(9 Suppl.): S282 (1996) (1 page).

David et al., "Characterization of monoclonal antibodies against prostaglandin E$_2$: Fine specificity and neutralization of biological effects," *Mol. Immunol.*, 22(3): 339-346 (1985).

Dayer et al., "Collagenase Production by Rheumatoid Synovial Cells: Stimulation by a Human Lymphocyte Factor," *Science*, 195: 181-183 (1977).

(56) References Cited

OTHER PUBLICATIONS

Dayer et al., "Effects of Prostaglandin E2, Indomethacin, Trifluoperazine and Drugs Affecting the Cytoskeleton on Collagenase Production by Cultured Adherent Rheumatoid Synovial Cells," *Biochem. Pharmacol.*, 33(18):2893-2899 (1984).
Deane et al., "RAGE mediates amyloid-β peptide transport across the blood-brain barrier and accumulation in brain," *Nature Med.*, 9(7): 907-913 (2003).
Desplat-Jego et al., "Anti-TWEAK monoclonal antibodies reduce immune cell infiltration in the central nervous system and severity of experimental autoimmune encephalomyelitis," *Clin. Immunol.*, 117(1): 15-23 (2005).
Dinarello et al., "Immunological and Inflammatory Functions of the Interleukin-1 Family," *Annu. Rev. Immunol.*, 27: 519-550 (2009).
Dohi et al., "Effect of combination Treatment with TNF-Inhibitor and Anti-TWEAK Antibody in Mouse Colitis Model," *Gastroenterology*, 138(5): S-413, Abstract M1758 (2010).
European Patent Application No. 10814433.8: Supplementary European Search Report and Search Opinion, dated Apr. 18, 2013 (11 pages).
European Patent Application No. 10825739.5: Supplementary European Search Report and Search Opinion, dated Apr. 29, 2013 (13 pages).
European Patent Application No. 10830460.1: Supplementary European Search Report and Search Opinion, dated Apr. 29, 2013 (15 pages).
European Patent Application No. 11820654.9: Supplementary European Search Report and Search Opinion, dated Dec. 17, 2013 (17 pages).
Evans et al., "Efficacy of tumor necrosis factor binding protein (TNF-bp) in the streptococcal cell wall-induced reactivation model of arthritis," (Abstract No. 1540), *Arthritis Rheum.*, 39(9 Suppl.): S284 (1996) (1 page).
Fernandes et al., "In Vivo Transfer of Interleukin-1 Receptor Antagonist Gene in Osteoarthritic Rabbit Knee Joints," *Am. J. Pathol.*, 154(4): 1159-1169 (1999).
Finotto, et al., "Asthmatic changes in mice lacking T-bet are mediated by IL-13," *Int. Immunol.*, 17(8): 993-1007 (2005).
Flierl et al., "Adverse functions of IL-17A in experimental sepsis," *FASEB J.*, 22: 2198-2205 (2008).
GENBANK Accession No. BAL50004, "Anti-prostaglandin E2 antibody kappa light chain [*Mus musculus*]," Feb. 4, 2012 (2 pages).
Genovese et al., "Abatacept for Rheumatoid Arthritis Refractory to Tumor Necrosis Factor α Inhibition," *N. Engl. J. Med.*, 353: 1114-1123 (2005).
Goldring et al., "Modulation by Recombinant Interleukin 1 of Synthesis of Types I and III Collagens and Associated Procollagen mRNA Levels in Cultured Human Cells," *J. Biol. Chem.*, 262: 16724-16729 (1987).
Goldring et al., "Interleukin 1 Suppresses Expression of Cartilage-specific Types II and IX Collagens and Increases Types I and III Collagens in Human Chondrocytes," *J. Clin. Investig.*, 82: 2026-2037 (1988).
Gracie et al., "A proinflammatory role for IL-18 in rheumatoid arthritis," *J. Clin. Invest.*, 104(10): 1393-1401 (1999).
Gu et al., "Generation of Dual-Variable-Domain Immunoglobulin Molecules for Dual-Specific Targeting," *Methods in Enzymology*, 502:25-41 (2012).
Guttadauria, M., "Tenidap in Rheumatoid Arthritis Collaborative International Study (TRACIS): a 6-month interim analysis," (Abstract No. 1516), *Arthritis Rheum.*, 39(9 Suppl.): S280 (1996) (1 page).
Hart et al., "Preclinical efficacy and safety of mepolizumab (SB-240563), a humanized monoclonal antibody to IL-5, in cynomolgus monkeys," *J. Allergy Clin. Immunol.*, 108(2): 250-257 (2001).
Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Hill et al., "Interleukin-17 deficiency improves locomotor recovery and tissue sparing after spinal cord contusion injury in mice," *Neurosci. Lett.*, 487(3): 363-367 (2011).
Holm et al., "Functional mapping and single chain construction of the anti-cytokeratin 8 monoclonal antibody TS1," *Mol. Immunol.*, 44: 1075-1084 (2007).
*Inter Partes* Reexamination (Control No. 95/001,380) of U.S. Patent No. 7,612,181 (U.S. Appl. No. 11/507,050): Reexamination Non-Final Office Action ("Action Closing Prosecution"), dated Sep. 1, 2011.
*Inter Partes* Reexamination (Control No. 95/001,380) of U.S. Patent No. 7,612,181 (U.S. Appl. No. 11/507,050): Patent Owner Comments After Action Closing Prosecution ("Response Pursuant to 37 CFR § 1.951(a)"), dated Oct. 31, 2011.
*Inter Partes* Reexamination (Control No. 95/001,380) of U.S. Patent No. 7,612,181 (U.S. Appl. No. 11/507,050): Third Party Requester Comments after Action Closing Prosecution ("Sanofi's Comments Pursuant to 37 CFR §1.951(a)"), dated Nov. 30, 2011.
*Inter Partes* Reexamination (Control No. 95/001,380) of U.S. Patent No. 7,612,181 (U.S. Appl. No. 11/507,050): Right of Appeal Notice (37 CFR 1.953), dated Mar. 7, 2012.
*Inter Partes* Reexamination (Control No. 95/001,380) of U.S. Patent No. 7,612,181 (U.S. Appl. No. 11/507,050): Decision on Appeal, dated Mar. 24, 2014.
Ito et al., "Transfer of Severe Experimental Autoimmune Encephalomyelitis by IL-12- and IL-18-Potentiated T Cells is Estrogen Sensitive," *J. Immunol.*, 170(9): 4802-4809 (2003).
Jakubowski et al., "Dual role for TWEAK in angiogenic regulation," *J. Cell Sci.*, 115(2): 267-274 (2002).
Janelsins et al., "Early correlation of microglial activation with enhanced tumor necrosis factor-alpha and monocyte chemoattractant protein-I expression specifically within the entorhinal cortex of triple transgenic Alzheimer's disease mice," *J. Neuroinflammation*, 2(23): 1-12 (2005).
Jones, R., "Rovelizumab—ICOS Corp," *IDrugs*, 3(4): 442-446 (2000).
Ju et al., "Inhibitory effects of nardostachin on nitric oxide, prostaglandin E2, and tumor necrosis factor-alpha production in lipopolysaccharide activated macrophages," *Biol. Pharm. Bull.* 26: 1375-1378 (2003).
Kaine et al., "Results of a multi-dose protocol 7002 using an immunomodulating, non-depleting Primatized™ anti-CD4 monoclonal antibody in rheumatoid arthritis (RA)," (Abstract No. 195), *Arthritis Rheum.*, 38; S185 (1995) (1 page).
Kapadia et al., "Soluble TNF binding proteins modulate the negative inotropic properties of TNF-alpha in vitro," *Am. J. Physiol. Heart Circ. Physiol.* 268 (2 Pt. 2): H517-H525 (1995).
Karnezis et al., "The neurite outgrowth inhibitor Nogo A is involved in autoimmune-mediated demyelination," *Nature Neurosci.*, 7: 736-744 (2004).
Karni et al., "IL-18 is linked to raised IFN-γ in multiple sclerosis and is induced by activated $CD4^+$ T cells via CD40-CD40 ligand interactions," *J. Neuroimmunol.*, 125: 134-140 (2002).
Keith Jr., et al., "Recombinant human interleukin eleven decreases arthritis in HLA-B27 transgenic rats," (Abstract No. 1613), *Arthritis Rheum.*, 39(9 Suppl.): S296 (1996) (1 page).
Kim and Moalem-Taylor, "Interleukin-17 Contributes to Neuroinflammation and Neuropathic Pain Following Peripheral Nerve Injury in Mice," *J. Pain*, 12(3): 370-383 (2010).
Klein, W.L., "Aβ toxicity in Alzheimer's disease: Globular oligomers (ADDLs) as new vaccine and drug targets," *Neurochem. Int.*, 41: 345-352 (2002).
Klyubin et al., "Amyloid β protein immunotherapy neutralizes Aβ oligomers that disrupt synaptic plasticity in vivo," *Nature Med.*, 11: 556-561 (2005).
Krop et al., "Self-renewal of B-1 lymphocytes is dependent on CD19," *Eur. J. Immunol.*, 26: 238-242 (1996).
Kwong et al., "Generation, affinity maturation, and characterization of a human anti-human NKG2D monoclonal antibody with dual antagonistic and agonistic activity," *J. Mol. Biol.*, 384(5): 1143-1156 (2008).
Kyte et al., "A Simple Method for Displaying the Hydropathic Character Protein," *J. Mol. Biol.*, 157: 105-132 (1982).

(56) References Cited

OTHER PUBLICATIONS

Leung et al., "Combined Effects of IL-12 and IL-18 on the Induction of Collagen-Induced Arthritis," *J. Immunol.*, 164(12): 6495-6502 (2000).
Lotz et al., "IL-17 promotes cartilage degradation," (Abstract No. 559), *Arthritis Rheum.*, 39(9 Suppl.): S120 (1996) (1 page).
Madhusudan et al., "A phase II study of etanercept (Enbrel), a tumor necrosis factor alpha inhibitor in patients with metastatic breast cancer," *Clin. Cancer Res.*, 10(19): 6528-6534 (2004).
Malfait et al., "ADAMTS-5 deficient mice do not develop mechanical allodynia associated with osteoarthritis following medial meniscal destabilization," *Osteoarthritis Cartilage*, 18: 572-580 (2010).
Masliah et al., "Effects of α-Synuclein Immunization in a Mouse Model of Parkinson's Disease." *Neuron*, 46:857-868 (2005).
McDonnell et al., "TNF Antagonism," In *New Drugs for Asthma, Allergy and COPD, Prog. Respir. Res.*, vol. 31. (Hansel et al., eds.) (Karger, Basel, 2001) pp. 247-250.
McGee et al., "The Nogo-66 receptor: Focusing myelin inhibition of axon regeneration," *Trends in Neurosciences*, 26(4): 193-198 (2003).
McGuire-Goldring et al., "In Vitro Activation of Human Chondrocytes and Synovlocytes by a Human Interleukin-1-Like Factor," *Arthritis Rheum.*, 27(6): 654-662 (1984).
McMahon et al., "Does Anti-TNF-Alpha Have a Role in the Treatment of Osteoporosis?" *Bulletin of the NYU Hospital for Joint Diseases*, 66: 280-281 (2008).
Miossec et al., "Targeting IL-17 and TH17 cells in chronic inflammation," *Nat. Rev. Drug. Disc.*, 11(10): 763-776 (2012).
Mnich et al., "Characterization of a monoclonal antibody that neutralizes the activity of prostaglandin $E_2$" *J. Immunol.*, 155: 4437-4444 (1995).
Modjtahedi et al., "Antitumor Activity of Combinations of Antibodies Directed Against Different Epitopes on the Extracellular Domain of the Human EGF Receptor," *Cell Biophys.*, 22(1-3): 129-146 (1993).
Modjtahedi et al., "Phase I trial and tumour localisation of the anti-EGFR monoclonal antibody 1CR62 in head and neck or lung cancer," *Br. J. Cancer*, 73: 228-235 (1996).
Modjtahedi et al., "Targeting of Cells Expressing Wild-Type EGFR and Type-III Mutant EGFR (EGFRVIII) by Anti-EGFR MAB ICR62: A Two-Pronged Attack for Tumour Therapy," *Int. J. Cancer*, 105: 273-280 (2003).
Modjtahedi et al., "The human EGF receptor as a target for cancer therapy: Six new rat mAbs against the receptor on the breast carcinoma MDA-MB 468", *Br. J. Cancer*, 67: 247-253 (1993).
Moreland et al., "Soluble tumor necrosis factor receptors (sTNFR): Results of a phase I dose-escalation study in patients with rheumatoid arthritis," (Abstract No. 813), *Arthritis Rheum.*, 37: S295 (1994) (1 page).
Morgan et al., "Dissociation of hyperalgesia from fever following intracerebroventricular administration of interleukin-1β in the rat," *Brain Res.*, 1022(1-2): 96-100 (2004).
Morimoto et al., "The Increased Interleukin-13 in Patients with Systemic Lupus Erythematosus: Relations to Other Th1-, Th2-Related Cytokines and Clinical Findings," *Autoimmunity*, 34(1): 19-25 (2001).
Moriuchi et al., "Treatment of established collagen-induced arthritis with PGE1 incorporated in lipid microspheres," (Abstract No. 1528), *Arthritis Rheum.*, 39(9 Suppl.): S282 (1996) (1 page).
Murthy et al., "Binding of an Antagonistic Monoclonal Antibody to an Intact and Fragmented EGF-Receptor Polypeptide," *Arch. Biochem. Biophys.*, 252(2): 549-560 (1987).
Nakanishi et al., "Interleukin-18 Regulates Both TH1 and TH2 Responses," *Ann. Rev. Immunol.*, 19: 423-474 (2001).
Nalbandian et al., "Interleukin-17 and systemic lupus erythematosus: current concepts," *Clin. Exp. Immunol.*, 157(2): 209-215 (2009).
National Center for Biotechnology Information (NCBI), Protein Database, "Chain H, Vascular Endothelial Growth Factor in Complex with a Neutralizing Antibody," Accession No. 1BJ1_H, ROD Jun. 30, 1998 [online]. Retrieved from the Internet: http://www.ncbi.nlm.nih.gov/protein/1BJ1_H (3 pages).
National Center for Biotechnology Information (NCBI), Protein Database, "Chain L, Vascular Endothelial Growth Factor in Complex with a Neutralizing Antibody," Accession No. 1BJ1_L, ROD Jun. 30, 1998 [online]. Retrieved from the Internet: http://www.ncbi.nlm.nih.gov/protein/4389276?sat=11&satkey=3623907 (3 pages).
Nishimoto et al., "Treatment of rheumatoid arthritis with humanized anti-interleukin-6 receptor antibody," *Arthritis Rheum.*, 50(6): 1761-1769 (2004).
Okamoto et al., "Rituximab for Rheumatoid Arthritis," *N. Engl. J. Med.*, 351: 1909 (2004) (1 page).
Padilla et al., "IL-13 Regulates the Immune Response to Inhaled Antigens," *J. Immunol.*, 74(12): 8097-8105 (2005).
Parikh et al., "Urine NGAL and IL-18 are predictive biomarkers for delayed graft function following kidney transplantation," *Am. J. Transplant.*, 6(7): 1639-1645 (2006).
Park and Lee, "Interleukin-17 regulation: an attractive therapeutic approach for asthma," *Respir. Res.*, 11: 78 (2010).
Pelletier et al., "In Vivo Suppression of Early Experimental Osteoarthritis by Interleukin-1 Receptor Antagonist Using Gene Therapy," *Arthritis Rheum.*, 40(6): 1012-1019 (1997).
Pettiphar et al., "Interleukin 1 induces leukocyte infiltration and cartilage proteoglycan degradation in the synovial joint," *Proc. Natl. Acad. Sci. USA*, 83: 8749-8753 (1986).
PIR (Protein Information Resource) Accession No. PC4203, "Ig kappa chain (monoclonal antibody MabA34)—mouse (fragment)," Jan. 11, 2000 (2 pages).
Portanova et al., "Selective Neutralization of Prostaglandin $E_2$ Blocks Inflammation, Hyperalgesia, and Interleukin 6 Production In Vivo," *J. Exp. Med.*, 184(3): 883-891 (1996).
Qu et al., "Bispecific anti-CD20/22 antibodies inhibit B-cell lymphoma proliferation by a unique mechanism of action," *Blood*, 111(4): 2211-2219 (2007).
Riemer et al., "Matching of trastuzumab (Herceptin®) epitope mimics onto the surface of Her-2/neu—a new method of epitope definition" *Mol. Immunol.*, 42: 1121-1124 (2005).
Scholz, P., "Inhibition of the production and effect of TNF-alpha by iloprost: possible impact for treatment of rheumatoid arthritis," (Abstract No. 336), *Arthritis Rheum.*, 39(9 Suppl.): S82 (1996).
Sfikakis et al., "Rituximab anti-B-cell therapy in systemic lupus erythematosus: Pointing to the future," *Curr. Opin. Rheumatol.*, 17: 550-557 (2005).
Shukla et al., "HER2 specific delivery of methotrexate by dendrimer conjugated anti-Her2 mAB," *Nanotechnology*, 19:295102 (2008) (7 pages).
Sims et al., "A Humanized CD18 Antibody Can Block Function without Cell Destruction," *J. Immunol.*, 151(4):2296-2308 (1993).
Stamper et al., "Crystal structure of the B7-1/CTLA-4 complex that inhibits human immune responses,"*Nature*, 410: 608-611 (2001).
Stancovski et al., "Mechanistic aspects of the opposing effects of monocional antibodies to the ERBB2 receptor on tumor growth," *Proc. Natl. Acad. Sci. USA*, 88: 8691-8695 (1991).
Tarsca et al. "Dual-Variable Domain Immunoglobulin (DVD-Ig™ Technology: A Versatile, Novel Format for the Next Generation of Dual-Targeting Biologics," Chapter 10 in *Bispecific Antibodies*. Roland E. Kontermann (ed.), Springer, New York, 2011; pp. 171-185.
Thoss et al., "Immunomodulation of rat antigen-induced arthritis by leflunomide alone and in combination with cyclosporin A," *Inflamm. Res.*, 45: 103-107 (1996).
U.S. Appl. No. 12/431,460, filed Apr. 28, 2009 by Ghayur et al.: Non-Final Office Action, Apr. 4, 2014.
U.S. Appl. No. 12/431,460, filed Apr. 28, 2009 by Ghayur et al.: Final Office Action, Aug. 7, 2014.
U.S. Appl. No. 12/477,668, filed Jun. 3, 2009 by Ghayur et al.: Non-Final Office Action, Mar. 10, 2014.
U.S. Appl. No. 12/477,711, filed Jun. 3, 2009 by Ghayur et al.: Non-Final Office Action, Jul. 17, 2013.
U.S. Appl. No. 12/477,711, filed Jun. 3, 2009 by Ghayur et al.: Final Office Action, Feb. 7, 2014.
U.S. Appl. No. 12/477,711, filed Jun. 3, 2009 by Ghayur et al.: Non-Final Office Action, Jul. 29, 2014.
U.S. Appl. No. 12/499,652, filed Jul. 8, 2009 by Ghayur et al.: Notice of Allowance, Apr. 10, 2014.

(56) References Cited

OTHER PUBLICATIONS

U.S. Appl. No. 12/631,483, filed Dec. 4, 2009 by Jakob et al.: Non-Final Office Action, May 27, 2014.
U.S. Appl. No. 12/771,871, filed Apr. 30, 2010 by Ghayur et al.: Final Office Action, May 28, 2013.
U.S. Appl. No. 12/771,871, filed Apr. 30, 2010 by Ghayur et al.: Non-Final Office Action, Apr. 15, 2014.
U.S. Appl. No. 12/846,317, filed Jul. 29, 2010 by Ghayur et al.: Final Office Action, May 23, 2013.
U.S. Appl. No. 12/846,317, filed Jul. 29, 2010 by Ghayur et al.: Final Office Action, Nov. 6, 2013.
U.S. Appl. No. 12/873,926, filed Sep. 1, 2010 by Ghayur et al.: Notice of Allowance, Jul. 24, 2013.
U.S. Appl. No. 12/905,474, filed Oct. 15, 2010 by Ghayur et al.: Notice of Allowance, Jan. 10, 2014.
U.S. Appl. No. 12/914,614, filed Oct. 28, 2010 by Ghayur et al.: Non-Final Office Action, Jun. 6, 2013.
U.S. Appl. No. 12/914,614, filed Oct. 28, 2010 by Ghayur et al.: Notice of Allowance, Jan. 10, 2014.
U.S. Appl. No. 13/196,138, filed Aug. 2, 2011 by Ghayur et al.: Notice of Allowance, Jan. 16, 2014.
U.S. Appl. No. 13/286,707, filed Nov. 1, 2011 by Ghayur et al.: Non-Final Office Action, Jan. 29, 2014.
U.S. Appl. No. 13/286,707, filed Nov. 1, 2011 by Ghayur et al.: Final Office Action, Aug. 29, 2014.
Winkles, J., "The TWEAK-Fn14 cytokine-receptor axis: discovery, biology and therapeutic targeting," *Nature Reviews, Drug Disc.*, 7(5): 411-425 (2008).
Witkowski et al., "Interleukin-17: A mediator of inflammatory responses," *Cell. Mol. Life Sci.*, 61: 567-579 (2004).
Wong et al., "Hyperproduction of IL-23 and IL-17 in patients with systemic lupus erythematosus: Implications for Th17-mediated inflammation in autoimmunity," *Clin. Immunol.*, 127(3): 385-393 (2008).
Yao et al., "Human IL-17: A Novel Cytokine Derived from T Cells," *J. Immunol.*, 155: 5483-5486 (1995).
Yao et al., "Molecular characterization of the human interleukin (IL)-17 receptor," *Cytokine*. 9(11): 794-800 (1997).
Zhang et al., "Direct chitosan-mediated gene delivery to the rabbit knee joints in vitro and in vivo," *Biochem. Biophys. Res. Commun.*, 341: 202-208 (2006).
Alderson et al., "Regulation of apoptosis and T cell activation by Fas-specific mAb," *Int. Immunol.*, 6(11):1799-1806 (1994).
Alt et al., "Novel tetravalent and bispecific IgG-like antibody molecules combining single-chain diabodies with the immunoglobulin gl Fc or CH3 region," *FEBS Letters*, 454: 90-94 (1999).
Ames et al., "Conversion of murine Fabs isolated from a combinatorial phage display library to full length immunoglobulins," *J. Immunol. Methods*, 184: 177-186 (1995).
Andrew et al., "Fragmentation of Immunoglobulin G," *Current Protocols in Cell Biology*, 16.4.1-16.4.10 (2000).
Andrew et al., "Fragmentation of Immunoglobulin G," *Current Protocols in Cell Biology*, 2.8.1-2.8.10 (1997).
Aoki et al., "Endothelial Progenitor Cell Capture by Stents Coated with Antibody Against CD34," *J. Am. Coll. Cardiol.*, 45(10): 1574-1579 (2005).
Arancio et al., "RAGE potentiates Aβ-induced perturbation of neuronal function in transgenic mice," *EMBO J.*, 23: 4096-4105 (2004).
Arndt et al., "Bispecific Diabodies for Cancer Therapy," *Methods Mol. Biol.*, 207: 305-321 (2003).
Azzazy et al., "Phage display technology: clinical applications and recent innovations," *Clin. Biochem.*, 35:425-445 (2002).
Babcook et al., "A novel strategy for generating monoclonal antibodies from single, isolated lymphocytes producing antibodies of defined specificities," *Proc. Natl. Acad. Sci. USA*, 93: 7843-7848 (1996).
Bäckström et al., "Signaling Efficiency of the T Cell Receptor Controlled by a Single Amino Acid in the b Chain Constant Region," *J. Exp. Med.*, 186 (11): 1933-1938 (1997).

Balthasar et al., "High-affinity rabbit antibodies directed against methotrexate: Production, purification, characterization, and pharmacokinetics in the rat," *J. Pharm. Sci.*, 84(1): 2-6 (1995) (Abstract only) (1 page).
Balthasar et al., "Inverse Targeting of Peritoneial Tumors: Selective Alteration of the Disposition of Methotrexate through the Use of Anti-Methotrexate Antibodies and Antibody Fragments," *J. Pharm. Sci.*, 85(10):1035-1043 (1996).
Barbas et al., "Assembly of combinatorial antibody libraries on phage surfaces: The gene III site," *Proc. Natl. Acad. Sci. USA*, 88: 7978-7982 (1991).
Barrios et al., "Length of the antibody heavy chain complementarity determining region 3 as a specificity-determining factor," *J. Mol. Recog.*, 17: 332-338 (2004).
Berzofsky et al., "Immunogenicity and Antigen Structure," in *Fundamental Immunology*. (Paul, W.E. ed.), New York, NY: Raven Press, 1993; Chapter 8, p. 242 (1 page).
Bessis et al., "Use of hollow fibers filled with cells engineered to secrete IL-4 or IL-13 for treatment of experimental arthritis," (Abstract No. 1681), *Arthritis Rheum.*, 39(9Suppl.): S308 (1996) (1 page).
Better et al., "*Escherichia coli* Secretion of an Active Chimeric Antibody Fragment," *Science*, 240: 1041-1043 (1988).
Biewenga et al., "IgA1 half molecules in human multiple myeloma and the in vitro production of similar fragments from intact IgA1 molecules," *Clin. Exp. Immunol.*, 51: 395-400 (1983).
Billiard et al., "Dll4—Notch signaling in Flt3-independent dendritic cell development and autoimmunity in mice," *J. Exp. Med.*, 209(5): 1011-1028 (2012).
Bird et al., "Single-Chain Antigen-Binding Proteins," *Science*, 242: 423-426 (1988).
Boyce et al., "No audible wheezing: Nuggets and conundrums from mouse asthma models," *J. Exp. Med.*, 201(12): 1869-1873 (2005).
Brand, D.D., "Rodent Models of Rheumatoid Arthritis," *Comparative Medicine*, 55(2): 114-122 (2005).
Brennan et al., "Preparation of Bispecific Antibodies by Chemical Recombination of Monoclonal Immunoglobulin $G_1$ Fragments," *Science*, 229: 81-83 (1985).
Brinkmann et al., "Phage display of disulfide-stabilized Fv fragments," *J. Immunol. Methods*, 182: 41-50 (1995).
Bruncko et al., "Studies leading to potent, dual inhibitors of Bcl-2 and Bcl-xL," *J. Med. Chem.*, 50(4): 641-662 (2007).
Brüsselbach et al., "Enzyme recruitment and tumor cell killing in vitro by a secreted bispecific single-chain diabody," *Tumor Targeting*, 4: 115-123 (1999).
Buchwald et al., "Long-term, continuous intravenous heparin administration by an implantable infusion pump in ambulatory patients with recurrent venous thrombosis," *Surgery*, 88: 507-516 (1980).
Burke et al., "Zotarolimus (ABT-578) eluting stents," *Adv. Drug Del. Rev.*, 58: 437-446 (2006).
Burton et al., "Human Antibodies from Combinatorial Libraries," *Adv. Immunol.*, 57: 191-280 (1994).
Carroll et al., "The selection of high-producing cell lines using flow cytometry and cell sorting," *Expert Opin. Biol. Ther.*, 4: 1821-1829 (2004).
Carter et al., "Humanization of an anti-p185$^{HER2}$ antibody for human cancer therapy," *Proc. Natl. Acad. Sci. USA*, 89: 4285-4289 (1992).
Casset et al., "A peptide mimetic of an anti-CD4 monoclonal antibody by rational design," *Biochem. Biophys. Res. Commun.*, 307: 198-205 (2003).
Chayen, N.E., "Turning protein crystallisation from an art into a science" *Curr. Opin. Struct. Biol.*,14:577-583 (2004).
Chayen et al., "Protein crystallization: from purified protein to diffraction-quality crystal," *Nature Methods*,5(2):147-153 (2008).
Chen et al., "Selection and analysis of an optimized anti-VEGF antibody: Crystal structure of an affinity matured Fab in complex with antigen," *J. Mol. Biol.*, 293: 865-881 (1999).
Choi et al., "Recombinant chimeric OKT3 scFv IgM antibodies mediate immune suppression while reducing T cell activation in vitro," *Eur. J. Immunol.*, 31(1): 94-106 (2001).
Chothia et al., "Canonical Structures for the Hypervariable Regions of Immunoglobulins," *J. Mol. Biol.*, 196:901-917 (1987).

(56) References Cited

OTHER PUBLICATIONS

Chothia et al., "Conformations of immunoglobulin hypervariable regions," *Nature*, 342: 877-883 (1989).
Clackson et al., "Making antibody fragments using phage display libraries," *Nature*, 352: 624-628 (1991).
Cleek et al., "Biodegradable Polymeric Carriers for a bFGF Antibody for Cardiovascular Application," *Proceed. Intl. Symp. Control. Rel. Bioact. Mater.*, 24: 853-854 (1997).
Co et al., "Genetically Engineered Deglycosylation of the Variable Domain Increases the Affinity of an Anti-CD33 Monoclonal Antibody," *Mol. Immunol.*, 30(15): 1361-1367 (1993).
Coffman et al., "Nonhuman primate models of asthma," *J. Exp. Med.*, 201(12): 1875-1879 (2005).
Colman, "Effects of amino acid sequence changes on antibody-antigen interactions," *Research in Immunology*, 145:33-36 (1994).
Coloma et al., "Design and production of novel tetravalent bispecific antibodies," *Nature Biotechnol.*, 15: 159-163 (1997).
Cot et al., "Production and characterization of highly specific anti-methotrexate monoclonal antibodies," *Hybridoma*, 6(1): 87-95 (1987).
Cox et al., "Measurement of cytokine release at the single cell level using the ELISPOT assay," *Methods*, 38(4):274-282 (2006).
D'Andrea et al., "Production of Natural Killer Cell Stimulatory Factor (Interleukin 12) by Peripheral Blood Mononuclear Cells," *J. Exp. Med.*, 176: 1387-1398 (1992).
Dall'Acqua et al., "Contribution of Domain Interface Residues to the Stability of Antibody $C_H3$ Domain Homodimers," *Biochemistry*, 37: 9266-9273 (1998).
Dall'Acqua et al., "Increasing the affinity of a human IgG1 for the neonatal Fc receptor: Biological consequences," *J. Immunol.*, 169(9): 5171-5180 (2002).
Dall'Acqua et al., "Properties of human IgG1s engineered for enhanced binding to the neonatal Fc receptor (FcRn)," *J. Biol. Chem.*, 281: 23514-23524 (2006).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169: 3076-3084 (2002).
Deluca et al., "Marine and botanical lipids as immunomodulatory and therapeutic agents in the treatment of rheumatoid arthritis," *Rheum. Dis. Clin. North Am.*, 21: 759-777 (1995).
Descotes, J., "Immunotoxicology of Immunomodulators," *Develop. Biol. Standard*, 77: 99-102 (1992).
Desmet et al., "Anchor profiles of HLA-specific peptides: analysis by a novel affinity scoring method and experimental validation," *Proteins*, 58: 53-69 (2005).
Dickson, B.J., "Molecular Mechanisms of Axon Guidance," *Science*, 298: 1959-1964 (2002).
Digiammarino et al., "Ligand association rates to the inner-variable-domain of a dual-variable-domain immunoglobulin are significantly impacted by linker design," *mAbs*, 3(5): 487-494 (2011).
Dinarello et al., "Measurement of soluble and membrane-bound interleukin 1 using a fibroblast bioassay," Unit 6.2, In *Current Protocols in Immunology*, pp. 6.21-6.27 (2000) (7 pages).
Domeniconi et al., "Overcoming inhibitors in myelin to promote axonal regeneration," *J. Neurological Sciences*, 233: 43-47 (2005).
Duarte et al., "Dosage-sensitive requirement for mouse DII4 in artery development," *Genes & Dev.*, 18(20):2474-2478 (2004).
During et al., "Controlled Release of Dopamine from a Polymeric Brain Implant: In Vivo Characterization," *Ann. Neurol.*, 25(4): 351-356 (1989).
Durocher et al., "High-level and high-throughput recombinant protein production by transient transfection of suspension-growing human 293-EBNA1 cells," *Nucl. Acids Res.*, 30(2): e9, (9 pages) (2002).
Economides et al., "Cytokine traps: multi-component, high-affinity blockers of cytokine action," *Nature Med.*, 9(1): 47-52 (2003).

Enrich et al., "Demonstration of selective COX-2 inhibition by MK-966 in humans," (Abstract No. 328), *Arthritis Rheum.*, 39(9 Suppl.): S81 (1996) (1 page).
Enrich et al., "Efficacy of MK-966, a highly selective inhibitor of COX-2, in the treatment of postoperative dental pain," (Abstract No. 329), *Arthritis Rheum.*, 39(9Suppl.): S81 (1996) (1 page).
European Patent Application No. 06813554.0: Supplementary European Search Report and Search Opinion, dated Sep. 21, 2009 (11 pages).
European Patent Application No. 07811045.9: Supplementary European Search Report and Search Opinion, dated Sep. 21, 2009 (7 pages).
European Patent Application No. 09739578.4: Supplementary European Search Report and Search Opinion, dated Mar. 28, 2012 (21 pages).
European Patent Application No. 09759344.6: Supplementary European Search Report and Search Opinion, dated Jun. 13, 2012 (12 pages).
European Patent Application No. 09759348.7: Supplementary European Search Report and Search Opinion, dated Jul. 4, 2012 (11 pages).
European Patent Application No. 09795128.9: Supplementary European Search Report and Search Opinion, dated May 22, 2013 (10 pages).
European Patent Application No. 09831213.5: Supplementary European Search Report and Search Opinion, dated Oct. 21, 2013 (6 pages).
European Patent Application No. 10770441.3 Supplementary European Search Report and Search Opinion, dated Sep. 23, 2013 (16 pages).
European Patent Application No. 10805046.9: Supplementary European Search Report and Search Opinion, dated Mar. 26, 2013 (7 pages).
European Patent Application No. 10824164.7: Supplementary European Search Report and Search Opinion, dated May 22, 2013 (11 pages).
European Patent Application No. 11804385.0: Supplementary European Search Report and Search Opinion, dated Nov. 20, 2013 (16 pages).
European Patent Application No. 11798923.6: Supplementary European Search Report and Search Opinion, dated Feb. 1, 2014 (10 pages).
Ewert et al., "Stability improvement of antibodies for extracellular and intracellular applications: CDR grafting to stable frameworks and structure-based framework engineering," *Methods*, 34: 184-199 (2004).
Farr et al., "Sulphasalazine (SASP) in rheumatoid arthritis (RA): A 5 year prospective study," (Abstract No. 1519), *Arthritis Rheum.*, 39(9 Suppl.): S281 (1996) (1 page).
Fiebich et al., "Effects of NSAIDs on IL-1-beta-induced IL-6 mRNA and protein synthesis in human astrocytoma cells," *NeuroReport*, 7: 1209-1213 (1996).
Finnegan et al., "Leflunomide inhibits immunoglobulin production by two separate mechanisms," (Abstract No. 627), *Arthritis Rheum.*, 39(9 (Suppl.): S131 (1996) (1 page).
Fuchs et al., "Targeting Recombinant Antibodies to the Surface of *Escherichia coli*: Fusion to a Peptidoglycan Associated Lipoprotein," *Bio/Technology*, 9: 1369-1372 (1991).
Fuh et al., "Structure-Function Studies of Two Synthetic Anti-vascular Endothelial Growth Factor Fabs and Comparison with the Avastin™ Fab," *J. Biol. Chem.*, 281(10):6625-6631 (2006).
Fukuda et al., "Notch ligand Delta-like 4 blockade attenuates atherosclerosis and metabolic disorders," *Proc. Natl. Acad. Sci. USA*, 109(27): E1868-1877 (2012).
Gale et al., "Haploinsufficiency of delta-like 4 ligand results in embryonic lethality due to major defects in arterial and vascular development," *Proc. Natl. Acad. Sci. USA*, 101(45): 15949-15954 (2004).
Garrard et al., "$F_{AB}$ Assembly and Enrichment in a Monovalent Phage Display System," *Bio/Technology*, 9:1373-1377 (1991).
Gavilondo et al., "Antibody Engineering at the Millennium," *Biotechniques*, 29: 128-145 (2000).

(56) References Cited

OTHER PUBLICATIONS

Genain et al., "Creation of a model for multiple sclerosis in *Callithrix jacchus* marmosets," *J. Mol. Med.*, 75(3):187-197 (1997).
GENBANK Accession No. U17870, "*Cricetulus migratorius* 145.2c11 kappa light chain mRNA, complete cds," ROD Feb. 7, 1996 (2 pages).
GENBANK Accession No. U17871, "*Cricetulus migratorius* 145.2c11 heavy chain mRNA, partial cds," Feb. 7, 1996 (2 pages).
GENBANK Accession No. X99230, "*M.musculus* mRNA for immunoglobulin heavy chain variable domain, subgroup IIb," ROD Oct. 8, 1996 (2 pages).
GENBANK Accession No. X99232, "*M.musculus* mRNA for immunoglobulin light chain variable domain, subgroup III," ROD Oct. 8, 1996 (2 pages).
GENBANK Accession No. Y14283, "*Mus musculus* mRNA for immunoglobulin heavy chain variable region, subunits VH, DH and JH" ROD May 26, 1998 (2 pages).
GENBANK Accession No. Y14284, "*Mus musculus* mRNA for immunoglobulin light chain variable region, subunits VL and JL," ROD May 26, 1998 (2 pages).
Germain et al., "Redirecting NK cells mediated tumor cell lysis by a new recombinant bifunctional protein," *Protein Engineering Design and Selection*, 21(11):665-672 (2008).
Ghetie et al., "Increasing the serum persistence of an IgG fragment by random mutagenesis," *Nature Biotechnol.*, 15(7): 637-640 (1997).
Giegé et al., Chapter 1, In *Crystallization of Nucleic Acids and Proteins, a Practical Approach*, 2nd ed., (Ducruix and Giegé, eds.) (Oxford University Press, New York, 1999) pp. 1-16.
Glennie et al., "Preparation and Performance of Bispecific F(ab'γ)$_2$ Antibody Containing Thioether-Linked Fab'γ Fragments," *J. Immunol.*, 139(7): 2367-2375 (1987).
Goldspiel et al., "Human Gene Therapy," *Clin. Pharm.*, 12: 488-505 (1993).
Goodson, J.M., "Dental Applications," Chapter 6, In Medical Applications of Controlled Release, vol. II, Applications and Evaluation, (Langer and Wise, eds.) (CRC Press, Inc., Boca Raton, 1984), pp. 115-138.
Gram et al., "In vitro selection and affinity maturation of antibodies from a naive combinatorial immunoglobulin library," *Proc. Natl. Acad. Sci. USA*, 89: 3576-3580 (1992).
Green et al., "Antigen-specific human monoclonal antibodies from mice engineered with human Ig heavy and light chain YACs," *Nature Genetics*, 7: 13-21 (1994).
Green et al., "Regulation of B Cell Development by Variable Gene Complexity in Mice Reconstituted with Human Immunoglobulin Yeast Artificial Chromosomes," *J. Exp. Med.*, 188(3): 483-495 (1998).
Griffin et al., "Blockade of T Cell Activation Using a Surface-Linked Single Chain Antibody to CTLA-4 (CD152)," *J. Immunol.*, 164: 4433-4442 (2000).
Griffiths et al., "Human anti-self antibodies with high specificity from phage display libraries," *EMBO J.*, 12(2): 725-734 (1993).
Güssow et al., "Humanization of Monoclonal Antibodies," *Methods Enzymol.*, 203: 99-121 (1991).
Hammerling et al., eds., "Appendix: Production of Antibody-Producing Hybridomas in the Rodent Systems," In *Monoclonal Antibodies and T-Cell Hybridomas. Research Monographs in Immunology*, vol. 3. (J.L. Turk, General Editor) (Elsevier, New York, 1981), pp. 563-587.
Hanasaki et al., "Binding of Human Plasma Sialoglycoproteins by the B Cell-specific Lectin CD22," *J. Biol. Chem.*, 270(13): 7543-7550 (1995).
Harrington et al., "Regulation of multiple angiogenic pathways by Dll4 and Notch in human umbilical vein endothelial cells," *Microvasc. Res.*, 75(2): 144-154 (2008).
Hawkins et al., "Selection of Phage Antibodies by Binding Affinity Mimicking Affinity Maturation," *J. Mol. Biol.*, 226: 889-896 (1992).
Hay et al., "Bacteriophage cloning and *Escherichia coli* expression of a human IgM Fab," *Hum. Antibod. Hybridomas*, 3: 81-85 (1992).

Henry et al., "A Prostate-Specific Membrane Antigen Targeted Monoclonal Antibody-Chemotherapeutic Conjugate Designed for the Treatment of Prostate Cancer," *Cancer Res.*, 64: 7995-8001 (2004).
Hickey et al., "The Rheumatoid Arthritis Azathioprine Registry (RAAR)—interim analysis of malignancy and mortality," (Abstract No. 1521), *Arthritis Rheum.*, 39(9 Suppl.): S281 (1996) (1 page).
Hildebrand et al., "Surface coatings for biological activation and functionalization of medical devices," *Surface & Coatings Technology*, 200: 6318-6324 (2006).
Hinton et al., "Engineered human IgG antibodies with longer serum half-lives in primates," *J. Biol. Chem.* 279(8): 6213-6216 (2004).
Holliger et al., "'Diabodies': Small bivalent and bispecific antibody fragments," *Proc. Natl. Acad. Sci. USA*, 90: 6444-6448 (1993).
Holliger et al., "Diabodies: Small bispecific antibody fragments," *Cancer Immunol. Immunother.*, 45: 128-130 (1997).
Hoogenboom et al., "Multi-subunit proteins on the surface of filamentous phage: Methodologies for displaying antibody (Fab) heavy and light chains," *Nucl. Acids Res.*, 19(15): 4133-4137 (1991).
Hoogenboom et al., "Natural and designer binding sites made by phage display technology," *Immunol. Today*, 21(8): 371-378 (2000).
Hoogenboom, H.R., "Designing and optimizing library selection strategies for generating high-affinity antibodies," *Trends Biotechnol.*, 15: 62-70 (1997).
Hoogenboom, H.R., "Mix and match: Building manifold binding sites," *Nature Biotechnol.*, 15: 125-126 (1997).
Howard et al., "Intracerebral drug delivery in rats with lesion-induced memory deficits," *J. Neurosurg.*, 71:105-112 (1989).
Huber et al., "Crystallographic structure studies of an IgG molecule and an Fc fragment," *Nature*, 264: 415-420 (1976).
Huse et al., "Generation of a Large Combinatorial Library of the Immunoglobulin Repertoire in Phage Lambda," *Science*, 246: 1275-1281 (1989).
Huston et al., "Protein engineering of antibody binding sites: Recovery of specific activity in an anti-digoxin single-chain Fv analogue produced in *Escherichia coli*," *Proc. Natl. Acad. Sci. USA*, 85: 5879-5883 (1988).
Huston et al., "Protein Engineering of Single-Chain Fv Analogs and Fusion Proteins," *Methods Enzymol.*, 203:46-88 (1991).
Hwang et al., "Cutting Edge: Targeted Ligation of CTLA-4 In Vivo by Membrane-Bound Anti-CTLA-4 Antibody Prevents Rejection of Allogeneic Cells," *J. Immunol.*, 163: 633-637 (2002).
Inoue et al., "Vascular Endothelial Growth Factor (VEGF) Expression in Human Coronary Atherosclerotic Lesions: Possible Pathophysiological Significance of VEGF in Progression of Atherosclerosis" *Circulation*, 98:2108-2116 (1998).
*Inter Partes* Reexamination (Control No. 95/001,380) of U.S. Patent No. 7,612,181 (U.S. Appl. No. 11/507,050): Replacement Request, dated Jun. 24, 2010 (62 pages).
*Inter Partes* Reexamination (Control No. 95/001,380) of U.S. Patent No. 7,612,181 (U.S. Appl. No. 11/507,050): Order Granting Request for *Inter Partes* Reexamination, issued Sep. 1, 2010 (18 pages).
*Inter Partes* Reexamination (Control No. 95/001,380) of U.S. Patent No. 7,612,181 (U.S. Appl. No. 11/507,050): Reexamination Non-Final Office Action, dated Sep. 1, 2010 (13 pages).
*Inter Partes* Reexamination (Control No. 95/001,380) of U.S. Patent No. 7,612,181 (U.S. Appl. No. 11/507,050): Third Party Requester Comments After Non-Final Action ("Sanofi's Comments Pursuant to 37 CFR § 1.947"), dated Dec. 1, 2010 (81 pages).
*Inter Partes* Reexamination (Control No. 95/001,380) of U.S. Patent No. 7,612,181(U.S. Appl. No. 11/507,050): Response After Non-Final Action—Owner Timely ("Patent Owner's Response Pursuant to 37 CFR § 1.945"), dated Nov. 1, 2010 (71 pages).
International Patent Application No. PCT/US2006/032398: International Preliminary Report on Patentability, dated Jul. 6, 2010 (14 pages).
International Patent Application No. PCT/US2006/032398: International Search Report and Written Opinion, dated Aug. 18, 2008 (14 pages).
International Patent Application No. PCT/US2007/017340: International Preliminary Report on Patentability, dated Nov. 14, 2008 (3 pages).

(56) References Cited

OTHER PUBLICATIONS

International Patent Application No. PCT/US2007/017340: International Search Report and Written Opinion, dated Jun. 24, 2008 (5 pages).
International Patent Application No. PCT/US2009/041945: International Preliminary Report on Patentability, dated Aug. 9, 2010 (12 pages).
International Patent Application No. PCT/US2009/041945: International Search Report and Written Opinion, dated Nov. 2, 2009 (12 pages).
International Patent Application No. PCT/US2009/046130: International Preliminary Report on Patentability, dated Aug. 21, 2010 (13 pages).
International Patent Application No. PCT/US2009/046130: International Search Report and Written Opinion, dated Jan. 11, 2010 (17 pages).
International Patent Application No. PCT/US2009/046137: International Preliminary Report on Patentability, dated Jun. 18, 2010 (14 pages).
International Patent Application No. PCT/US2009/046137: International Search Report and Written Opinion, dated Jan. 12, 2010 (18 pages).
International Patent Application No. PCT/US2009/049954: International Preliminary Report on Patentability, dated Jul. 2, 2011 (11 pages).
International Patent Application No. PCT/US2009/049954: International Search Report and Written Opinion, dated Mar. 31, 2010 (14 pages).
International Patent Application No. PCT/US2009/066815: International Preliminary Report on Patentability, dated Jan. 6, 2011 (13 pages).
International Patent Application No. PCT/US2009/066815: International Search Report and Written Opinion, dated Mar. 23, 2010 (14 pages).
International Patent Application No. PCT/US2010/033231: International Preliminary Report on Patentability, dated Apr. 27, 2011 (10 pages).
International Patent Application No. PCT/US2010/033231: International Search Report and Written Opinion, dated Nov. 22, 2010 (10 pages).
International Patent Application No. PCT/US2010/033246: International Preliminary Report on Patentability, dated May 4, 2011 (28 pages).
International Patent Application No. PCT/US2010/033246: International Search Report and Written Opinion, dated Nov. 24, 2010 (18 pages).
International Patent Application No. PCT/US2010/043716: International Preliminary Report on Patentability, dated Aug. 31, 2012 (24 pages).
International Patent Application No. PCT/US2010/043716: International Search Report and Written Opinion, dated Feb. 28, 2011 (17 pages).
International Patent Application No. PCT/US2010/047543: International Search Report and Written Opinion, dated Feb. 24, 2011 (14 pages).
International Patent Application No. PCT/US2010/052843: International Search Report and Written Opinion, dated Jul. 1, 2011 (21 pages).
International Patent Application No. PCT/US2010/053730: International Preliminary Report on Patentability, dated Nov. 21, 2011 (12 pages).
International Patent Application No. PCT/US2010/053730: International Search Report and Written Opinion, dated May 6, 2011 (13 pages).
International Patent Application No. PCT/US2010/054521: International Preliminary Report on Patentability, dated Feb. 8, 2012 (12 pages).
International Patent Application No. PCT/US2010/054521: International Search Report and Written Opinion, dated May 26, 2011 (12 pages).
International Patent Application No. PCT/US2011/041633: International Search Report and Written Opinion, dated Mar. 13, 2012 (16 pages).
International Patent Application No. PCT/US2011/043297: International Search Report and Written Opinion, dated Feb. 28, 2012 (19 pages).
International Patent Application No. PCT/US2011/046233: International Search Report and Written Opinion, dated Apr. 3, 2012 (17 pages).
International Patent Application No. PCT/US2011/049147: International Search Report and Written Opinion, dated Mar. 21, 2012 (16 pages).
International Patent Application No. PCT/US2011/058769: International Search Report and Written Opinion, dated Jun. 15, 2012 (15 pages).
International Patent Application No. PCT/US2011/059074: International Search Report and Written Opinion, dated Jun. 15, 2012 (18 pages).
International Patent Application No. PCT/US2012/071897: International Search Report and Written Opinion, dated Sep. 3, 2013 (17 pages).
International Patent Application No. PCT/US2012/072017: International Search Report and Written Opinion, dated Jul. 17, 2013 (24 pages).
International Patent Application No. PCT/US2012/071929: International Search Report and Written Opinion, dated Sep. 11, 2013 (29 pages).
International Search Report and Written Opinion for International Application No. PCT/US2013/067873 dated May 8, 2014. (23 pages).
Jackson et al., "In Vitro Antibody Maturation, Improvement of a High Affinity, Neutralizing Antibody Against IL-1β," *J. Immunol.*, 154(7): 3310-3319 (1995).
Janeway et al., *Immunobiology. The Immune System in Health and Disease*. 3rd Ed. Current Biology Ltd./Garland Publishing Inc., 1997; Chapter 3, pp. 1-11.
Jefferis, R., "Glycosylation of Recombinant Antibody Therapuetics," *Biotechnol. Prog.*, 21: 11-16 (2005).
Jendreyko et al., "Intradiabodies, Bispecific, Tetravalent Antibodies for the Simultaneous Functional Knockout of Two Cell Surface Receptors," *J. Biol. Chem.*, 278(48):47812-47819 (2003).
Jiang et al., "Regulation of recombinant monoclonal antibody production in Chinese hamster ovary cells: A comparative study of gene copy number, mRNA level, and protein expression," *Biotechnol. Prog.*, 22(1): 313-318 (2006).
Jin et al., "Pharmacokinetic and Pharmacodynamic Effects of High-Dose Monoclonal Antibody Therapy in a Rat Model of Immune Thrombocytopenia," *The AAPS Journal*, 7(4):Article 87, E895-E902 (2006) [online]. Retrieved from: http://www.springerlink.com/content/v6n04672761n9313/fulltext.pdf.
Joachimiak, "High-throughput crystallography for structural genomics" *Curr. Opin. Struct. Biol.*, 19:573-584 (2009).
Johnsson et al., "Comparison of Methods for Immobilization to Carboxymethyl Dextran Sensor Surfaces by Analysis of the Specific Activity of Monoclonal Antibodies," *J. Mol. Recognit.*, 8: 125-131 (1995).
Johnsson et al., "Immobilization of Proteins to a Carboxymethyldextran-Modified Gold Surface for Biospecific Interaction Analysis in Surface Plasmon Resonance Sensors," *Anal. Biochem.*, 198: 268-277 (1991).
Joliot et al., "Antennapedia homeobox peptide regulates neural morphogenesis," *Proc. Natl. Acad. Sci. USA*, 88: 1864-1868 (1991).
Jones et al., "Replacing the complementarity-determining regions in a human antibody with those from a mouse," *Nature*, 321: 522-525 (1986).
Jones, A.G., "Particle formation and separation in suspension crystallization processes," Chapter 4, In *Process, Solid-Liq. Suspensions*, (P. Ayazi Shamlou, ed.) (Butterworth-Heinemann, Oxford, UK, 1993) pp. 93-117.
Jones, A.J.S., "Analytical methods for the assessment of protein formulations and delivery systems," Chapter 2, In *Formulation and Delivery of Proteins and Peptides*, 1st ed., (Cleland and Langer, eds.) (American Chemical Society, Washington, D.C., 1994) pp. 22-45.

(56) References Cited

OTHER PUBLICATIONS

Jönsson et al., "Introducing a biosensor based technology for real-time biospecific interaction analysis," *Ann. Biol. Clin.*, 51: 19-26 (1993).
Jönsson, et al., "Real-Time Biospecific Interaction Analysis Using Surface Plasmon Resonance and a Sensor Chip Technology," *BioTechniques*, 11(5): 620-627 (1991).
Joosten et al., "Anticytokine Treatment of Established Type II Collagen-Induced Arthritis in DBA/1 Mice," *Arthritis Rheum.*, 39(5): 797-809 (1996).
Jungbluth et al., "A monoclonal antibody recognizing human cancers with amplification/overexpression of the human epidermal growth factor receptor," *Proc. Natl. Acad. Sci. USA*, 100(2): 639-644 (2003).
Kabat et al., "Attempts to Locate Complementarity-Determining Residues in the Variable Positions of Light and Heavy Chains," *Ann. NY Acad. Sci.*, 190: 382-391 (1971).
Kanda et al., "Establishment of a GDP-mannose 4,6-dehydratase (GMD) knockout host cell line: A new strategy for generating completely non-fucosylated recombinant therapeutics," *J. Biotechnol.*, 130(3): 300-310 (2007).
Kashmiri et al., "SDR grafting—a new approach to antibody humanization," *Methods*, 36(1): 25-34 (2005).
Kaufman and Sharp, "Amplification and expression of sequences cotransfected with a modular dihydrofolate reductase complementary DNA gene," *J. Mol. Biol.*, 159(4): 601-621 (1982).
Kellerman et al., "Antibody discovery: The use of transgenic mice to generate human monoclonal antibodies for therapeutics," *Curr. Opin. Biotechnol.*, 13: 593-597 (2002).
Kettleborough et al., "Humanization of a mouse monoclonal antibody by CDR-grafting: the importance of framework residues on loop conformation," *Protein Eng.*, 4(7): 773-783 (1991).
Kettleborough et al., "Isolation of tumor cell-specific single-chain Fv from immunized mice using phage-antibody libraries and the reconstruction of whole antibodies from these antibody fragments," *Eur. J. Immunol.*, 24: 952-958 (1994).
Khamaisi et al., "The emerging role of VEGF in diabetic kidney disease," *Neprol. Dial. Transplant.*, 18(8):1427-1430 (2003).
Kim et al., "Identifying amino acid residues that influence plasma clearance of murine IgG1 fragments by site-directed mutagenesis," *Eur. J. Immunol.*, 24: 542-548 (1994).
Kipriyanov et al., "Bispecific CD3×CD19 Diabody for T Cell-Mediated Lysis of Malignant Human B Cells," *Int. J. Cancer*, 77: 763-772 (1998).
Kipriyanov et al., "Generation of recombinant antibodies," *Mol. Biotechnol.*, 12: 173-201 (1999).
Köhler and Milstein, "Continuous cultures of fused cells secreting antibody of predefined specificity," *Nature*, 256: 495-497 (1975).
Konishi et al., "A simple and sensitive bioassay for the detection of human interleukin-18/ interferon-γ-inducing factor using human myelomonocytic KG-1 cells," *J. Immunol. Methods*, 209: 187-191 (1997).
Kontermann, R.E., "Recombinant bispecific antibodies for cancer therapy," *Acta Pharmacologica Sinica*, 26(1): 1-9 (2005).
Kostelny et al., "Formation of a Bispecific Antibody by the Use of Leucine Zippers," *J. Immunol.*, 148(5):1547-1553 (1992).
Krebs et al., "Notch signaling is essential for vascular morphogenesis in mice," *Genes Dev.*, 14(11): 1343-1352 (2000).
Krebs et al., "Haploinsufficient lethality and formation of arteriovenous malformations in Notch pathway mutants," *Genes Dev.*, 18(20): 2469-2473 (2004).
Kriangkum et al., "Bispecific and bifunctional single chain recombinant antibodies," *Biomol. Eng.*, 18: 31-40 (2001).
Kuby, *Immunology*, 2nd ed., (W.H. Freeman and Company, New York, 1994), p. 115, Fig. 5-6 (1 page).
Kyte et al., "A Simple Method for Displaying the Hydropathic Character of a Protein," *J. Mol. Biol.*, 157: 105-132 (1982).
Lam et al., "Microencapsulation of Recombinant Humanized Monoclonal Antibody for Local Delivery," *Proceed. Intl. Symp. Control Rel. Bioact. Mater.*, 24: 759-760 (1997).

Langer and Peppas, "Chemical and Physical Structure of Polymers as Carriers for Controlled Release of Bioactive Agents: A Review," *J. Macromol. Sci. RMC*, C23(1): 61-126 (1983).
Langer, R., "New Methods of Drug Delivery," *Science*, 249: 1527-1533 (1990).
Laue, T., "Analytical centrifugation: equilibrium approach," In *Current Protocols in Protein Science*, (John Wiley & Sons, Inc., New York, 1999), Supplement 18, Unit 20.3, pp. 20.3.1-20.3.13 (13 pages).
Le Gall et al., "Di-, tri- and tetrameric single chain Fv antibody fragments against human CD19: Effect of valency on cell binding," *FEBS Letters*, 453: 164-168 (1999).
Le Gall et al., "Immunosuppressive properties of anti-CD3 single-chain Fv and diabody," *J. Immunol. Methods*, 285: 111-127 (2004).
Lee et al., "BiP and immunoglobulin light chain cooperate to control the folding of heavy chain and ensure the fidelity of immunoglobulin assembly," *Mol. Biol. Cell*, 10: 2209-2219 (1999).
Lee et al., "Treatment of rheumatoid arthritis (RA) with thalidomide," (Abstract No. 1524), *Arthritis Rheum.*, 39(9 Suppl.): S282 (1996) (1 page).
Legros et al., "Characterization of an anti-*Borrelia burgdorferi* OspA conformational epitope by limited proteolysis of monoclonal antibody-bound antigen and mass spectrometric peptide mapping," *Protein Science*, 9: 1002-1010 (2000).
Levy et al., "Inhibition of Calcification of Bioprosthetic Heart Valves by Local Controlled-Release Diphosphonate," *Science*, 228: 190-192 (1985).
Li et al., "Structural mutations in the constant region of the T-cell antigen receptor (TCR)β chain and their effect on TCRα and β chain interaction," *Immunology*, 88: 524-530 (1996).
Li et al., "Synergistic effects of IL-12 and IL-18 in skewing tumor-reactive T-cell responses towards a type I pattern," *Cancer Res.*, 65(3): 1063-1070 (2005).
Li et al., "Genetically engineered brain drug delivery vectors: Cloning, expression and in vivo application of an anti-transferrin receptor single chain antibody-streptavidin fusion gene and protein," *Protein Eng.*, 12(9): 787-796 (1999).
Little et al., "Of mice and men: hybridoma and recombinant antibodies," *Immunol. Today*, 21(8): 364-370 (2000).
Liu et al., "Heterogeneity of Monoclonal Antibodies," *J. Pharm. Sci.*, 97(7):2426-2447 (2008).
Liu et al., "Regulation of *Notch1* and Dll4 by Vascular Endothelial Growth Factor in Arterial Endothelial Cells: Implications for Modulating Arteriogenesis and Angiogenesis," *Mol. Cell Biol.*, 23(1): 14-25 (2003).
Lloyd et al., "Mouse Models of Allergic Airway Disease," *Adv. Immunol.*, 77: 263-295 (2001).
Lo, B., "Antibody Humanization by CDR Grafting," *Methods Mol. Biol.*, 248: 135-159 (2004).
Lobo, "Anti-Methotrexate Fab Fragments for Optimization of Intraperitoneal Methotrexate Chemotherapy," Dissertation, University of New York at Buffalo, Dept. of Pharmaceutical Sciences, Aug. 2002, pp. 1-243. Available online at: http://www.acsu.buffalo.edu/~jb/Thesis%20080802.pdf.
Lobo et al., "Application of anti-methotrexate Fab fragments for the optimization of intraperitoneal methotrexate therapy in a murine model of peritoneal cancer," *J. Pharma. Sci.*, 94(9): 1957-1964 (2005) (Abstract only) (1 page).
Lobov et al., "Delta-like ligand 4 (Dll4) is induced by VEGF as a negative regulator of angiogenic sprouting," *Proc. Natl. Acad. Sci. USA*, 104(9): 3219-3224 (2007).
Lu et al., "A Fully Human Recombinant IgG-like Bispecific Antibody to Both the Epidermal Growth Factor Receptor and the Insulin-like Growth Factor Receptor for Enhanced Antitumor Activity," *J. Biol. Chem.*, 280 (20):19665-19672 (2005).
Lu et al., "Fab-scFv fusion protein: an efficient approach to production of bispecific antibody fragments," *J. Immunol. Methods*, 267:213-226 (2002).
Lu et al., "Di-diabody: A novel tetravalent bispecific antibody molecule by design," *J. Immunol. Methods*, 279:219-232 (2003).
Lu et al., "Simultaneous Blockade of Both the Epidermal Growth Factor Receptor and the Insulin-like Growth Factor Receptor Signal-

(56) References Cited

OTHER PUBLICATIONS ing Pathways in Cancer Cells with a Fully Human Recombinant Bispecific Antibody," *J. Biol. Chem.*, 279(4): 2856-2865 (2004).
Lublin, F.D., "Relapsing Experimental Allergic Encephalomyelitis. An Autoimmune Model of Multiple Sclerosis," *Springer Semin. Immunopathol.*, 8: 197-208 (1985).
Lund et al., "Human Fc gamma RI and Fc gamma RII interact with distinct but overlapping sites on human IgG," *J. Immunol.*, 147: 2657-2662 (1991).
Luster et al., "Use of animal studies in risk assessment for immunotoxicology," *Toxicology*, 92(1-3): 229-243 (1994).
MacCallum et al., "Antibody-antigen Interactions: Contact Analysis and Binding Site Topography," *J. Mol. Biol.*, 262: 732-745 (1996).
Mack et al., "A small bispecific antibody construct expressed as a functional single-chain molecule with high tumor cell cytotoxicity," *Proc. Natl. Acad. Sci. USA*, 92: 7021-7025 (1995).
Mailhos et al., "Delta4, an endothelial specific Notch ligand expressed at sites of physiological and tumor angiogenesis," *Differentiation*, 69(2-3): 135-144 (2001).
Makwana et al., "Molecular mechanisms in successful peripheral regeneration," *FEBS J.*, 272: 2628-2638 (2005).
Malik-Hall et al., "Primary afferent nociceptor mechanisms mediating NGF-induced mechanical hyperalgesia," *Eur. J. Neurosci.*, 21(12): 3387-3394 (2005).
Marchalonis et al., "Evolutionary Factors in the Emergence of the Combinatorial Germline Antibody Repertoire," *Adv. Exp. Med. Biol.*, 484: 13-30 (2001).
Margolin et al., "Protein crystals as novel catalytic materials," *Angew. Chem. Int. Ed.*, 40: 2204-2222 (2001).
Mariuzza et al., "The Structural Basis of Antigen-Antibody Recognition," *Annu. Rev. Biophys. Biophys. Chem.*, 16: 139-159 (1987).
Marks et al., "By-Passing Immunization: Building High Affinity Human Antibodies by Chain Shuffling," *BioTechnology*, 10: 779-783 (1992).
Marquina et al., "Inhibition of B cell death causes the development of an IgA nephropathy in (New Zealand White×C57BL/6)F1-bcl-2 transgenic mice," *J. Immunol.*, 172(11): 7177-7185 (2004).
Martin, A.C.R., "Protein Sequence and Structure Analysis of Antibody Variable Domains," Chapter 31, In *Antibody Engineering*. (Kontermann and Dübel, eds.), (Springer-Verlag, Berlin, 2001), pp. 422-439.
Marvin and Zhu, "Recombinant approaches to IgG-like bispecific antibodies," *Acta Pharmacologica Sinica*, 26(6): 649-658 (2005).
Mateo et al., "Humanization of a mouse monoclonal antibody that blocks the epidermal growth factor receptor: recovery of antagonistic activity," *Immunotechnology*, 3: 71-81 (1997).
McCafferty et al., "Phage antibodies: Filamentous phage displaying antibody variable domains," *Nature*, 348: 552-554 (1990).
McIntosh et al., "In Vivo Induction of IL-6 by Administration of Exogenous Cytokines and Detection of De Novo Serum Levels of IL-6 in Tumor-Bearing Mice," *J. Immunol.*, 143(1): 162-167 (1989).
Mendez et al., "Functional transplant of megabase human immunoglobulin loci recapitulates human antibody response in mice," *Nature Genet.*, 15: 146-156 (1997).
Merchant et al., "An efficient route to human bispecific IgG," *Nature Biotechnol.*, 16: 677-681 (1998).
Michaelson, J., "Dual Targeting of TNF and TWEAK in Inflammatory Bowel Disease: The Promise of a Bispecific Antibody," Conference, Cytokines & Inflammation, Jan. 28, 2011; Agenda, p. 11. Retrieved from the Internet: http://www.cytokinesandinflammation.com/Index.php?option=com_content&view=article&id=50&itemid=54.
Miller et al., "Design, Construction, and In Vitro Analyses of Multivalent Antibodies," *J. Immunol.*, 170: 4854-4861 (2003).
Milstein et al., "Hybrid hybridomas and their use in immunohistochemistry," *Nature*, 305: 537-540 (1983).
Mizushima et al., "pEF-BOS, a powerful mammalian expression vector," *Nucl. Acids Res.*, 18(17): 5322 (1990).
Morgan and Anderson, "Human Gene Therapy," *Ann. Rev. Biochem.*, 62: 191-217 (1993).
Morrison and Schlom, "Recombinant Chimeric Monoclonal Antibodies," Chapter 1, In *Important Advances in Oncology 1990* (J.B. Lippincott Company, Philadelphia, 1990), pp. 3-18.
Morrison et al., "Genetically Engineered Antibody Molecules," *Advances in Immunology*, 44:65-92 (1989).
Morrison, S., "Two heads are better than one," *Nature Biotech.*, 25(11): 1233-1234 (2007).
Müller et al., "The first constant domain ($C_H1$ and $C_L$) of an antibody used as heterodimerization domain for bispecific miniantibodies," *FEBS Lett.*, 422: 259-264 (1998).
Mulligan, R.C., "The Basic Science of Gene Therapy," *Science*, 260: 926-932 (1993).
Mullinax et al., "Expression of a Heterodimeric Fab Antibody Protein in One Cloning Step," *BioTechniques*, 12(6): 864-869 (1992).
National Center for Biotechnology Information (NCBI), Protein Database, "Chain H, Structure of the G6 Fab, a Phage Derived Vegf Binding Fab," Accession No. 2FJF_H, PRI Jan. 2, 2006 [online]. Retrieved from the Internet: http://www.ncbi.nlm.nih.gov/protein/90109456?sat=34&satkey=11061854 (2 pages).
National Center for Biotechnology Information (NCBI), Protein Database, "Chain L, Structure of the G6 Fab, a Phage Derived Vegf Binding Fab," Accession No. 2FJF_L, PRI Jan. 2, 2006 [online]. Retrieved from the Internet: http://www.ncbi.nlm.nih.gov/protein/90109455?sat=34&satkey=11061854 (2 pages).
National Center for Biotechnology Information (NCBI), Protein Database, "Chain H, Structure of the B20-4 Fab, a Phage Derived Fab Fragment, in Complex with Vegf," Accession No. 2FJH_H, PRI Jan. 2, 2006 [online]. Retrieved from the Internet: http://www.ncbi.nlm.nih.gov/protein/90109487?sat=34&satkey=11061856 (2 pages).
National Center for Biotechnology Information (NCBI), Protein Database, "Chain L, Structure of the B20-4 Fab, a Phage Derived Fab Fragment, in Complex with Vegf," Accession No. 2FJH_L, PRI Jan. 2, 2006 [online]. Retrieved from the Internet: http://www.ncbi.nlm.nih.gov/protein/90109486?sat=34&satkey=11061856 (2 pages).
Nelson, R.B. "The Dualistic Nature of Immune Modulation in Alzheimer's Disease: Lessons from the Transgenic Models," *Curr. Pharm. Des.*, 11: 3335-3352 (2005).
Ning et al., "Intratumoral radioimmunotherapy of a human colon cancer xenograft using a sustained-release gel," *Radiotherapy Oncol.*, 39: 179-189 (1996).
Noguera-Troise et al., "Blockade of Dll4 inhibits tumour growth by promoting non-productive angiogenesis," *Nature*, 444(7122): 1032-1037 (2006).
O'Connor et al., "Requirement of multiple phage displayed peptide libraries for optimal mapping of a conformational antibody epitope on CCR5," *J. Immunol. Methods*, 299: 21-35 (2005).
Owens et al., "The Immunology of Multiple Sclerosis and Its Animal Model, Experimental Allergic Encephalomyelitis," *Neurol. Clin.*, 13(1): 51-73 (1995).
Pack and Plückthun, "Miniantibodies: Use of Amphipathic Helices to Produce Functional, Flexibly Linked Dimeric $F_v$ Fragments with High Avidity in *Escherichia coli*," *Biochemistry*, 31: 1579-1584 (1992).
Padlan et al., "Identification of specificity-determining residues in antibodies," *FASEB J.*, 9: 133-139 (1995).
Padlan, E.A., "A Possible Procedure for Reducing the Immunogenicity of Antibody Variable Domains While Preserving Their Ligand-Binding Properties," *Mol. Immunol.*, 28(4/5): 489-498 (1991).
Park et al., "Generation and characterization of a novel tetravalent bispecific antibody that binds to hepatitis B virus surface antigens," *Molecular Immunol.*, 37: 1123-1130 (2000).
Patel et al., "Up-regulation of Delta-like 4 Ligand in Human Tumor Vasculature and the Role of Basal Expression in Endothelial Cell Function," *Cancer Res.*, 65(19): 8690-8697 (2005).
Patel et al., "Up-Regulation of Endothelial Delta-like 4 Expression Correlates with Vessel Maturation in Bladder Cancer," *Clin. Cancer Res.*, 12(16): 4836-4844 (2006).
Pearlman and Nguyen, "Analysis of protein drugs," Chapter 6, In *Peptide and Protein Drug Delivery. Advances in Parenteral Sciences*, vol. 4. 1st ed. (Lee, ed.) (Marcel Dekker, Inc., New York, 1991), pp. 247-301.
Peipp et al., "Bispecific antibodies targeting cancer cells," *Biochem. Soc. Trans.*, 30(4): 507-511 (2002).

(56) References Cited

OTHER PUBLICATIONS

Peng et al., "Experimental Use of Murine Lupus Models," *Methods Mol. Med.*, 102: 227-272 (2004).
Persic et al., "An integrated vector system for the eukaryotic expression of antibodies or their fragments after seletion from phage display libraries," *Gene*, 187: 9-18 (1997).
Petkova et al., "Enhanced half-life of genetically engineered human IgG1 antibodies in a humanized FcRn mouse model: Potential application in humorally mediated autoimmune disease," *Int. Immunol.*, 18: 1759-1769 (2006).
Petrey et al., "Using multiple structure alignments, fast model building, and energetic analysis in fold recognition and homology modeling," *Proteins*, 53: 430-435 (2003).
Pham, V. et al., "De novo proteomic sequencing of a monoclonal antibody raised against OX40 ligand," *Analytical Biochemistry*, 352: 77-86 (2006).
Piatesi et al., "Immunological Optimization of a Generic Hydrophobic Pocket for High Affinity Hapten Binding and Diels-Alder Activity," *ChemBioChem*, 5: 460-466 (2004).
Pimm et al., "A bispecific monoclonal antibody against methotrexate and a human tumour associated antigen augments cytotoxicity of methotrexate-carrier conjugate," *Br. J. Cancer*, 61: 508-513 (1990).
Plückthun et al., "New protein engineering approaches to multivalent and bispecific antibody fragments," *Immunotechnology*, 3: 83-105 (1997).
Poljak, R.J., "Production and structure of diabodies," *Structure*, 2: 1121-1123 (1994).
Portolano et al., "Lack of promiscuity in autoantigen-specific H and L chain combinations as revealed by human H and L chain 'roulette,'" *J. Immunol.*, 150:880-887 (1993).
Presta et al., "Humanization of an Antibody Directed Against IgE," *J. Immunol.*, 151(5): 2623-2632 (1993).
Presta, L.G., "Engineering of therapeutic antibodies to minimize immunogenicity and optimize function," *Adv. Drug. Del. Rev.*, 58: 640-656 (2006).
Presta, L.G., "Molecular engineering and design of therapeutic antibodies," *Curr. Opin. Immunol.*, 20: 460-470 (2008).
Presta, L.G., "Selection, design, and engineering of therapeutic antibodies," *J. Allergy Clin. Immunol.*, 116:731-736 (2005).
REMINGTON: *The Science and Practice of Pharmacy*. 21$^{st}$ ed.(Lippincott Williams & Wilkins, Philadelphia, 2005), pp. 745-747, 802-804, 838, 879-883, 889-890, and 1079-1082 (14 pages).
Reusch et al., "Anti-CD3×Anti-Epidermal Growth Factor Receptor (EGFR) Bispecific Antibody Redirects T Cell Cytolytic Activity to EGFR-Positive Cancers In vitro and in an Animal Model," *Clin. Cancer Res.*, 12(1): 183-190 (2006).
Ridgway et al., "'Knobs-into-holes' engineering of antibody $C_H3$ domains for heavy chain heterodimerization," *Protein Eng.*, 9(7): 617-621 (1996).
Ridgway et al., "Inhibition of Dll4 signalling inhibits tumour growth by deregulating angiogenesis," *Nature*, 444(7122): 1083-1087 (2006).
Riechmann et al., "Reshaping human antibodies for therapy," *Nature*, 332: 323-327 (1988).
Roberts et al., "RNA-peptide fusions for the in vitro selection of peptides and proteins," *Proc. Natl. Acad. Sci. USA*, 94: 12297-12302 (1997).
Robinson, C., "Gene therapy—proceeding from laboratory to clinic," *Trends Biotechnol.*, 11(5): 155 (1993) (1 page).
Rodeck et al., "Interations Between Growth Factor Receptors and Corresponding Monoclonal Antibodies in Human Tumors," *J. Cell Biochem.*, 35: 315-320 (1987).
Roguska et al., "A comparison of two murine monoclonal antibodies humanized by CDR-grafting and variable domain resurfacing," *Protein Eng.*, 9(10): 895-904 (1996).
Roguska et al., "Humanization of murine monoclonal antibodies through variable domain resurfacing," *Proc. Natl. Acad. Sci. USA*, 91: 969-973 (1994).

Ronday et al., "Tranexamic acid (TEA), an inhibitor of plasminogen activation, reduces collagen crosslink excretion in arthritis," (Abstract No. 1541), *Arthritis Rheum.*, 39(9 Suppl.): S284 (1996) (1 page).
Ross, J.M., "Sulfasalazine (SSZ) toxicity: An assessment of American College of Rheumatology (ACR) monitoring guidelines for SSZ," (Abstract No. 1520), *Arthritis Rheum.*, 39(9 Suppl.): S281 (1996) (1 page).
Rudikoff et al., "Single amino acid substitution altering antigen binding specificity," *Proc. Natl. Acad. Sci. USA*, 79: 1979-1983 (1982).
Sambrook and Russell (eds.), *Molecular Cloning: A Laboratory Manual*. 3$^{rd}$ Ed. Cold Spring Harbor Laboratory Press, Cold Spring Harbor, NY, 2001; pp. 1.10-1.15, 1.84-1.87, 8.18-8.24, 15.54-15.59, and 16.47-16.55 (18 pages).
Santos et al., "Generation and Characterization of a Single Gene-encoded Single-Chain-Tetravalent Antitumor Antibody," *Clin. Cancer Res.*, 5 (Suppl.): 3118s-3123s (1999).
Satoh et al., "Non-fucosylated therapeutic antibodies as next-generation therapeutic antibodies," *Expert Opin. Biol. Ther.*, 6(11): 1161-1173 (2006).
Saudek et al., "A Preliminary Trial of the Programmable Implantable Medication System for Insulin Delivery," *N. Engl. J. Med.*, 321: 574-579 (1989).
Sawai et al., "Direct Production of the Fab Fragment Derived From the Sperm Immobilizing Antibody Using Polymerase Chain Reaction and cDNA Expression Vectors," *Am. J. Reprod. Immunol.*, 34: 26-34 (1995).
Scehnet et al., "Inhibition of Dll4-mediated signaling induces proliferation of immature vessels and results in poor tissue perfusion," *Blood*, 109(11): 4753-4760 (2007).
Schier et al., "Identification of functional and structural amino-acid residues by parsimonious mutagenesis," *Gene*, 169: 147-155 (1995).
Sefton, M.V., "Implantable Pumps," *CRC Crit. Rev. Biomed. Eng.*, 14(3): 201-240 (1987).
Seligmann et al., "Immunochemical Study of a Human Myeloma IgG1 Half Molecule," *Ann. Immunol.*, 129 C:855-870 (1978).
Sewell et al., "$DAB_{486}$IL-2 fusion toxin in refractory rheumatoid arthritis," *Arthritis Rheum.*, 36(9): 1223-1233 (Sep. 1993).
Shalaby et al., "Development of Humanized Bispecific Antibodies Reactive with Cytotoxic Lymphocytes and Tumor Cells Overexpressing the HER2 Protooncogene," *J. Exp. Med.*, 175: 217-225 (1992).
Shapiro et al., "DNA Target Motifs of Somatic Mutagenesis in Antibody Genes," *Crit. Rev. Immunol.*, 22(3):183-200 (2002).
Shepherd et al., "Novel 'inflammatory plague' pathology in presenilin-1 Alzheimer's disease," *Neuropathol. Appl. Neurobiol.*, 31: 503-511 (2005).
Shields et al., "Lack of Fucose on Human IgG1 N-Linked Oligosaccharide Improves Binding to Human FcγRIII and Antibody-dependent Cellular Toxicity," *J. Biol. Chem.*, 277(30): 26733-26740 (2002).
Shu et al., "Secretion of a single-gene-encoded immunoglobulin from myeloma cells," *Proc. Natl. Acad. Sci. USA*, 90: 7995-7999 (1993).
Shutter et al., "Dll4, a novel Notch ligand expressed in arterial endothelium," *Genes Dev.*, 14(11): 1313-1318 (2000).
Skerra et al., "Assembly of a Functional Immunoglobulin $F_v$ Fragment in *Escherichia coli*," *Science*, 240: 1038-1041 (1988).
Smith and Morrison, "Recombinant Polymeric IgG: An Approach to Engineering More Potent Antibodies," *Bio/Technology*, 12: 683-688 (1994).
Snibson et al., "Airway remodelling and inflammation in sheep lungs after chronic airway challenge with house dust mite," *Clin. Exp. Allergy*, 35: 146-152 (2005).
Soloman, B., "Alzheimer's Disease and Immunotherapy," *Curr. Alzheimer. Res.*, 1: 149-163 (2004).
Song et al., "Antibody Mediated Lung Targeting of Long-Circulating Emulsions," *PDA J. Pharm. Sci. Technol.*, 50: 372-377 (1996).
Staerz et al., "Hybrid antibodies can target sites for attack by T cells," *Nature*, 314: 628-631 (1985).
Stancovski et al., "Mechanistic aspects of the opposing effects of monoclonal antibodies to the ERBB2 receptor on tumor growth," *Proc. Natl. Acad. Sci. USA*, 88: 8691-8695 (1991).

(56) References Cited

OTHER PUBLICATIONS

Steffen et al., "Basic studies on enzyme therapy of immune complex diseases" *Wien Klin. Wochenschr.*, 97(8): 376-385 (1985) (Abstract only) (1 page).
Steinman et al., "Virtues and pitfalls of EAE for the development of therapies for multiple sclerosis," *Trends Immunol.*, 26(11): 565-571 (2005).
Stickler et al., "CD4+ T-cell epitope determination using unexposed human donor peripheral blood mononuclear cells," *J. Immunotherapy*, 23: 654-660 (2000).
Stolk et al., "Are severe non-hematologic side-effects on azathioprine treatment caused by altered purine enzyme activities?" (Abstract No. 1522), *Arthritis Rheum.*, 39(9 Suppl.): S281 (1996) (1 page).
Streppel et al., "Focal application of neutralizing antibodies to soluble neurotrophic factors reduces collateral axonal branching after peripheral nerve lesion," *Eur. J. Neurosci.*, 15(8): 327-1342 (2002).
Studnicka et al., "Human-engineered monoclonal antibodies retain full specific binding activity by preserving non-CDR complementarity-modulating residues," *Protein Eng.*, 7(6): 805-814 (1994).
Suchting et al., "The Notch ligand Delta-like 4 negatively regulates endothelial tip cell formation and vessel branching," *Proc. Natl. Acad. Sci. USA*, 104(9): 3225-3230 (2007).
Taiwan Patent Application No. 095130565: Taiwan Patent Office Search Report, dated Apr. 24, 2009.
Taylor et al., "A transgenic mouse that expresses a diversity of human sequence heavy and light chain immunoglobulins," *Nucl. Acids Res.*, 20: 6287-6295 (1992).
Teng et al., "Nogo Signaling and Non-Physical Injury-Induced Nervous System Pathology," *J. Neuroscience Research*, 79: 273-278 (2005).
Thies et al., "Folding and Association of the Antibody Domain $C_H3$: Prolyl Isomerization Preceeds Dimerization," *J. Mol. Biol.*, 293: 67-79 (1999).
Tol et al., "Chemotherapy, Bevacizumab, and Cetuximab in Metastatic Colorectal Cancer," *N. Engl. J. Med.*, 360(6): 563-572 (2009).
Tolstoshev, P., "Gene Therapy, Concepts, Current Trials and Future Directions," *Ann. Rev. Pharmacol. Toxicol.*, 32: 573-596 (1993).
Tuohy et al., "Spontaneous Regression of Primary Autoreactivity during Chronic Progression of Experimental Autoimmune Encephalomyelitis and Multiple Sclerosis," *J. Exp. Med.*, 189(7): 1033-1042 (1999).
Umaña et al., "Engineered glycoforms of an antineuroblastoma IgG1 with optimized antibody-dependent cellular cytotoxic activity," *Nature Biotechnol.*, 17: 176-180 (1999).
Urlaub et al., "Isolation of Chinese hamster cell mutants deficient in dihydrofolate reductase activity," *Proc. Natl. Acad. Sci. USA*, 77: 4216-4220 (1980).
U.S. Appl. No. 12/431,460, filed Apr. 28, 2009 by Ghayur et al.: Non-Final Office Action, Mar. 16, 2011.
U.S. Appl. No. 12/431,460, filed Apr. 28, 2009 by Ghayur et al.: Final Office Action, Nov. 2, 2011.
U.S. Appl. No. 12/477,668, filed Jun. 3, 2009 by Ghayur et al.: Non-Final Office Action, Sep. 8, 2011.
U.S. Appl. No. 12/477,668, filed Jun. 3, 2009 by Ghayur et al.: Final Office Action, May 3, 2012.
U.S. Appl. No. 12/477,711, filed Jun. 3, 2009 by Ghayur et al.: Non-Final Office Action, Aug. 11, 2011.
U.S. Appl. No. 12/477,711, filed Jun. 3, 2009 by Ghayur et al.: Final Office Action, Dec. 30, 2011.
U.S. Appl. No. 12/499,652, filed Jul. 8, 2009 by Ghayur et al.: Non-Final Office Action, May 10, 2011.
U.S. Appl. No. 12/499,652, filed Jul. 8, 2009 by Ghayur et al.: Final Office Action, Nov. 3, 2011.
U.S. Appl. No. 12/605,094, filed Oct. 23, 2009 by Ghayur et al.: Non-Final Office Action, Jun. 29, 2011.
U.S. Appl. No. 12/605,094, filed Oct. 23, 2009 by Ghayur et al.: Final Office Action, Nov. 30, 2011.
U.S. Appl. No. 12/631,483, filed Dec. 4, 2009 by Jakob et al.: Non-Final Office Action, Nov. 23, 2011.
U.S. Appl. No. 12/631,483, filed Dec. 4, 2009 by Jakob et al.: Final Office Action, Jul. 6, 2012.
U.S. Appl. No. 12/771,871, filed Apr. 30, 2010 by Ghayur et al.: Non-Final Office Action, May 16, 2012.
U.S. Appl. No. 12/771,874, filed Apr. 30, 2010 by Ghayur et al.: Non-Final Office Action, Sep. 7, 2012.
U.S. Appl. No. 12/771,874, filed Apr. 30, 2010 by Ghayur et al.: Non-Final Office Action, Apr. 18, 2013.
U.S. Appl. No. 12/771,874, filed Apr. 30, 2010 by Ghayur et al.: Final Office Action, Nov. 12, 2013.
U.S. Appl. No. 12/873,926, filed Sep. 1, 2010 by Ghayur et al.: Non-Final Office Action, Aug. 28, 2012.
U.S. Appl. No. 12/873,926, filed Sep. 1, 2010 by Ghayur et al.: Final Office Action, Mar. 12, 2013.
U.S. Appl. No. 12/905,474, filed Oct. 15, 2010 by Ghayur et al.: Non-Final Office Action, May 29, 2013.
U.S. Appl. No. 13/167,323, filed Jun. 23, 2011 by Ghayur et al.: Non-Final Office Action, Jun. 4, 2013.
U.S. Appl. No. 13/167,323, filed Jun. 23, 2011 by Ghayur et al.: Final Office Action, Nov. 20, 2013.
U.S. Appl. No. 13/196,138, filed Aug. 2, 2011 by Ghayur et al.: Non-Final Office Action, Nov. 27, 2012.
U.S. Appl. No. 13/217,937, filed Aug. 25, 2011 by Ghayur et al.: Non-Final Office Action, Sep. 6, 2012.
U.S. Appl. No. 13/217,937, filed Aug. 25, 2011 by Ghayur et al.: Final Office Action, Mar. 20, 2013.
U.S. Appl. No. 13/286,707, filed Nov. 1, 2011 by Ghayur et al.: Non-Final Office Action, Feb. 25, 2013.
U.S. Appl. No. 13/286,707, filed Nov. 1, 2011 by Ghayur et al.: Final Office Action, Jul. 17, 2013.
Vaccaro et al., "Divergent activities of an engineered antibody in murine and human systems have implications for therapeutic antibodies," *Proc. Natl. Acad. Sci. USA*, 103: 18709-18714 (2006).
Vajdos et al., "Comprehensive functional maps of the antigen-binding site of an anti-ErbB2 antibody obtained with shotgun scanning mutagenesis," *J. Mol. Biol.*, 320: 415-428 (2002).
Verhoeyen et al., "Reshaping Human Antibodies: Grafting an Antilysozyme Activity," *Science*, 239: 1534-1536 (1988).
Voet et al. (Eds.), *Biochemistry*. John Wiley & Sons, Inc., 1999; p. 1100.
Voller et al., "Enzyme immunoassays with special reference to ELISA techniques," *J. Clin. Pathol.*, 31:507-520 (1978).
Von Mehren et al., "Monoclonal Antibody Therapy for Cancer," *Ann. Rev. Med.*, 54: 343-369 (2003).
Wallick et al., "Glycosylation of a $V_H$ Residue of a Monoclonal Antibody Against α(1-6) Dextran Increases Its Affinity for Antigen," *J. Exp. Med.*, 168: 1099-1109 (1988).
Wang et al., "Antibody Structure, Instability, and Formulation," *J. Pharm. Sci.*, 96(1): 1-26 (2007).
Ward et al., "Binding activities of a repertoire of single immunoglobulin variable domains secreted from *Escheria coli*," *Nature*, 341: 544-546 (1989).
West Jr. et al., "Crystal Structure and Immunoglobulin G Binding Properties of the Human Major Histocompatibility Complex-Related Fc Receptor," *Biochemistry*, 39: 9698-9708 (2000).
Wileman et al., "Association between Subunit Ectodomains Promote T Cell Antigen Receptor Assembly and Protect against Degradation in the ER," *J. Cell Biol.*, 122(1): 67-78 (1993).
Wing et al., "Ex-vivo whole blood cultures for predicting cytokine-release syndrome: Dependence on target antigen and antibody isotype," *Therapeutic Immunol.*, 2(4): 183-190 (1995).
Wooldridge et al., "Tricks with tetramers: How to get the most from multimeric peptide-MHC," *Immunology*, 126: 147-164 (2009).
Wright et al., "Antibody variable region glycosylation: Position effects on antigen binding and carbohydrate structure," *EMBO J.*, 10(10): 2717-2723 (1991).
Wu and Grainger, "Drug/device combinations for local drug therapies and infection prophylaxis," *Biomaterials*, 27: 2450-2467 (2006).
Wu and Wu, "Delivery systems for gene therapy," *Biotherapy*, 3: 87-95 (1991).
Wu and Wu, "Receptor-mediated in Vitro Gene Transformation by a Soluble DNA Carrier System," *J. Biol. Chem.*, 262(10): 4429-4432 (1987).

(56) References Cited

OTHER PUBLICATIONS

Wu et al., "Humanization of a murine monoclonal antibody by simultaneous optimization of framework and CDR residues," *J. Mol. Biol.*, 294: 151-162 (1999).
Wu et al., "IL-18 receptor β-induced changes in the presentation of IL-18 binding sites affect ligand binding and signal transduction," *J. Immunol.*, 170: 5571-5577 (2003).
Wu et al., "Simultaneous targeting of multiple disease mediators by a dual-variable-domain immunoglobulin," *Nature Biotechnol.*, 25(11): 1290-1297 (2007).
Wu et al., "Simultaneous targeting of multiple disease mediators by a dual-variable-domain immunoglobulin," *Nature Biotechnology* (advance online publication, http://www.nature.com/naturebiotechnology) pp. 1-8 (published online Oct. 14, 2007).
Wu et al., "Tumor localization of anti-CEA single-chain Fvs: Improved targeting by non-covalent dimers," *Immunotechnology*, 2(1): 21-36 (1996).
Wu et al., "Molecular construction and optimization of anti-human IL-1α/β dual variable domain immunoglobulin (DVD-Ig™) molecules," *mAbs*, 1(4): 339-347 (2009).
Wu et al., "Generation and Characterization of a Dual Variable Domain Immunoglobulin (DVD-Ig™) Molecule," in *Antibody Engineering*, vol. 2. R. Kontermann and S. Dübel (Eds.), Springer-Verlag, 2010; pp. 239-250.
Wurm, F.M., "Production of recombinant protein therapeutics in cultivated mammalian cells," *Nature Biotechnol.*, 22(11): 1393-1398 (2004).
Xu et al., "Recombinant DNA vaccine encoding multiple domains related to inhibition of neurite outgrowth: A potential strategy for axonal regeneration," *J. Neurochem.*, 91: 1018-1023 (2004).
Yan et al., "Delta-like 4/Notch Signaling and Its Therapeutic Implications," *Clin. Cancer Res.*, 13:7243-7246 (2007).
Yelton et al., "Affinity Maturation of the BR96 Anti-Carcinoma Antibody by Codon-Based Mutagenesis," *J. Immunol.*, 155: 1994-2004 (1995).
Yonehara et al., "Involvement of apoptosis antigen Fas in clonal deletion of human thymocytes," *Int. Immunol.*, 6(12): 1849-1856 (1994).
Zapata et al., "Engineering linear F(ab')$_2$ fragments for efficient production in *Escherichia coli* and enhanced antiproliferative activity," *Protein Eng.*, 8(10): 1057-1062 (1995).
Zhang et al., "Inhibition of Cyclooxygenase-2 Rapidly Reverses Inflammatory Hyperalgesia and Prostaglandin E$_2$ Production," *J. Pharmacol. Exp. Ther.*, 283(3): 1069-1075 (1997).
Zola et al., "CD Molecules 2005: Human cell differentiation molecules," *Blood*, 106: 3123-3126 (2005).
Zuo et al., "An efficient route to the production of an IgG-like bispecific antibody," *Protein Eng.*, 13(5): 361-367 (2000).
Arimura et al., "Prevention of Allergic Inflammation by a Novel Prostaglandin Receptor Antagonist, S-5751," *J. Pharmacol. Exper. Therapeut.*, 298(2): 411-419 (2001).
Aroonrerk et al., "A sensitive direct ELISA for detection of prostaglandin E2," *J. Immunoassay & Immunochem.*, 28:319-330 (2007).
Ayoub et al., "Preferential Formation of MT1/MT2 Melatonin Receptor Heterodimers with Distinct Ligand Interaction Properties Compared with MT2 Homodimers," *Mol. Pharmacol.*, 66(2): 312-321 (2004).
Dahesia et al., "The Interleukin 1β Pathway in the Pathogenesis of Osteoarthritis," *J. Rheumatol.*, 35(12):2306-2312 (2008).
European Patent Application No. 06813554.0: Written Submission in Preparation to Oral Proceedings, dated Jan. 23, 2015 (100 pages).
European Patent Application No. 06813554.0: Minutes of Oral Proceedings, dated Jan. 29, 2015 (7 pages).
European Patent Application No. 06813554.0: Reply to Minutes of Oral Proceedings, dated Jan. 29, 2015 (1 page).
European Patent Application No. 11815172.9: Partial Supplementary European Search Report, dated Nov. 12, 2014 (10 pages).

European Patent Application No. 11815172.9: Supplementary European Search Report and Search Opinion, dated Jan. 21, 2015 (16 pages).
European Patent Application No. 14176206.2 by AbbVie Inc.: Extended European Search Report and Opinion, dated Nov. 12, 2014 (7 pages).
Garber, K, "Anti-IL-17 mAbs herald new options in psoriasis," *Nat. Biotechnol.*, 30(6): 475-477 (2012).
Grothey and Galanis, "Targeting angiogenesis: progress with anti-VEGF treatment with large molecules," *Nat. Rev. Clin. Oncol.*, 6:507-518 (2009).
Hindawi et al., "The development and application of a direct radioimmunoassay for prostaglandin E2 utilising a α-labelled ligand," *Prostaglandins, Leukotrienes and Medicine*, 18: 81-94 (1985).
Honegger et al., "Yet Another Numbering Scheme for Immunoglobulin Variable Domains: An Automatic Modeling and Analysis Tool," *J. Mol. Biol.*, 309(3): 657-670 (2001).
Honorati et al., "Contribution of interleukin 17 to human cartilage degradation and synovial inflammation in osteoarthritis," *Osteoarthritis and Cartilage*, 10: 799-807 (2002).
International Patent Application No. PCT/US2009/049953: International Search Report and Written Opinion, mailed Oct. 29, 2009 (10 pages).
International Patent Application No. PCT/US2014/028618: Invitation to Pay Additional Fees and Communication Relating to the Results of the Partial International Search, dated Aug. 13, 2014 (8 pages).
International Patent Application No. PCT/US2014/028618: International Search Report and Written Opinion, Oct. 28, 2014 (25 pages).
International Patent Application No. PCT/US2014/028646: International Search Report and Written Opinion, Oct. 17, 2014 (18 pages).
International Patent Application No. PCT/US2014/028646 Invitation to Pay Additional Fees and Communication Relating to the Results of the Partial International Search, dated Aug. 14, 2014 (10 pages).
Jakob et al., "Structure reveals function of the dual variable domain immunoglobulin (DVD-Ig™) molecule," *mAbs*, 5(3): 358-363 (2013).
Jotanovic et al., "Role of Interleukin-1 Inhibitors in Osteoarthritis," *Drugs Aging*, 29(5): 343-358 (2012).
Kou et al., "A bispecific antibody effectively inhibits tumor growth and metastasis by simultaneous blocking vascular endothelial growth factor A and osteopontin," *Cancer Lett.*, 299: 130-136 (2010).
Li et al., "Bispecific Antibody to ErbB2 Overcomes Trastuzumab Resistance through Comprehensive Blockade of ErbB2 Heterodimerization," *Cancer Res.*, 73(21): 6471-6483 (2013).
Monnet et al., "Association between the IL-1 family gene cluster and spondyloarthritis," *Ann. Rheum. Dis.*, 71:885-890 (2012).
Neuman et al., "An ELISA for PGE2 utilizing monoclonal antibody," *J. Immunoassay & Immunochem.*, 9(2):159-177 (1988).
Qi et al, "A bispecific antibody against IL-1β and IL-17A is beneficial for experimental rheumatoid arthritis," *Internat'l. Immunopharm.*, 14:770-778 (2012).
Quesada et al., "Do Not Say Ever Never More: The Ins and Outs of Antiangiogenic Therapies," *Curr. Pharmaceut. Des.*, 16: 3932-3957 (2010).
Rahman et al., "Association between the interleukin-1 family gene cluster and psoriatic arthritis," *Arthritis Rheum.*, 54(7): 2321-2325 (2006).
Reichert, J.M., "Bispecific antibodies and ADCs. Once and future kings?" *mAbs*, 3(4): 329-330 (2011).
Sainson et al., "Anti-DII4 therapy: can we block tumour growth by increasing angiogenesis?" *TRENDS Mol. Med.*, 13(9): 389-395 (2007).
Tan et al., "A bispecific antibody against two different epitopes on hepatitis B surface antigen has potent hepatitis B virus neutralizing activity," *mAbs*, 5(6): 946-955 (2013).
Torisu et al., "Discovery of a new class of potent, selective, and orally active prostaglandin D$_2$ receptor antagonists," *Bioorg. Med. Chem.*, 5361-5378 (2004).

(56) References Cited

OTHER PUBLICATIONS

U.S. Appl. No. 12/431,460, filed Apr. 28, 2009 by Ghayur et al.: Notice of Allowance, Jan. 8, 2015.

U.S. Appl. No. 12/477,711, filed Jun. 3, 2009 by Ghayur et al.: Notice of Allowance, Jan. 27, 2015.

U.S. Appl. No. 13/178,641, filed Jul. 8, 2011 by Ghayur et al.: Non-Final Office Action, Dec. 17, 2014.

U.S. Appl. No. 14/068,976, filed Oct. 21, 2013 by Gu et al.: Non-Final Office Action, Feb. 4, 2015.

Yu et al., "Boosting Brain Uptake of a Therapeutic Antibody by Reducing its Affinity for a Transcytosis Target," *Sci. Transl. Med.*, 3(84):84ra44, 8 pages (2011).

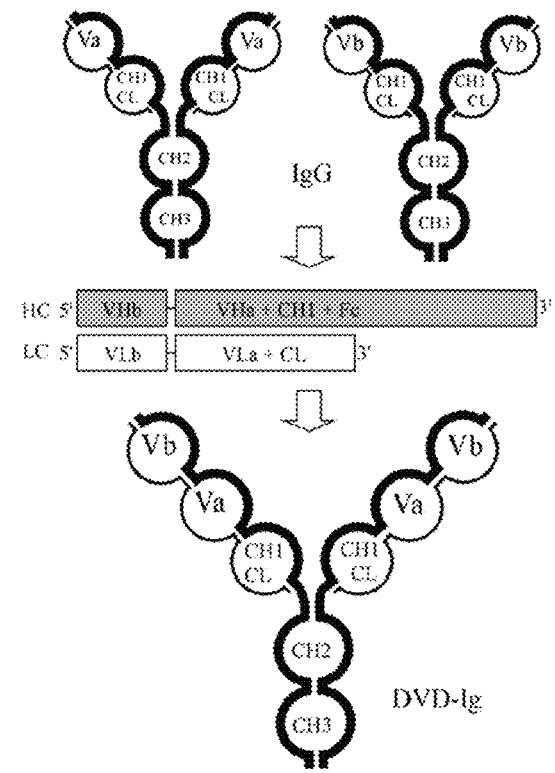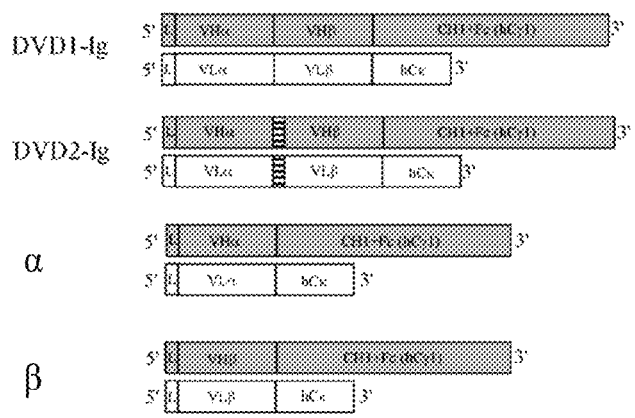

SEQUENCE LISTING

<160> NUMBER OF SEQ ID NOS: 76

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Thr Lys Gly Pro Ser Val Phe Pro Leu Ala Pro
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ser Thr Lys Gly Pro
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Gly Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser Gly Gly Gly Gly
1               5                   10

<210> SEQ ID NO 6
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Thr Val Ala Ala Pro Ser Val Phe Ile Phe Pro Pro
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Val Ala Ala Pro
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Ser Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Ser Gly Gly Gly Gly Ser Gly
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Gly Gly Gly Gly Ser Gly Gly Gly Gly Ser
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ser Gly Gly
1               5
```

```
<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Gly Gly Gly Gly Ser Gly Gly Gly Ser
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Lys Thr Thr Pro Lys Leu Glu Glu Gly Glu Phe Ser Glu Ala Arg
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Thr Thr Pro Lys Leu Glu Glu Gly Glu Phe Ser Glu Ala Arg
1               5                   10                  15

Val

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Lys Thr Thr Pro Lys Leu Gly Gly
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ala Lys Thr Thr Pro Lys Leu Gly Gly
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 17

Ser Ala Lys Thr Thr Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Asp Ala Ala Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Asp Ala Ala Pro Thr Val Ser
1               5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Asp Ala Ala Ala Ala Gly Gly Pro Gly Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Asp Ala Ala Ala Ala
1               5

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ala Lys Thr Thr Pro Lys Leu Glu Glu Gly Glu Phe Ser Glu Ala
1               5                   10                  15

Arg Val
```

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Asp Ala Ala Pro
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Asp Ala Ala Pro Thr Val Ser Ile Phe Pro Pro
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Val Ala Ala Pro
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Val Ala Ala Pro Ser Val Phe Ile Phe Pro Pro
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Pro Lys Ala Ala Pro
1               5

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 28

Gln Pro Lys Ala Ala Pro Ser Val Thr Leu Phe Pro Pro
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Lys Thr Thr Pro Pro
1               5

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Lys Thr Thr Pro Pro Ser Val Thr Pro Leu Ala Pro
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Lys Thr Thr Ala Pro
1               5

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Lys Thr Thr Ala Pro Ser Val Tyr Pro Leu Ala Pro
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser Gly Gly Gly Ser Gly Gly Gly Gly Ser
1               5                   10                  15

<210> SEQ ID NO 34
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 34

Gly Glu Asn Lys Val Glu Tyr Ala Pro Ala Leu Met Ala Leu Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Pro Ala Lys Glu Leu Thr Pro Leu Lys Glu Ala Lys Val Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly His Glu Ala Ala Val Met Gln Val Gln Tyr Pro Ala Ser
1               5                   10                  15

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
```

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Thr Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                85                  90                  95

Thr Phe Gly Gln Gly Thr Lys Leu Glu Ile Lys Arg
            100                 105

<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120

<210> SEQ ID NO 42
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg
            100                 105

<210> SEQ ID NO 43
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Thr Leu Arg Glu Ser Gly Pro Ala Leu Val Lys Pro Thr Gln
 1               5                  10                  15

Thr Leu Thr Leu Thr Cys Thr Ala Ser Gly Tyr Thr Phe Thr Asn Tyr
                20                  25                  30

Gly Met Asn Trp Val Arg Gln Pro Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Gln Ala Val
 65                  70                  75                  80

Leu Thr Met Thr Asn Met Asp Pro Val Asp Thr Ala Thr Tyr Tyr Cys
                 85                  90                  95

Ala Lys Tyr Pro His Tyr Tyr Gly Ser Ser His Trp Tyr Phe Asp Val
            100                 105                 110

```
Trp Gly Gln Gly Thr Thr Val Thr Val Ser Ser
        115                 120

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Ser Ala Ser Gln Asp Ile Ser Asn Tyr
            20                  25                  30

Leu Asn Trp Tyr Gln Gln Lys Pro Gly Gln Ala Pro Lys Val Leu Ile
        35                  40                  45

Tyr Phe Thr Ser Ser Leu His Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Thr Val Pro Trp
                85                  90                  95

Thr Phe Gly Gly Gly Thr Lys Val Glu Ile Lys Arg
            100                 105

<210> SEQ ID NO 45
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Thr Glu Val Lys Lys Pro Gly Glu
1               5                   10                  15

Ser Leu Lys Ile Ser Cys Lys Ala Ser Gly Tyr Thr Phe Thr Asn Tyr
            20                  25                  30

Gly Met Asn Trp Val Arg Gln Met Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Gln Phe Thr Phe Ser Leu Asp Thr Ser Phe Ser Thr Ala Phe
65                  70                  75                  80

Leu Gln Trp Ser Ser Leu Lys Ala Ser Asp Thr Ala Met Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Met Val Thr Val Ser Ser
        115                 120

<210> SEQ ID NO 46
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

Glu Ile Val Met Thr Gln Ser Pro Ala Thr Leu Ser Val Ser Pro Gly
1               5                   10                  15

Glu Arg Ala Thr Leu Ser Cys Ser Ala Ser Gln Asp Ile Ser Asn Tyr
            20                  25                  30

Leu Asn Trp Tyr Gln Gln Lys Pro Gly Gln Ala Pro Arg Val Leu Ile
        35                  40                  45

Tyr Phe Thr Ser Ser Leu His Ser Asp Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Thr Val Pro Trp
                85                  90                  95

Thr Phe Gly Gln Gly Thr Arg Leu Glu Ile Lys Arg
            100                 105

<210> SEQ ID NO 47
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Met Thr Gln Ser Pro Gly Thr Leu Ser Leu Ser Pro Gly
1               5                   10                  15

Glu Arg Ala Thr Leu Ser Cys Ser Ala Ser Gln Asp Ile Ser Asn Tyr
            20                  25                  30

Leu Asn Trp Tyr Gln Gln Lys Pro Gly Gln Ala Pro Arg Val Leu Ile
        35                  40                  45

Tyr Phe Thr Ser Ser Leu His Ser Gly Val Pro Asp Arg Phe Ser Gly
            50                  55                  60

Ser Gly Ser Gly Thr Asp Phe Thr Leu Thr Ile Ser Arg Leu Glu Pro
65                  70                  75                  80

Glu Asp Phe Ala Val Phe Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 49
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ala Lys Ser Ser Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 50
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 51
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Ala Asn
1               5                   10                  15

Ser Leu Lys Leu Ser Cys Ala Ala Ser Gly Tyr Thr Phe Thr Asn Tyr
            20                  25                  30

Gly Met Asn Trp Val Arg Gln Ser Pro Lys Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ala Lys Ser Thr Ala Tyr
65                  70                  75                  80

Leu Gln Met Asp Ser Leu Arg Ser Glu Asp Thr Ala Thr Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Val Leu Val Thr Val Ser Ser
        115                 120

<210> SEQ ID NO 52
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Arg Met Thr Gln Ser Pro Ala Ser Leu Ser Ala Ser Leu Gly
1               5                   10                  15

Glu Thr Val Asn Ile Glu Cys Ser Ala Ser Gln Asp Ile Ser Asn Tyr
            20                  25                  30

Leu Asn Trp Tyr Gln Gln Lys Pro Gly Lys Ala Pro Gln Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Val Ala Thr Tyr Tyr Cys Gln Gln Tyr Ser Thr Val Pro Trp
                85                  90                  95

Thr Phe Gly Gly Gly Thr Lys Leu Glu Leu Lys Arg
            100                 105

<210> SEQ ID NO 53
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Gln Ser Gly Ala Glu Leu Met Lys Pro Gly Ala

```
                1               5                   10                  15
Ser Val Lys Leu Ser Cys Lys Ala Thr Gly Tyr Thr Phe Thr Asn Tyr
                        20                  25                  30

Gly Met Asn Trp Val Lys Gln Arg Pro Gly His Gly Leu Glu Trp Val
                35                  40                  45

Gly Trp Ile Asn Thr Tyr Thr Gly Glu Pro Thr Tyr Ala Ala Asp Phe
        50                  55                  60

Lys Arg Lys Phe Thr Phe Thr Leu Asp Thr Ser Ser Thr Ala Tyr
65                  70                  75                  80

Ile Gln Leu Ile Ser Leu Thr Thr Glu Asp Ser Ala Ile Tyr Tyr Cys
                        85                  90                  95

Ala Lys Tyr Pro His Tyr Tyr Gly Ser Ser His Trp Tyr Phe Asp Val
                100                 105                 110

Trp Gly Gln Gly Thr Leu Leu Thr Val Ser Ala
            115                 120
```

<210> SEQ ID NO 54
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Leu Met Thr Gln Ser Pro Ala Ile Leu Ser Val Ser Pro Gly
1               5                   10                  15

Glu Arg Val Ser Phe Ser Cys Ser Ala Ser Gln Asp Ile Ser Asn Tyr
                20                  25                  30

Leu Asn Trp Tyr Gln Gln Arg Thr Asn Gly Ala Pro Arg Val Leu Ile
            35                  40                  45

Tyr Phe Thr Ser Ser Leu His Ser Gly Val Pro Ser Arg Phe Ser Gly
        50                  55                  60

Gly Gly Ser Gly Thr Asp Phe Thr Leu Ser Ile Asn Ser Val Glu Ser
65                  70                  75                  80

Glu Asp Ile Ala Asp Tyr Tyr Cys Gln Gln Tyr Ser Thr Val Pro Trp
                85                  90                  95

Thr Phe Gly Ala Gly Thr Lys Leu Glu Leu Lys Arg
                100                 105
```

<210> SEQ ID NO 55
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
                20                  25                  30

Pro Met Ala Trp Val Arg Gln Ala Pro Gly Lys Gly Leu Glu Trp Val
            35                  40                  45

Ala Thr Ile Ser Ser Ser Asp Gly Thr Thr Tyr Tyr Arg Asp Ser Val
        50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Gly Tyr Tyr Asn Ser Pro Phe Ala Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Glu Val Gln Leu Val Glu Ser Gly Gly Leu Val Gln
130                 135                 140

Pro Gly Gly Ser Leu Arg Leu Ser Cys Ala Ala Ser Gly Tyr Thr Phe
145                 150                 155                 160

Thr Asn Tyr Gly Met Asn Trp Val Arg Gln Ala Pro Gly Lys Gly Leu
                165                 170                 175

Glu Trp Val Gly Trp Ile Asn Thr Tyr Thr Gly Glu Pro Thr Tyr Ala
                180                 185                 190

Ala Asp Phe Lys Arg Arg Phe Thr Phe Ser Leu Asp Thr Ser Lys Ser
                195                 200                 205

Thr Ala Tyr Leu Gln Met Asn Ser Leu Arg Ala Glu Asp Thr Ala Val
                210                 215                 220

Tyr Tyr Cys Ala Lys Tyr Pro His Tyr Tyr Gly Ser Ser His Trp Tyr
225                 230                 235                 240

Phe Asp Val Trp Gly Gln Gly Thr Leu Val Thr Val Ser Ser
                245                 250

<210> SEQ ID NO 56
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
                20                  25                  30

Pro Met Ala Trp Val Arg Gln Ala Pro Gly Lys Gly Leu Glu Trp Val
                35                  40                  45

Ala Thr Ile Ser Ser Ser Asp Gly Thr Thr Tyr Tyr Arg Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Gly Tyr Tyr Asn Ser Pro Phe Ala Tyr Trp Gly Gln Gly Thr
                100                 105                 110

Leu Val Thr Val Ser Ser Ala Ser Thr Lys Gly Pro Glu Val Gln Leu
                115                 120                 125

Val Glu Ser Gly Gly Gly Leu Val Gln Pro Gly Gly Ser Leu Arg Leu
130                 135                 140

Ser Cys Ala Ala Ser Gly Tyr Thr Phe Thr Asn Tyr Gly Met Asn Trp
145                 150                 155                 160

Val Arg Gln Ala Pro Gly Lys Gly Leu Glu Trp Val Gly Trp Ile Asn
                165                 170                 175
```

Thr Tyr Thr Gly Glu Pro Thr Tyr Ala Ala Asp Phe Lys Arg Arg Phe
            180                 185                 190

Thr Phe Ser Leu Asp Thr Ser Lys Ser Thr Ala Tyr Leu Gln Met Asn
            195                 200                 205

Ser Leu Arg Ala Glu Asp Thr Ala Val Tyr Tyr Cys Ala Lys Tyr Pro
        210                 215                 220

His Tyr Tyr Gly Ser Ser His Trp Tyr Phe Asp Val Trp Gly Gln Gly
225                 230                 235                 240

Thr Leu Val Thr Val Ser Ser
            245

<210> SEQ ID NO 57
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Tyr Thr Phe Thr Asn Tyr
145                 150                 155                 160

Gly Met Asn Trp Val Arg Gln Ala Pro Gly Lys Gly Leu Glu Trp Val
                165                 170                 175

Gly Trp Ile Asn Thr Tyr Thr Gly Glu Pro Thr Tyr Ala Ala Asp Phe
            180                 185                 190

Lys Arg Arg Phe Thr Phe Ser Leu Asp Thr Ser Lys Ser Thr Ala Tyr
        195                 200                 205

Leu Gln Met Asn Ser Leu Arg Ala Glu Asp Thr Ala Val Tyr Tyr Cys
    210                 215                 220

Ala Lys Tyr Pro His Tyr Tyr Gly Ser Ser His Trp Tyr Phe Asp Val
225                 230                 235                 240

Trp Gly Gln Gly Thr Leu Val Thr Val Ser Ser
                245                 250

<210> SEQ ID NO 58
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Glu Val Gln Leu Val Glu Ser Gly Gly Gly Leu Val
    130                 135                 140

Gln Pro Gly Gly Ser Leu Arg Leu Ser Cys Ala Ala Ser Gly Tyr Thr
145                 150                 155                 160

Phe Thr Asn Tyr Gly Met Asn Trp Val Arg Gln Ala Pro Gly Lys Gly
                165                 170                 175

Leu Glu Trp Val Gly Trp Ile Asn Thr Tyr Thr Gly Glu Pro Thr Tyr
            180                 185                 190

Ala Ala Asp Phe Lys Arg Arg Phe Thr Phe Ser Leu Asp Thr Ser Lys
        195                 200                 205

Ser Thr Ala Tyr Leu Gln Met Asn Ser Leu Arg Ala Glu Asp Thr Ala
    210                 215                 220

Val Tyr Tyr Cys Ala Lys Tyr Pro His Tyr Tyr Gly Ser Ser His Trp
225                 230                 235                 240

Tyr Phe Asp Val Trp Gly Gln Gly Thr Leu Val Thr Val Ser Ser
                245                 250                 255
```

<210> SEQ ID NO 59
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Glu Val Gln Leu Val Glu Ser Gly
    130                 135                 140

Gly Gly Leu Val Gln Pro Gly Gly Ser Leu Arg Leu Ser Cys Ala Ala
145                 150                 155                 160

Ser Gly Phe Thr Phe Ser Asn Phe Pro Met Ala Trp Val Arg Gln Ala
                165                 170                 175

Pro Gly Lys Gly Leu Glu Trp Val Ala Thr Ile Ser Ser Ser Asp Gly
            180                 185                 190

Thr Thr Tyr Tyr Arg Asp Ser Val Lys Gly Arg Phe Thr Ile Ser Arg
        195                 200                 205

Asp Asn Ala Lys Asn Ser Leu Tyr Leu Gln Met Asn Ser Leu Arg Ala
    210                 215                 220

Glu Asp Thr Ala Val Tyr Tyr Cys Ala Arg Gly Tyr Tyr Asn Ser Pro
225                 230                 235                 240

Phe Ala Tyr Trp Gly Gln Gly Thr Leu Val Thr Val Ser Ser
                245                 250

<210> SEQ ID NO 60
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Asn
145                 150                 155                 160

Phe Pro Met Ala Trp Val Arg Gln Ala Pro Gly Lys Gly Leu Glu Trp
                165                 170                 175

Val Ala Thr Ile Ser Ser Ser Asp Gly Thr Thr Tyr Tyr Arg Asp Ser

```
                    180                 185                 190
Val Lys Gly Arg Phe Thr Ile Ser Arg Asp Asn Ala Lys Asn Ser Leu
            195                 200                 205

Tyr Leu Gln Met Asn Ser Leu Arg Ala Glu Asp Thr Ala Val Tyr Tyr
        210                 215                 220

Cys Ala Arg Gly Tyr Tyr Asn Ser Pro Phe Ala Tyr Trp Gly Gln Gly
225                 230                 235                 240

Thr Leu Val Thr Val Ser Ser
            245

<210> SEQ ID NO 61
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Gly Gly Gly Gly Ser
        115                 120                 125

Gly Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Asn
145                 150                 155                 160

Phe Pro Met Ala Trp Val Arg Gln Ala Pro Gly Lys Gly Leu Glu Trp
                165                 170                 175

Val Ala Thr Ile Ser Ser Ser Asp Gly Thr Thr Tyr Tyr Arg Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Gly Tyr Tyr Asn Ser Pro Phe Ala Tyr Trp Gly Gln Gly
225                 230                 235                 240

Thr Leu Val Thr Val Ser Ser
            245

<210> SEQ ID NO 62
<211> LENGTH: 251
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 62

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Thr | Phe | Thr | Asn | Tyr |
| | | | 20 | | | | | 25 | | | | | 30 | | |

| Gly | Met | Asn | Trp | Val | Arg | Gln | Ala | Pro | Gly | Lys | Gly | Leu | Glu | Trp | Val |
| | | 35 | | | | | 40 | | | | | 45 | | | |

| Gly | Trp | Ile | Asn | Thr | Tyr | Thr | Gly | Glu | Pro | Thr | Tyr | Ala | Ala | Asp | Phe |
| 50 | | | | | 55 | | | | | 60 | | | | | |

| Lys | Arg | Arg | Phe | Thr | Phe | Ser | Leu | Asp | Thr | Ser | Lys | Ser | Thr | Ala | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Lys | Tyr | Pro | His | Tyr | Tyr | Gly | Ser | Ser | His | Trp | Tyr | Phe | Asp | Val |
| | | | 100 | | | | | 105 | | | | | 110 | | |

| Trp | Gly | Gln | Gly | Thr | Leu | Val | Thr | Val | Ser | Ser | Gly | Gly | Gly | Gly | Ser |
| | | 115 | | | | | 120 | | | | | 125 | | | |

| Gly | Gly | Gly | Gly | Ser | Glu | Val | Gln | Leu | Val | Glu | Ser | Gly | Gly | Gly | Leu |
| | 130 | | | | | 135 | | | | | 140 | | | | |

| Val | Gln | Pro | Gly | Gly | Ser | Leu | Arg | Leu | Ser | Cys | Ala | Ala | Ser | Gly | Phe |
| 145 | | | | | 150 | | | | | 155 | | | | | 160 |

| Thr | Phe | Ser | Asn | Phe | Pro | Met | Ala | Trp | Val | Arg | Gln | Ala | Pro | Gly | Lys |
| | | | | 165 | | | | | 170 | | | | | 175 | |

| Gly | Leu | Glu | Trp | Val | Ala | Thr | Ile | Ser | Ser | Ser | Asp | Gly | Thr | Thr | Tyr |
| | | | 180 | | | | | 185 | | | | | 190 | | |

| Tyr | Arg | Asp | Ser | Val | Lys | Gly | Arg | Phe | Thr | Ile | Ser | Arg | Asp | Asn | Ala |
| | | 195 | | | | | 200 | | | | | 205 | | | |

| Lys | Asn | Ser | Leu | Tyr | Leu | Gln | Met | Asn | Ser | Leu | Arg | Ala | Glu | Asp | Thr |
| | 210 | | | | | 215 | | | | | 220 | | | | |

| Ala | Val | Tyr | Tyr | Cys | Ala | Arg | Gly | Tyr | Tyr | Asn | Ser | Pro | Phe | Ala | Tyr |
| 225 | | | | | 230 | | | | | 235 | | | | | 240 |

| Trp | Gly | Gln | Gly | Thr | Leu | Val | Thr | Val | Ser | Ser |
| | | | | 245 | | | | | 250 | |

<210> SEQ ID NO 63
<211> LENGTH: 255
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Thr | Phe | Thr | Asn | Tyr |
| | | | 20 | | | | | 25 | | | | | 30 | | |

| Gly | Met | Asn | Trp | Val | Arg | Gln | Ala | Pro | Gly | Lys | Gly | Leu | Glu | Trp | Val |
| | | 35 | | | | | 40 | | | | | 45 | | | |

| Gly | Trp | Ile | Asn | Thr | Tyr | Thr | Gly | Glu | Pro | Thr | Tyr | Ala | Ala | Asp | Phe |
| 50 | | | | | 55 | | | | | 60 | | | | | |

| Lys | Arg | Arg | Phe | Thr | Phe | Ser | Leu | Asp | Thr | Ser | Lys | Ser | Thr | Ala | Tyr |
| 65 | | | | | 70 | | | | | 75 | | | | | 80 |

```
Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Glu Val Gln Leu Val Glu Ser
            130                 135             140

Gly Gly Gly Leu Val Gln Pro Gly Gly Ser Leu Arg Leu Ser Cys Ala
145                 150                 155                 160

Ala Ser Gly Phe Thr Phe Ser Asn Phe Pro Met Ala Trp Val Arg Gln
            165                 170                 175

Ala Pro Gly Lys Gly Leu Glu Trp Val Ala Thr Ile Ser Ser Ser Asp
            180                 185                 190

Gly Thr Thr Tyr Tyr Arg Asp Ser Val Lys Gly Arg Phe Thr Ile Ser
            195                 200                 205

Arg Asp Asn Ala Lys Asn Ser Leu Tyr Leu Gln Met Asn Ser Leu Arg
210                 215                 220

Ala Glu Asp Thr Ala Val Tyr Tyr Cys Ala Arg Gly Tyr Tyr Asn Ser
225                 230                 235                 240

Pro Phe Ala Tyr Trp Gly Gln Gly Thr Leu Val Thr Val Ser Ser
            245                 250                 255

<210> SEQ ID NO 64
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
            35                  40                  45

Tyr Asp Thr Asn Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Asp Ile Gln Met Thr Gln Ser Pro
            115                 120                 125

Ser Ser Leu Ser Ala Ser Val Gly Asp Arg Val Thr Ile Thr Cys Ser
            130                 135                 140

Ala Ser Gln Asp Ile Ser Asn Tyr Leu Asn Trp Tyr Gln Gln Lys Pro
145                 150                 155                 160

Gly Lys Ala Pro Lys Val Leu Ile Tyr Phe Thr Ser Ser Leu His Ser
            165                 170                 175

Gly Val Pro Ser Arg Phe Ser Gly Ser Gly Ser Gly Thr Asp Phe Thr
            180                 185                 190
```

```
Leu Thr Ile Ser Ser Leu Gln Pro Glu Asp Phe Ala Thr Tyr Tyr Cys
        195                 200                 205

Gln Gln Tyr Ser Thr Val Pro Trp Thr Phe Gly Gly Gly Thr Lys Val
    210                 215                 220

Glu Ile Lys Arg
225

<210> SEQ ID NO 65
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Thr Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Leu Ser Ala Ser Val
        115                 120                 125

Gly Asp Arg Val Thr Ile Thr Cys Ser Ala Ser Gln Asp Ile Ser Asn
    130                 135                 140

Tyr Leu Asn Trp Tyr Gln Gln Lys Pro Gly Lys Ala Pro Lys Val Leu
145                 150                 155                 160

Ile Tyr Phe Thr Ser Ser Leu His Ser Gly Val Pro Ser Arg Phe Ser
                165                 170                 175

Gly Ser Gly Ser Gly Thr Asp Phe Thr Leu Thr Ile Ser Ser Leu Gln
            180                 185                 190

Pro Glu Asp Phe Ala Thr Tyr Tyr Cys Gln Gln Tyr Ser Thr Val Pro
        195                 200                 205

Trp Thr Phe Gly Gln Gly Thr Lys Val Glu Ile Lys Arg
    210                 215                 220

<210> SEQ ID NO 66
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30
```

-continued

```
Leu Ala Trp Tyr Gln Gln Lys Pro Gly Lys Ala Pro Lys Leu Leu Ile
         35                  40                  45

Tyr Asp Thr Asn Asn Leu Ala Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Pro
                 85                  90                  95

Thr Phe Gly Gln Gly Thr Lys Leu Glu Ile Lys Arg Gly Gly Ser Gly
            100                 105                 110

Gly Gly Gly Ser Gly Asp Ile Gln Met Thr Gln Ser Pro Ser Ser Leu
        115                 120                 125

Ser Ala Ser Val Gly Asp Arg Val Thr Ile Thr Cys Ser Ala Ser Gln
130                 135                 140

Asp Ile Ser Asn Tyr Leu Asn Trp Tyr Gln Gln Lys Pro Gly Lys Ala
145                 150                 155                 160

Pro Lys Val Leu Ile Tyr Phe Thr Ser Ser Leu His Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Tyr
        195                 200                 205

Ser Thr Val Pro Trp Thr Phe Gly Gln Gly Thr Lys Val Glu Ile Lys
210                 215                 220

Arg
225

<210> SEQ ID NO 67
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Ile Tyr Ser Asn
             20                  25                  30

Leu Ala Trp Tyr Gln Gln Lys Pro Gly Lys Ala Pro Lys Leu Leu Ile
         35                  40                  45

Tyr Asp Thr Asn Asn Leu Ala Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Pro
                 85                  90                  95

Thr Phe Gly Gln Gly Thr Lys Leu Glu Ile Lys Arg Gly Gly Ser Gly
            100                 105                 110

Gly Gly Gly Ser Gly Gly Gly Ser Asp Ile Gln Met Thr Gln Ser
        115                 120                 125

Pro Ser Ser Leu Ser Ala Ser Val Gly Asp Arg Val Thr Ile Thr Cys
130                 135                 140

Ser Ala Ser Gln Asp Ile Ser Asn Tyr Leu Asn Trp Tyr Gln Gln Lys
```

```
                145                 150                 155                 160
Pro Gly Lys Ala Pro Lys Val Leu Ile Tyr Phe Thr Ser Ser Leu His
                    165                 170                 175

Ser Gly Val Pro Ser Arg Phe Ser Gly Ser Gly Ser Gly Thr Asp Phe
                180                 185                 190

Thr Leu Thr Ile Ser Ser Leu Gln Pro Glu Asp Phe Ala Thr Tyr Tyr
                    195                 200                 205

Cys Gln Gln Tyr Ser Thr Val Pro Trp Thr Phe Gly Gln Gly Thr Lys
            210                 215                 220

Val Glu Ile Lys Arg
225

<210> SEQ ID NO 68
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Asp Ile Gln Met Thr Gln Ser Pro
            115                 120                 125

Ser Ser Leu Ser Ala Ser Val Gly Asp Arg Val Thr Ile Thr Cys Arg
        130                 135                 140

Ala Ser Glu Asp Ile Tyr Ser Asn Leu Ala Trp Tyr Gln Gln Lys Pro
145                 150                 155                 160

Gly Lys Ala Pro Lys Leu Leu Ile Tyr Asp Thr Asn Asn Leu Ala Asp
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Tyr Asn Asn Tyr Pro Pro Thr Phe Gly Gln Gly Thr Lys Leu
    210                 215                 220

Glu Ile Lys Arg
225

<210> SEQ ID NO 69
<211> LENGTH: 221
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Asp Ile Gln Met Thr Gln Ser Pro Ser Ser Leu Ser Ala Ser Val
        115                 120                 125

Gly Asp Arg Val Thr Ile Thr Cys Arg Ala Ser Glu Asp Ile Tyr Ser
130                 135                 140

Asn Leu Ala Trp Tyr Gln Gln Lys Pro Gly Lys Ala Pro Lys Leu Leu
145                 150                 155                 160

Ile Tyr Asp Thr Asn Asn Leu Ala Asp Gly Val Pro Ser Arg Phe Ser
                165                 170                 175

Gly Ser Gly Ser Gly Thr Asp Phe Thr Leu Thr Ile Ser Ser Leu Gln
            180                 185                 190

Pro Glu Asp Phe Ala Thr Tyr Tyr Cys Gln Gln Tyr Asn Asn Tyr Pro
        195                 200                 205

Pro Thr Phe Gly Gln Gly Thr Lys Leu Glu Ile Lys Arg
    210                 215                 220

<210> SEQ ID NO 70
<211> LENGTH: 221
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Gly Gly Ser Gly
            100                 105                 110

```
Gly Asp Ile Gln Met Thr Gln Ser Pro Ser Ser Leu Ser Ala Ser Val
            115                 120                 125

Gly Asp Arg Val Thr Ile Thr Cys Arg Ala Ser Glu Asp Ile Tyr Ser
        130                 135                 140

Asn Leu Ala Trp Tyr Gln Gln Lys Pro Gly Lys Ala Pro Lys Leu Leu
145                 150                 155                 160

Ile Tyr Asp Thr Asn Asn Leu Ala Asp Gly Val Pro Ser Arg Phe Ser
                165                 170                 175

Gly Ser Gly Ser Gly Thr Asp Phe Leu Thr Ile Ser Ser Leu Gln
                180                 185                 190

Pro Glu Asp Phe Ala Thr Tyr Tyr Cys Gln Gln Tyr Asn Asn Tyr Pro
            195                 200                 205

Pro Thr Phe Gly Gln Gly Thr Lys Leu Glu Ile Lys Arg
            210                 215                 220

<210> SEQ ID NO 71
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Gly Gly Ser Gly
            100                 105                 110

Gly Gly Gly Ser Gly Asp Ile Gln Met Thr Gln Ser Pro Ser Ser Leu
        115                 120                 125

Ser Ala Ser Val Gly Asp Arg Val Thr Ile Thr Cys Arg Ala Ser Glu
    130                 135                 140

Asp Ile Tyr Ser Asn Leu Ala Trp Tyr Gln Gln Lys Pro Gly Lys Ala
145                 150                 155                 160

Pro Lys Leu Leu Ile Tyr Asp Thr Asn Asn Leu Ala Asp Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Phe Ala Thr Tyr Tyr Cys Gln Gln Tyr
        195                 200                 205

Asn Asn Tyr Pro Pro Thr Phe Gly Gln Gly Thr Lys Leu Glu Ile Lys
    210                 215                 220

Arg
225

<210> SEQ ID NO 72
```

<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Gly Gly Ser Gly
            100                 105                 110

Gly Gly Gly Ser Gly Gly Gly Ser Asp Ile Gln Met Thr Gln Ser Pro
        115                 120                 125

Ser Ser Leu Ser Ala Ser Val Gly Asp Arg Val Thr Ile Thr Cys Arg
130                 135                 140

Ala Ser Glu Asp Ile Tyr Ser Asn Leu Ala Trp Tyr Gln Gln Lys Pro
145                 150                 155                 160

Gly Lys Ala Pro Lys Leu Leu Ile Tyr Asp Thr Asn Asn Leu Ala Asp
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Tyr Asn Asn Tyr Pro Pro Thr Phe Gly Gln Gly Thr Lys Leu
    210                 215                 220

Glu Ile Lys Arg
225

<210> SEQ ID NO 73
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Thr Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                    85                  90                  95

Thr Phe Gly Gln Gly Thr Lys Leu Glu Ile Lys Arg Thr Val Ala Ala
            100                 105                 110

Pro Ser Val Phe Ile Phe Pro Pro Asp Ile Gln Met Thr Gln Ser Pro
            115                 120                 125

Ser Ser Leu Ser Ala Ser Val Gly Asp Arg Val Thr Ile Thr Cys Ser
130                 135                 140

Ala Ser Gln Asp Ile Ser Asn Tyr Leu Asn Trp Tyr Gln Gln Lys Pro
145                 150                 155                 160

Gly Lys Ala Pro Lys Val Leu Ile Tyr Phe Thr Ser Ser Leu His Ser
            165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
            195                 200                 205

Gln Gln Tyr Ser Thr Val Pro Trp Thr Phe Gly Gln Gly Thr Lys Val
            210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
            245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
            275                 280                 285

Lys Asp Ser Thr Tyr Ser Leu Ser Ser Thr Leu Thr Leu Ser Lys Ala
290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
            325                 330

<210> SEQ ID NO 74
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
            35                  40                  45

Ala Thr Ile Ser Ser Ser Asp Gly Thr Thr Tyr Tyr Arg Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Tyr Tyr Asn Ser Pro Phe Ala Tyr Trp Gly Gln Gly Thr

```
                100             105                 110
Leu Val Thr Val Ser Ser Ala Ser Thr Lys Gly Pro Glu Val Gln Leu
            115                 120             125

Val Glu Ser Gly Gly Gly Leu Val Gln Pro Gly Gly Ser Leu Arg Leu
        130                 135             140

Ser Cys Ala Ala Ser Gly Tyr Thr Phe Thr Asn Tyr Gly Met Asn Trp
145                 150                 155                 160

Val Arg Gln Ala Pro Gly Lys Gly Leu Glu Trp Val Gly Trp Ile Asn
                165                 170             175

Thr Tyr Thr Gly Glu Pro Thr Tyr Ala Ala Asp Phe Lys Arg Arg Phe
            180                 185             190

Thr Phe Ser Leu Asp Thr Ser Lys Ser Thr Ala Tyr Leu Gln Met Asn
        195                 200             205

Ser Leu Arg Ala Glu Asp Thr Ala Val Tyr Tyr Cys Ala Lys Tyr Pro
    210                 215                 220

His Tyr Tyr Gly Ser Ser His Trp Tyr Phe Asp Val Trp Gly Gln Gly
225                 230                 235                 240

Thr Leu Val Thr Val Ser Ser Ala Ser Thr Lys Gly Pro Ser Val Phe
                245                 250             255

Pro Leu Ala Pro Ser Ser Lys Ser Thr Ser Gly Gly Thr Ala Ala Leu
            260                 265             270

Gly Cys Leu Val Lys Asp Tyr Phe Pro Glu Pro Val Thr Val Ser Trp
        275                 280             285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330             335

Ser Asn Thr Lys Val Asp Lys Lys Val Glu Pro Lys Ser Cys Asp Lys
            340                 345             350

Thr His Thr Cys Pro Pro Cys Pro Ala Pro Glu Ala Ala Gly Gly Pro
        355                 360             365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410             415

Ala Lys Thr Lys Pro Arg Glu Glu Gln Tyr Asn Ser Thr Tyr Arg Val
            420                 425             430

Val Ser Val Leu Thr Val Leu His Gln Asp Trp Leu Asn Gly Lys Glu
        435                 440             445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490             495

Cys Leu Val Lys Gly Phe Tyr Pro Ser Asp Ile Ala Val Glu Trp Glu
            500                 505             510

Ser Asn Gly Gln Pro Glu Asn Asn Tyr Lys Thr Thr Pro Pro Val Leu
        515                 520             525
```

```
Asp Ser Asp Gly Ser Phe Phe Leu Tyr Ser Lys Leu Thr Val Asp Lys
            530             535             540

Ser Arg Trp Gln Gln Gly Asn Val Phe Ser Cys Ser Val Met His Glu
545             550             555             560

Ala Leu His Asn His Tyr Thr Gln Lys Ser Leu Ser Leu Ser Pro Gly
                565             570             575

Lys

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gly Gly Gly Ser
1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Gly Ser
1
```

ANTI-DLL4/VEGF DUAL VARIABLE DOMAIN IMMUNOGLOBULIN AND USES THEREOF

This application is a divisional of U.S. application Ser. No. 14/068,976, filed Oct. 31, 2013, which claims the benefit of priority under 35 U.S.C. §119 of U.S. Provisional Application No. 61/721,072, filed Nov. 1, 2012, and U.S. Provisional Application No. 61/787,927, filed Mar. 15, 2013, all of which are incorporated herein by reference in their entirety.

The instant application contains a Sequence Listing which has been submitted electronically in ASCII format and is hereby incorporated by reference in its entirety. Said ASCII copy, created on Nov. 7, 2013, is named 12252.0081-00000_SL.txt and is 75,650 bytes in size.

Disclosed herein are multivalent and multispecific binding proteins, methods of making the binding proteins, and their uses in the diagnosis, inhibition, prevention and/or treatment of cancers, tumors, and/or other angiogenesis-dependent diseases.

Engineered proteins, such as multispecific binding proteins capable of binding two or more antigens, are known in the art. Such multispecific binding proteins can be generated using cell fusion, chemical conjugation, or recombinant DNA techniques. There are a variety of multispecific binding protein structures known in the art; however many such structures and methods have distinct disadvantages.

Bispecific antibodies have been produced using quadroma technology. However, the presence of mis-paired by-products and significantly reduced production yields with this technology means that sophisticated purification procedures are required. Bispecific antibodies can also be produced by chemical conjugation of two different mAbs. However, this approach does not yield homogeneous preparations.

Other approaches used previously include coupling of two parental antibodies with a hetero-bifunctional crosslinker, production of tandem single-chain Fv molecules, diabodies, bispecific diabodies, single-chain diabodies, and di-diabodies. However, each of these approaches have disadvantages. In addition, a multivalent antibody construct comprising two Fab repeats in the heavy chain of an IgG and capable of binding four antigen molecules has been described (see PCT Publication No. WO 0177342 and Miller et al. (2003) *J. Immunol.* 170(9): 4854-61).

Ligand-receptor systems have co-evolved to maintain specificity. Their interactions activate specific signaling for a particular biological activity. However, non-ligand-receptor binding proteins such as mono-specific antibodies, bi- or multi-specific binding proteins, noncompetitive antibody combinations or other receptor binding proteins to an extracellular domain (ECD) of a receptor may recognize epitopes distinct from a receptor ligand-binding site. Binding to such a distinct epitope(s) on the ECD of a receptor may transduce conformational changes to the intracellular domain, which may result in a novel unexpected signaling cascade.

U.S. Pat. No. 7,612,181 (incorporated herein by reference in its entirety) provides a novel family of binding proteins capable of binding two or more antigens with high affinity, which are called dual variable domain binding proteins (DVD binding protein) or dual variable domain immunoglobulins (DVD-Ig™). DVDs molecules are tetravalent dual-specific Ig-like proteins capable of binding two distinct epitopes on the same molecule or two different molecules simultaneously. DVDs are unique binding proteins comprised of two variable domains fused to the N-terminus of a bivalent antibody. The variable domains may be directly fused to one another or connected via synthetic peptide linkers of assorted length and amino acid composition. DVDs can be engineered with intact and functional Fc domains, allowing then to mediate appropriate effector functions. DVD format, due to its flexibility of choice of antibody pair, orientation of two antigen-binding domains and the length of the linker that joins them, may provide for novel therapeutic modalities.

While a variety of structures are provided in the art, some with advantages and disadvantages, specific constructs are required for preparing multivalent binding proteins with specific properties and which bind to specific targets. Additionally, new variable domain sequences can further improve the properties of the binding proteins. Specifically, improved DVDs that bind to DLL4 and VEGF could prove beneficial. Accordingly, disclosed herein are dual variable domain immunoglobulins using the binding protein framework disclosed in U.S. Pat. No. 7,612,181 (incorporated herein by reference in its entirety) and containing particular first and second polypeptide chains, each comprising first and second variable domain sequences (e.g., those listed in Table 2) that form functional binding sites for VEGF and DLL4. In some embodiments, the first and second polypeptide chains comprise first and second variable domain sequences that each contain the three CDRs from one of the sequences listed in Table 2 and form functional binding sites for VEGF and DLL4.

DLL4 is a ligand involved in cell-to-cell signaling through the Notch receptor pathway. Such cell-to-cell communication is required for many biological processes such as differentiation, proliferation, and homeostasis. The Notch-signaling pathway is one system that is utilized by a wide range of eukaryotes. This pathway, especially the Notch receptor, is also critical for functional tumor angiogenesis. Thus, inhibition of Notch receptor function, blockage of the Notch receptor, and/or blockage of the Notch-signaling pathway are potential strategies for anticancer compositions and therapies. Small molecule inhibitors of the Notch receptor have often proven to be toxic because they suppress wild type (normal) tissue expression of Notch receptors throughout the body. Thus, different members of the Notch-signaling pathway should be considered as potential targets for therapeutics. A vasculature ligand for the Notch receptor is Delta 4 or Delta-like 4 (DLL4). Largely expressed in the vasculature, DLL4 is critical for vascular development (Yan et al., *Clin. Cancer Res.*, 13(24): 7243-7246 (2007); Shutter et al., *Genes Dev.*, 14(11): 1313-1318 (2000); Gale et al., *Proc. Natl. Acad. Sci. USA*, 101(45): 15949-15954 (2004); Krebs et al., *Genes Dev.*, 14(11): 1343-1352 (2000)). Mice heterozygous for DLL4 are embryonically lethal due to major defects in vascular development (Gale et al., *Proc. Natl. Acad. Sci. USA*, 101(45): 15949-15954 (2004); Duarte et al., *Genes Dev.*, 18(20): 2474-2478 (2004); Krebs et al., *Genes Dev.*, 18(20): 2469-2473 (2004)).

The expression of DLL4 can be induced by VEGF (Liu et al., *Mol. Cell Biol.*, 23(1): 14-25 (2003); Lobov et al., *Proc. Natl. Acad. Sci. USA*, 104(9): 3219-3224 (2007)). VEGF is a signal protein produced by cells involved in angiogenesis. Additionally, DLL4 can negatively regulate VEGF signaling, in part through repressing VEGFR2 and inducing VEGR1 (Harrington et al., *Microvasc. Res.*, 75(2): 144-154 (2008); Suchting et al., *Proc. Natl. Acad. Sci. USA*, 104(9): 3225-3230 (2007)). Exquisite coordination between DLL4 and VEGF is essential for functional angiogenesis, making both DLL4 and VEGF potential targets for therapeutic intervention.

In addition to their physiological role, DLL4 and VEGF are also up-regulated in tumor blood vessels (Gale et al., *Proc. Natl. Acad. Sci. USA*, 101(45): 15949-15954 (2004); Mailhos et al., *Differentiation,* 69(2-3): 135-144 (2001); Patel et al., *Cancer Res.,* 65(19): 8690-8697 (2005); Patel et al., *Clin. Cancer Res.,* 12(16): 4836-4844 (2006); Noguera-Troise et al., *Nature,* 444(7122): 1032-1037 (2006)). Blockade of DLL4 has been shown to inhibit primary tumor growth in multiple models (Noguera-Troise et al., *Nature,* 444(7122): 1032-1037 (2006); Ridgway et al., *Nature,* 444(7122): 1083-1087 (2006); Scehnet et al., *Blood,* 109(11): 4753-4760 (2007)). The inhibition of DLL4 is even effective against tumors that are resistant to anti-VEGF therapy. Thus, the combinatorial inhibition of both DLL4 and VEGF could provide an enhanced anti-tumor therapy. Interestingly, unlike VEGF inhibition that reduces tumor vessel formation, DLL4 blockade leads to an increase in tumor vasculature density wherein the vessels are abnormal, cannot support efficient blood transport, and are effectively nonfunctional. Thus, disruption of both VEGF and DLL4 provides for different methods of action for potential anti-cancer treatment.

There is a need in the art for improved multivalent binding proteins capable of binding DLL4 and VEGF. Accordingly, novel binding proteins are provided, wherein the binding proteins are capable of binding DLL4 and VEGF.

Binding proteins capable of targeting two epitopes are provided, wherein the binding proteins are capable of binding DLL4 and VEGF. In an embodiment, binding proteins capable of binding epitopes of DLL4 and VEGF with high affinity are provided. In an embodiment, the binding proteins comprise a dual variable domain binding protein framework that contains the CDR and variable domain sequences listed in Table 2. In an embodiment, the dual variable domain binding protein framework comprises the framework disclosed in U.S. Pat. No. 7,612,181 (incorporated herein by reference in its entirety).

In one embodiment, binding proteins comprising a polypeptide chain that can bind two epitopes of two different proteins (VEGF and DLL4) are provided, wherein the polypeptide chain comprises VD1-(X1)n-VD2-C-(X2)n, wherein VD1 is a first variable domain, VD2 is a second variable domain, C is a constant domain, X1 represents an amino acid or polypeptide, X2 represents an Fc region and n is 0 or 1, are provided. In some embodiments, the VD1 and VD2 in the binding protein are heavy chain variable domains. In certain embodiments, VD1 and VD2 are capable of binding an epitope of DLL4 and an epitope of VEGF. In some embodiments, C is a heavy chain constant domain, such as CH1. In certain embodiments, X1 is a linker with the proviso that X1 is not CH1.

In various embodiments, the binding protein disclosed herein comprises a polypeptide chain that binds an epitope of DLL4 and an epitope of VEGF, wherein the polypeptide chain comprises VD1-(X1)n-VD2-C-(X2)n, wherein VD1 comprises a first heavy chain variable domain, VD2 comprises a second heavy chain variable domain, C comprises a heavy chain constant domain, X1 comprises a linker, and X2 comprises an Fc region. In an embodiment, X1 is a linker with the proviso that it is not CH1. In an embodiment, the VD1 and VD2 heavy chain variable domains each comprise three CDRs chosen from the CDRs in SEQ ID NO: 39, 41, 43, 45, 47, 49, 51, or 53, wherein at least one of the VD1 and/or VD2 heavy chain variable domains comprises the three CDRs in SEQ ID NO: 39. In another embodiment, the binding protein is capable of binding DLL4 and VEGF. In an embodiment, the VD1 and VD2 heavy chain variable domains comprise SEQ ID NO: 39, 41, 43, 45, 47, 49, 51, or 53, wherein at least one of the VD1 and/or VD2 heavy chain variable domains comprises SEQ ID NO: 39.

In various embodiments, the binding protein disclosed herein comprises a polypeptide chain that binds an epitope of DLL4 and an epitope of VEGF, wherein the polypeptide chain comprises VD1-(X1)n-VD2-C-(X2)n, wherein VD1 comprises a first light chain variable domain, VD2 comprises a second light chain variable domain, C comprises a light chain constant domain, X1 comprises a linker, and X2 does not comprise an Fc region. In an embodiment, X1 is a linker with the proviso that it is not a CH1 or a CL. In an embodiment, the VD1 and VD2 light chain variable domains each comprise three CDRs chosen from the CDRs in SEQ ID NO: 40, 42, 44, 46, 48, 50, 52, or 54, wherein at least one of the VD1 and/or VD2 light chain variable domains comprises the three CDRs in SEQ ID NO: 40. In another embodiment, the binding protein is capable of binding DLL4 and VEGF. In an embodiment, the VD1 and VD2 light chain variable domains each comprise SEQ ID NO: 40, 42, 44, 46, 48, 50, 52, or 54, wherein at least one of the VD1 and/or VD2 light chain variable domains comprises SEQ ID NO: 40.

In another embodiment, a binding protein that binds an epitope of DLL4 and an epitope of VEGF is disclosed, wherein the first polypeptide chain comprises VD1-(X1)n-VD2-C-(X2)n, wherein VD1 is a first heavy chain variable domain, VD2 is a second heavy chain variable domain, C is a heavy chain constant domain, X1 is a first linker, and X2 is an Fc region; and the second polypeptide chain comprises VD1-(X1)n-VD2-C-(X2)n, wherein VD1 is a first light chain variable domain, VD2 is a second light chain variable domain, C is a light chain constant domain, X1 is a second linker, and X2 does not comprise an Fc region is provided. In some embodiments, the first and second X1 are the same. In other embodiments, the first and second X1 are different. In some embodiments the first X1 is not a CH1 domain and/or the second X1 is not a CH1 or a CL domain. In one embodiment, the first X1 and the second X1 are short (e.g., 6, 5, 4, 3, or 2 amino acid) linkers. In another embodiment, the first X1 and the second X1 are long (e.g., 6, 7, 8, 9, 10, 11, 12, 15, 20, 25, 30, or greater amino acid) linkers. In another embodiment, the first X1 is a short linker and the second X1 is a long linker. In another embodiment, the first X1 is a long linker and the second X1 is a short linker. In an embodiment, the VD1 and VD2 heavy chain variable domains each comprise three CDRs from SEQ ID NO: 39, 41, 43, 45, 47, 49, 51, or 53, wherein at least one of the VD1 and/or VD2 heavy chain variable domains comprises the three CDRs in SEQ ID NO: 39, and the VD1 and VD2 light chain variable domains comprise three CDRs from SEQ ID NO: 40, 42, 44, 46, 48, 50, 52, or 54, wherein at least one of the VD1 and/or VD2 light chain variable domains comprises the three CDRs in SEQ ID NO: 40. In another embodiment, the binding protein is capable of binding DLL4 and VEGF. In an embodiment, the VD1 and VD2 heavy chain variable domains comprise SEQ ID NO: 39, 41, 43, 45, 47, 49, 51, or 53, wherein at least one of the VD1 and/or VD2 heavy chain variable domains comprises SEQ ID NO: 39, and the VD1 and VD2 light chain variable domains comprise SEQ ID NO: 40, 42, 44, 46, 48, 50, 52, or 54, wherein at least one of the VD1 and/or VD2 light chain variable domains comprises SEQ ID NO: 40.

In an embodiment, a Dual Variable Domain (DVD) binding protein comprises four polypeptide chains, wherein each of the first two polypeptide chains comprises VD1-(X1)n-VD2-C-(X2)n, wherein VD1 is a first heavy chain variable domain, VD2 is a second heavy chain variable domain, C is a heavy chain constant domain, X1 is a first linker, and X2 is an Fc region; and each of the second two polypeptide chain comprises VD1-(X1)n-VD2-C-(X2)n, wherein VD1 is a first light chain variable domain, VD2 is a second light chain variable domain, C is a light chain constant domain, X1 is a second linker, and X2 does not comprise an Fc region. Such a DVD binding protein has four antigen binding sites. In some embodiments, the first and second X1 are the same. In other embodiments, the first and second X1 are different. In some embodiments, the first X1 is not a CH1 domain and/or the second X1 is not a CH1 or a CL domain. In another embodiment, the binding proteins disclosed herein are capable of binding epitopes on two different proteins. Accordingly, in some embodiments, the binding proteins comprise at least two variable domain sequences (e.g., VD1 and VD2) capable of binding epitopes on two different proteins, in any orientation. In some embodiments, VD1 and VD2 are independently chosen. In an embodiment, the VD1 and VD2 heavy chain variable domains each comprise three CDRs from SEQ ID NO: 39, 41, 43, 45, 47, 49, 51, or 53, wherein at least one of the VD1 and/or VD2 heavy chain variable domains comprises the three CDRs in SEQ ID NO: 39, and the VD1 and VD2 light chain variable domains comprise three CDRs from SEQ ID NO: 40, 42, 44, 46, 48, 50, 52, or 54, wherein at least one of the VD1 and/or VD2 light chain variable domains comprises the three CDRs in SEQ ID NO: 40. In another embodiment, the binding protein is capable of binding DLL4 and VEGF. In an embodiment, the VD1 and VD2 heavy chain variable domains each comprise SEQ ID NO: 39, 41, 43, 45, 47, 49, 51, or 53, wherein at least one of the VD1 and/or VD2 heavy chain variable domains comprises SEQ ID NO: 39, and the VD1 and VD2 light chain variable domains each comprise SEQ ID NO: 40, 42, 44, 46, 48, 50, 52, or 54, wherein at least one of the VD1 and/or VD2 light chain variable domains comprises SEQ ID NO: 40.

In another embodiment, the binding protein comprises a heavy chain and a light chain sequence as shown in Table 2, wherein at least one of the VD1 and/or VD2 heavy chain variable domains comprises SEQ ID NO: 39 and/or at least one of the VD1 and/or VD2 light chain variable domains comprises SEQ ID NO: 40.

In a further embodiment, any of the heavy chain, light chain, two chain, or four chain embodiments includes at least one X1 linker comprising the linkers selected from SEQ ID NO: 1-38. In an embodiment, X2 is an Fc region. In another embodiment, X2 is a variant Fc region.

In still another embodiment, the Fc region, if present in the first polypeptide, is a native sequence Fc region or a variant sequence Fc region. In yet another embodiment, the Fc region is an Fc region from an IgG1, an Fc region from an IgG2, an Fc region from an IgG3, an Fc region from an IgG4, an Fc region from an IgA, an Fc region from an IgM, an Fc region from an IgE, or an Fc region from an IgD. In certain embodiments, the Fc region is an Fc region from a human IgG1 LALA mutant, which is a mutant of the b12 antibody that provides protection against the HIV virus.

A method of making a binding protein that binds two different target proteins is provided. In an embodiment, the method of making a binding protein comprises the steps of a) obtaining a first parent antibody, or antigen binding portion thereof, that binds a first epitope; b) obtaining a second parent antibody, or antigen binding portion thereof, that binds a second epitope; c) preparing construct(s) encoding any of the binding proteins described herein; and d) expressing the polypeptide chains, such that a binding protein that binds the first and the second epitope is generated.

In any of the embodiments herein, the VD1 heavy chain variable domain, if present, and light chain variable domain, if present, can be from a first parent antibody or antigen binding portion thereof; the VD2 heavy chain variable domain, if present, and light chain variable domain, if present, can be from a second parent antibody or antigen binding portion thereof. The first and second parent antibodies can be the same or different.

In one embodiment, the first parent antibody or antigen binding portion thereof, binds a first antigen, and the second parent antibody or antigen binding portion thereof, binds a second antigen. In an embodiment, the first and second antigens are different antigens. In another embodiment, the first parent antibody or antigen binding portion thereof binds the first antigen with a potency different from the potency with which the second parent antibody or antigen binding portion thereof binds the second antigen. In yet another embodiment, the first parent antibody or antigen binding portion thereof binds the first antigen with an affinity different from the affinity with which the second parent antibody or antigen binding portion thereof binds the second antigen.

In another embodiment, the first parent antibody or antigen binding portion thereof, and the second parent antibody or antigen binding portion thereof are a human antibody, CDR grafted antibody, humanized antibody, and/or affinity matured antibody.

In another embodiment, the binding protein possesses at least one desired property exhibited by the first parent antibody or antigen binding portion thereof, or by the second parent antibody or antigen binding portion thereof. Alternatively, the first parent antibody or antigen binding portion thereof and the second parent antibody or antigen binding portion thereof possess at least one desired property exhibited by the binding protein. In an embodiment, the desired property is one or more antibody parameters. In another embodiment, the antibody parameters are antigen specificity, affinity to antigen, potency, biological function, epitope recognition, stability, solubility, production efficiency, immunogenicity, pharmacokinetics, bioavailability, tissue cross reactivity, or orthologous antigen binding. In an embodiment, the binding protein is multivalent. In another embodiment, the binding protein is multispecific. The multivalent and or multispecific binding proteins described herein have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist binding protein; and/or (3) induce cell death and/or apoptosis of a cell expressing an antigen to which the multivalent binding protein is capable of binding. The "parent antibody", which provides at least one antigen binding specificity of the multivalent and or multispecific binding protein, may be one that is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may acquire one or more of them when constructed as a multivalent binding protein as described herein.

In another embodiment, the binding protein has an on rate constant ($K_{on}$) to one or more targets of at least about $10^2$ $M^{-1}s^{-1}$; at least about $10^3$ $M^{-1}s^{-1}$; at least about $10^4$ $M^{-1}s^{-1}$; at least about $10^5$ $M^{-1}s^{-1}$; or at least about $10^6$ $M^{-1}s^{-1}$, as measured by surface plasmon resonance. In an embodiment, the binding protein has an on rate constant ($K_{on}$) to one or more targets from about $10^2$ $M^{-1}s^{-1}$ to about $10^3$ $M^{-1}s^{-1}$; from about $10^3$ $M^{-1}s^{-1}$ to about $10^4$ $M^{-1}s^{-1}$; from about $10^4$ $M^{-1}s^{-1}$ to about $10^5$ $M^{-1}s^{-1}$; or from about $10^5$ $M^{-1}s^{-1}$ to about $10^6$ $M^{-1}s^{-1}$, as measured by surface plasmon resonance.

In another embodiment, the binding protein has an off rate constant ($K_{off}$) for one or more targets of at most about $10^{-2}s^{-1}$; at most about $10^{-3}s^{-1}$; at most about $10^{-4}s^{-1}$; at most about $10^{-5}s^{-1}$; or at most about $10^{-6}s^{-1}$, as measured by surface plasmon resonance. In an embodiment, the binding protein has an off rate constant ($K_{off}$) to one or more targets of about $10^{-2}$ $s^{-1}$ to about $10^{-3}s^{-1}$; of about $10^{-3}s^{-1}$ to about $10^{-4}$ $s^{-1}$; of about $10^{-4}$ $s^{-1}$ to about $10^{-5}$ $s^{-1}$; or of about $10^{-5}$ $s^{-1}$ to about $10^{-6}$ $s^{-1}$, as measured by surface plasmon resonance.

In another embodiment, the binding protein has an equilibrium dissociation constant ($K_D$) to one or more targets of at most about $10^{-7}$ M; at most about $10^{-8}$ M; at most about $10^{-9}$ M; at most about $10^{-10}$ M; at most about $10^{-11}$ M; or at most about $10^{-12}$ M. In an embodiment, the binding protein has an equilibrium dissociation constant ($K_D$) to its targets of about $10^{-7}$ M to about $10^{-8}$ M; of about $10^{-8}$ M to about $10^{-9}$ M; of about $10^{-9}$ M to about $10^{-10}$ M; of about $10^{-10}$ M to about $10^{-11}$ M; or of about $10^{-11}$ M to about $10^{-12}$ M.

In some embodiments, an anti-DLL4/anti-VEGF binding protein exhibits increased potency (e.g., increased ability to interfere with, inhibit and/or neutralize DLL4 and/or VEGF activity) as compared to an anti-DLL4 or anti-VEGF antibody. In some embodiments, the potency of the binding protein can be evaluated in any assay for evaluating VEGF and/or DLL4 activity, e.g., a VEGF and/or DLL4 binding ELISA assay, a BIACORE™ assay, a DLL4-Notch reporter assay, a VEGF-stimulated Endothelial Cell Proliferation/Survival assay, or any other assay known to one of skill in the art. In some embodiments, the binding protein exhibits increased DLL4 potency in the presence of VEGF.

In another embodiment, the binding protein is a conjugate comprising the binding protein and further comprising an agent. In an embodiment, the agent is an immunoadhesion molecule, an imaging agent, a therapeutic agent, or a cytotoxic agent. In an embodiment, the imaging agent is a radiolabel, an enzyme, a fluorescent label, a luminescent label, a bioluminescent label, a magnetic label, or biotin. In another embodiment, the radiolabel is $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$. In yet another embodiment, the therapeutic or cytotoxic agent is an anti-metabolite, an alkylating agent, an antibiotic, a growth factor, a cytokine, an anti-angiogenic agent, an anti-mitotic agent, an anthracycline, toxin, or an apoptotic agent. In some embodiments, the agent is one or more of: irinotecan, leucovorin, 5-FU, temozolomide, gemcitabine, and paclitaxel. In an embodiment, the agent is irinotecan. In an embodiment, the agent is leucovorin. In an embodiment, the agent is 5-FU. In an embodiment, the agent is irinotecan, leucovorin, and 5-FU. In an embodiment, the agent is temozolomide. In an embodiment, the agent is gemcitabine. In an embodiment, the agent is paclitaxel.

In some embodiments, a composition is disclosed comprising one or more binding protein as disclosed herein and one or more additional agent, e.g., a chemotherapeutic agent. For example, the composition can comprise one or more binding proteins in solution with one or more additional agents. In some embodiments, the agent is one or more of: irinotecan, leucovorin, 5-FU, temozolomide, gemcitabine, and paclitaxel. In an embodiment, the agent is irinotecan. In an embodiment, the agent is leucovorin. In an embodiment, the agent is 5-FU. In an embodiment, the agent is irinotecan, leucovorin, and 5-FU. In an embodiment, the agent is temozolomide. In an embodiment, the agent is gemcitabine. In an embodiment, the agent is paclitaxel.

In another embodiment, the binding protein is a crystallized binding protein and exists as a crystal. In an embodiment, the crystal is a carrier-free pharmaceutical controlled release crystal. In another embodiment, the crystallized binding protein has a greater half life in vivo than the soluble counterpart of the binding protein. In yet another embodiment, the crystallized binding protein retains biological activity.

In another embodiment, the binding protein described herein is glycosylated. For example, the glycosylation pattern is a human glycosylation pattern.

An isolated nucleic acid encoding any one of the binding proteins disclosed herein is also provided. A further embodiment provides a vector comprising the isolated nucleic acid disclosed herein wherein the vector is pcDNA; pTT (Durocher et al. (2002) Nucleic Acids Res. 30(2); pTT3 (pTT with additional multiple cloning site; pEFBOS (Mizushima and Nagata (1990) Nucleic Acids Res. 18(17); pBV; pJV; pcDNA3.1 TOPO; pEF6 TOPO; pBOS; pHybE; or pBJ. In an embodiment, the vector is a vector disclosed in US Patent Publication No. 20090239259.

In another aspect, a host cell is transformed with the vector disclosed herein. In an embodiment, the host cell is a prokaryotic cell, for example, *E. Coli*. In another embodiment, the host cell is a eukaryotic cell, for example, a protist cell, an animal cell, a plant cell, or a fungal cell. In an embodiment, the host cell is a mammalian cell including, but not limited to, CHO, COS, NS0, SP2, PER.C6, or a fungal cell, such as *Saccharomyces cerevisiae*, or an insect cell, such as Sf9. In an embodiment, two or more binding proteins, e.g., with different specificities, are produced in a single recombinant host cell. For example, the expression of a mixture of antibodies has been called Oligoclonics™ (Merus B.V., The Netherlands) U.S. Pat. Nos. 7,262,028 and 7,429,486.

A method of producing a binding protein disclosed herein comprising culturing any one of the host cells disclosed herein in a culture medium under conditions sufficient to produce the binding protein is provided. In an embodiment, 50%-75% of the binding protein produced by this method is a dual specific tetravalent binding protein. In another embodiment, 75%-90% of the binding protein produced by this method is a dual specific tetravalent binding protein. In another embodiment, 90%-95% of the binding protein produced is a dual specific tetravalent binding protein.

One embodiment provides a composition for the release of a binding protein wherein the composition comprises a crystallized binding protein, an ingredient, and at least one polymeric carrier. In an embodiment, the polymeric carrier is poly (acrylic acid), a poly (cyanoacrylate), a poly (amino acid), a poly (anhydride), a poly (depsipeptide), a poly (ester), poly (lactic acid), poly (lactic-co-glycolic acid) or PLGA, poly (b-hydroxybutyrate), poly (caprolactone), poly (dioxanone), poly (ethylene glycol), poly ((hydroxypropyl) methacrylamide, poly [(organo)phosphazene], a poly (ortho ester), poly (vinyl alcohol), poly (vinylpyrrolidone), a maleic anhydride-alkyl vinyl ether copolymer, a pluronic polyol, albumin, alginate, cellulose, a cellulose derivative, collagen, fibrin, gelatin, hyaluronic acid, an oligosaccharide, a glycaminoglycan, a sulfated polysaccharide, or blends and copolymers thereof. In an embodiment, the ingredient is albumin, sucrose, trehalose, lactitol, gelatin, hydroxypropyl-β-cyclodextrin, methoxypolyethylene glycol, or polyethylene glycol.

Another embodiment provides a method for treating a mammal comprising the step of administering to the mammal an effective amount of a composition disclosed herein.

A pharmaceutical composition comprising a binding protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule blocker (including but not limited to anti-B7.1, anti-B7.2, CTLA4-Ig, anti-CD20), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, and an anti-IL-6/cytokine receptor antibody), methotrexate, cyclosporin, rapamycin, FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist. In some embodiments, the additional therapeutic agent is a chemotherapeutic agent. In some embodiments, the additional agent is one or more of: irinotecan, leucovorin, 5-FU, temozolomide, gemcitabine, and paclitaxel. In an embodiment, the agent is irinotecan. In an embodiment, the agent is leucovorin. In an embodiment, the agent is 5-FU. In an embodiment, the agent is irinotecan, leucovorin, and 5-FU. In an embodiment, the agent is temozolomide. In an embodiment, the agent is gemcitabine. In an embodiment, the agent is paclitaxel.

In various embodiments, a method is provided for diagnosing and/or treating a human subject suffering from a disorder which can be diagnosed and/or treated by targeting VEGF and/or DLL4 (e.g., any angiogenesis disorder or any other disorder associated with aberrant expression of VEGF and/or DLL4), comprising administering to the human subject a binding protein disclosed herein such that the activity of the target, or targets, in the human subject is inhibited and one or more symptoms is alleviated or treatment is achieved is provided. The binding proteins provided herein can be used to diagnose and/or treat humans suffering from primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

In some embodiments, a method of treating cancer in a patient comprises administering one or more of the binding proteins disclosed herein or a pharmaceutical composition thereof. In an embodiment, the cancer is colon cancer. In an embodiment, the cancer is glioblastoma. In an embodiment, the cancer is pancreatic cancer. In an embodiment, the cancer is breast cancer. In some embodiments, the methods of treating cancer, comprising administering one or more of the binding proteins disclosed herein or a pharmaceutical composition thereof, produce a reduction in tumor growth or a delay in tumor growth that is at least about equivalent to the expected additive effects of a combination of an anti-VEGF antibody and an anti-DLL4 antibody. In some embodiments, the methods produce a reduction in tumor growth or a delay in tumor growth that is more than additive (e.g., a larger reduction than that expected from adding the predicted effects of an anti-VEGF antibody and an anti-DLL4 antibody).

In some embodiments, a method of treating a cancer comprises administering one or more of the binding proteins disclosed herein or a pharmaceutical composition thereof, in combination with one or more additional agents, e.g., a chemotherapeutic or biological agent. In some embodiments, the agent is one or more of: regorafenib (STIVAGRA™), pertuzumab (PERJECTA™), irinotecan, leucovorin, 5-FU, temozolomide, gemcitabine, and paclitaxel. In an embodiment, the agent is irinotecan. In an embodiment, the agent is leucovorin. In an embodiment, the agent is 5-FU. In an embodiment, the agent is irinotecan, leucovorin, and 5-FU. In an embodiment, the agent is temozolomide. In an embodiment, the agent is gemcitabine. In an embodiment, the agent is paclitaxel. In some embodiments, the methods of treating cancer, comprising administering one or more of the binding proteins disclosed herein or a pharmaceutical composition thereof, in combination with one or more additional agents, produce a reduction in tumor growth or a delay in tumor growth that is at least equivalent to the expected additive effects of a combination of the binding protein and the additional agent. In some embodiments, the methods produce a reduction in tumor growth or a delay in tumor growth that is more than additive (e.g., a larger reduction than that expected from adding the predicted effects of the binding protein and the additional agent).

In some embodiments, a method of treating colon cancer comprises administering one or more of the binding proteins disclosed herein or a pharmaceutical composition thereof, optionally in combination with one or more of irinotecan, leucovorin, and 5-FU. In some embodiments, a method of treating glioblastoma comprises administering one or more of the binding proteins disclosed herein or a pharmaceutical composition thereof, optionally in combination with temozolomide. In some embodiments, a method of treating pancreatic cancer comprises administering one or more of the binding proteins disclosed herein or a pharmaceutical composition thereof, optionally in combination with gemcitabine. In some embodiments, a method of treating breast cancer comprises administering one or more of the binding proteins disclosed herein or a pharmaceutical composition thereof, optionally in combination with paclitaxel.

In various embodiments, the binding proteins provided herein can be administered in combination with one or more anti-hypertensive agent. The one or more anti-hypertensive agent can be selected from the group consisting of a diuretic, an adrenergic receptor antagonist, a calcium channel blocker, renin inhibitors, ACE inhibitors, angiotensin II receptor antagonists, vasodilators, and alpha-2 agonists. For example, the agent can be one or more of clonidine, methyldopa, hydralazine, prazosin, reserpine, moxonidine, guanfacine, perindopril/indapamide, lofexidine, and metirosine. In some embodiments, the binding proteins provided herein can be administered in combination with one or more anticoagulant. For example, the anticoagulant can be one or more of warfarin, heparin, low molecular weight heparin, dalteparin sodium, argatroban, bivalirudin, lepirudin, and dextrose. In some embodiment, the binding proteins provided herein can be administered in combination with one or more anti-hypertensive agent and one or more anticoagulant.

In various embodiments, the binding proteins provided herein can be used to diagnose and/or treat humans suffering from macular degeneration (including the wet form), diabetic retinopathy, and/or any other disease or disorder characterized by vascular overgrowth or edema.

In an embodiment, the binding proteins, or antigen-binding portions thereof, are used to treat cancer or in the prevention or inhibition of metastases from the tumors described herein, either when used alone or in combination with radiotherapy and/or chemotherapeutic agents.

In an embodiment, the chemotherapeutic or biological agents with which binding proteins provided herein can be combined include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Efudex®; Eligard™; Ellence™; Eloxatin™; Elspar®; Emcyt®; Epirubicin; Epoetin Alfa; Erbitux; Erlotinib; *Erwinia* L-asparaginase; Estramustine; Ethyol Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; Iressa®; Irinotecan; Isotretinoin; Ixabepilone; Ixempra™; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Novantrone®; Nplate; Octreotide; Octreotide acetate; Ofatumumab; Oncospar®; Oncovin®; Ontak®; Onxal™; Oprelvekin; Oxapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pentostatin; Phenylalanine Mustard; Platinol®; Platinol-AQ®; Prednisolone; Prednisone; Prelone®; Procarbazine; PROCRIT®; Proleukin®; Prolifeprospan 20 with Carmustine Implant; Purinethol®; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tretinoin; Trexall™; Trisenox®; TSPA; TYKERB®; VCR; Vectibix™; Velban®; Velcade®; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®, and/or any other agent not specifically listed here that target similar pathways.

In another embodiment, methods of treating a patient suffering from a disorder comprise the step of administering one or more of the binding proteins disclosed herein alone or administering the binding protein(s) before, concurrently, or after the administration of a second agent. In a particular embodiment, the pharmaceutical compositions disclosed herein are administered to a patient by oral, parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In various embodiments, methods of determining the presence, amount or concentration of one or more antigens, or fragments thereof, in a test sample are provided, wherein the one or more antigens or fragments thereof are DLL4 and/or VEGF. The method comprises assaying the test sample for the antigen, or fragment thereof, by an immunoassay. The immunoassay (i) employs at least one binding protein and at least one detectable label and (ii) comprises comparing a signal generated by the detectable label as a direct or indirect indication of the presence, amount or concentration of the antigen, or fragment thereof, in the test sample to a signal generated as a direct or indirect indication of the presence, amount or concentration of the antigen, or fragment thereof, in a control or a calibrator. The calibrator is optionally part of a series of calibrators in which each of the calibrators differs from the other calibrators in the series by the concentration of the antigen, or fragment thereof. The method can comprise (i) contacting the test sample with at least one capture agent, which binds to an epitope on the antigen, or fragment thereof, so as to form a complex comprising the capture agent and the antigen or fragment thereof (ii) contacting the complex comprising the capture agent and the antigen or fragment thereof with at least one detection agent, which comprises a detectable label and binds to an epitope on the antigen, or fragment thereof, that is not bound by the capture agent, to form a detection complex, and (iii) determining the presence, amount or concentration of the antigen, or fragment thereof, in the test sample based on the signal generated by the detectable label in the detection complex formed in (ii), wherein at least one capture agent and/or at least one detection agent is the at least one binding protein.

Alternatively, in some embodiments the method of determining the presence, amount or concentration of one or more antigens, or fragments thereof, in a test sample can comprise (i) contacting the test sample with at least one capture agent, which binds to an epitope on the antigen, or fragment thereof, so as to form a complex comprising the capture agent and the antigen or fragment thereof and simultaneously or sequentially, in either order, contacting the test sample with detectably labeled antigen, or fragment thereof, which can compete with any antigen, or fragment thereof, in the test sample for binding to the at least one capture agent, wherein any antigen, or fragment thereof, present in the test sample and the detectably labeled antigen compete with each other to form a detection complex and (ii) determining the presence, amount or concentration of the antigen, or fragment thereof, in the test sample based on the signal generated by the detectable label in the detection complex formed in (i), wherein at least one capture agent is the at least one binding protein and wherein the signal generated by the detectable label in the capture detection complex is inversely proportional to the amount or concentration of antigen, or fragment thereof, in the test sample.

In various embodiments, the test sample can be from a patient, in which case the method can further comprise diagnosing, prognosticating, or assessing the efficacy of therapeutic/prophylactic treatment of the patient. If the method further comprises assessing the efficacy of therapeutic/prophylactic treatment of the patient, the method optionally further comprises modifying the therapeutic/prophylactic treatment of the patient as needed to improve efficacy. The method can be adapted for use in an automated system or a semi-automated system. Accordingly, the methods described herein also can be used to determine whether or not a subject has or is at risk of developing a given disease, disorder or condition. Specifically, such a method can comprise the steps of:

(a) determining the concentration or amount of one or more analytes, or fragments thereof, in a test sample from a subject (e.g., using the methods described herein, or methods known in the art); and (b) comparing the concentration or amount of the analyte(s), or fragment(s) thereof, as determined in step (a) with a predetermined level, wherein, if the concentration or amount of analyte(s) determined in step (a) is favorable with respect to a predetermined level, then the subject is determined not to have or be at risk for a given disease, disorder or condition. However, if the concentration or amount of analyte(s) determined in step (a) is unfavorable with respect to the predetermined level, then the subject is determined to have or be at risk for a given disease, disorder or condition.

Additionally, provided herein are methods of monitoring the progression of a disease in a subject. In some embodiments, the methods comprise the steps of:

(a) determining the concentration or amount in a test sample from a subject of one or more analyte(s);

(b) determining the concentration or amount of analyte(s) in a later test sample from the same subject; and (c) comparing the concentration or amount of analyte(s) as determined in step (b) with the concentration or amount of analyte(s) determined in step (a), wherein if the concentration or amount determined in step (b) is unchanged or is unfavorable when compared to the concentration or amount determined in step (a), then the disease in the subject is determined to have continued, progressed or worsened. By comparison, if the concentration or amount as determined in step (b) is favorable when compared to the concentration or amount as determined in step (a), then the disease in the subject is determined to have discontinued, regressed or improved.

Optionally, the methods of monitoring the progression of a disease further comprises comparing the concentration or amount of analyte(s) as determined in step (b), for example, with a predetermined level. Further, optionally the methods comprise treating the subject with one or more pharmaceutical compositions for a period of time if the comparison shows that the concentration or amount of analyte(s) as determined in step (b), for example, is unfavorably altered with respect to the predetermined level.

Also provided is a kit for assaying a test sample for the presence or concentration of one or more antigens, or fragments thereof, wherein the one or more antigens are DLL4 and/or VEGF. The kit comprises at least one binding protein, as described herein, for assaying the test sample for an antigen, or fragment thereof, and instructions for assaying the test sample for an antigen, or fragment thereof. In an embodiment, the at least one binding protein is optionally detectably labeled.

BRIEF DESCRIPTION OF THE DRAWINGS

FIG. 1 is a schematic representation of Dual Variable Domain (DVD) binding protein constructs and shows the strategy for generation of a DVD binding protein from two parent antibodies.

DETAILED DESCRIPTION

Multivalent and/or multispecific binding proteins capable of binding epitopes on two different proteins are provided. Dual variable domain binding proteins (also referred to as DVDs, DVD binding proteins, or dual variable domain immunoglobulins (DVD-Ig™)), and pharmaceutical compositions thereof, as well as nucleic acids, recombinant expression vectors and host cells for making such DVD binding proteins are also provided. Methods of using the DVD binding proteins to detect specific antigens, either in vitro or in vivo are also provided.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting. Any range described here will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent documents incorporated by reference contradict the disclosure contained in the specification, the specification will supersede any contradictory material.

Generally, nomenclatures used in connection with cell and tissue culture, molecular biology, immunology, microbiology, genetics and protein and nucleic acid chemistry and hybridization described herein are those well known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein unless otherwise indicated. The nomenclatures used in connection with, and the laboratory procedures and techniques of, analytical chemistry, synthetic organic chemistry, and medicinal and pharmaceutical chemistry described herein are those well known and commonly used in the art unless otherwise indicated. Standard techniques are used for chemical syntheses, chemical analyses, pharmaceutical preparation, formulation, and delivery, and treatment of patients.

So that the disclosure may be more readily understood, select terms are defined below.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The CH is comprised of three domains, CH1, CH2 and CH3. Each light chain is comprised of a light chain variable region (VL) and a light chain constant region (CL). The CL is comprised of a single CL domain. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "bispecific antibody" refers to an antibody that binds one antigen (or epitope) on one of its two binding arms (one pair of HC/LC), and binds a different antigen (or epitope) on its second binding arm (a different pair of HC/LC). A bispecific antibody has two distinct antigen binding arms (in both specificity and CDR sequences), and is monovalent for each antigen to which it binds. Bispecific antibodies include those generated by quadroma technology (Milstein and Cuello (1983) Nature 305(5934): 537-40), by chemical conjugation of two different monoclonal antibodies (Staerz et al. (1985) Nature 314(6012): 628-31), or by knob-into-hole or similar approaches which introduces mutations in the Fc region (Holliger et al. (1993) Proc. Natl. Acad. Sci. USA 90(14): 6444-6448).

An "affinity matured" antibody is an antibody with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. Affinity matured antibodies are produced by procedures known in the art. Marks et al. (1992) BioTechnology 10:779-783 describes affinity maturation by VH and VL domain shuffling. Random mutagenesis of CDR and/or framework residues is described by Barbas et al. (1994) Proc. Nat. Acad. Sci. USA 91:3809-3813; Schier et al. (1995) Gene 169:147-155; Yelton et al. (1995) J. Immunol. 155:1994-2004; Jackson et al. (1995) J. Immunol. 154(7):3310-9; Hawkins et al. (1992) J. Mol. Biol. 226:889-896 and mutation at selective mutagenesis positions, contact or hypermutation positions with an activity enhancing amino acid residue as described in U.S. Pat. No. 6,914,128.

The term "CDR-grafted antibody" refers to an antibody that comprises heavy and light chain variable region sequences in which the sequences of one or more of the CDR regions of VH and/or VL are replaced with CDR sequences of another antibody. For example, the two antibodies can be from different species, such as antibodies having murine heavy and light chain variable regions in which one or more of the murine CDRs has been replaced with human CDR sequences.

The term "humanized antibody" refers to an antibody from a non-human species that has been altered to be more "human-like", i.e., more similar to human germline sequences. One type of humanized antibody is a CDR-grafted antibody, in which non-human CDR sequences are introduced into human VH and VL sequences to replace the corresponding human CDR sequences. A "humanized antibody" is also an antibody or a variant, derivative, analog or fragment thereof that comprises framework region (FR) sequences having substantially identity (e.g., at least 80%, at least 85%, at least 90%, at least 95%, at least 98% or at least 99% identity) to the amino acid sequence of a human antibody FR sequences and at least one CDR having substantial identity (e.g., at least 80%, at least 85%, at least 90%, at least 95%, at least 98% or at least 99% identity) to the amino acid sequence of a non-human CDR. A humanized antibody may comprise substantially all of at least one, and typically two, variable domains (Fab, Fab', F(ab') 2, FabC, Fv) in which the sequence of all or substantially all of the CDR regions correspond to those of a non-human immunoglobulin (i.e., donor antibody) and the sequence of all or substantially all of the FR regions are those of a human immunoglobulin. The humanized antibody can also include the CH1, hinge, CH2, CH3, and CH4 regions of the heavy chain from a human antibody. In an embodiment, a humanized antibody also comprises at least a portion of a human immunoglobulin Fc region. In some embodiments, a humanized antibody only contains a humanized light chain. In some embodiments, a humanized antibody only contains a humanized heavy chain. In some embodiments, a humanized antibody only contains a humanized variable domain of a light chain and/or humanized variable domain of a heavy chain. In some embodiments, a humanized antibody contains a light chain as well as at least the variable domain of a heavy chain. In some embodiments, a humanized antibody contains a heavy chain as well as at least the variable domain of a light chain.

The terms "dual variable domain binding protein" and "dual variable domain immunoglobulin" refer to a binding protein that has two variable domains in each of its two binding arms (e.g., a pair of HC/LC) (see PCT Publication No. WO 02/02773), each of which is able to bind to an antigen. In an embodiment, each variable domain binds different antigens or epitopes. In another embodiment, each variable domain binds the same antigen or epitope. In another embodiment, a dual variable domain binding protein has two identical antigen binding arms, with identical specificity and identical CDR sequences, and is bivalent for each antigen to which it binds. In an embodiment, the DVD binding proteins may be monospecific, i.e., capable of binding one antigen or multispecific, i.e., capable of binding two or more antigens. DVD binding proteins comprising two heavy chain DVD polypeptides and two light chain DVD polypeptides are referred to as a DVD-Ig™. In an embodiment, each half of a four chain DVD binding protein comprises a heavy chain DVD polypeptide, and a light chain DVD polypeptide, and two antigen binding sites. In an embodiment, each binding site comprises a heavy chain variable domain and a light chain variable domain with a total of 6 CDRs involved in antigen binding per antigen binding site.

The term "antiidiotypic antibody" refers to an antibody raised against the amino acid sequence of the antigen combining site of another antibody. Antiidiotypic antibodies may be administered to enhance an immune response against an antigen.

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing other cytokines, inducing apoptosis, and enzymatic activity.

The term "neutralizing" refers to counteracting the biological activity of an antigen when a binding protein specifically binds to the antigen. In an embodiment, a neutralizing binding protein binds to an antigen (e.g., a cytokine) and reduces its biologically activity by at least about 20%, 40%, 60%, 80%, 85% or more.

"Specificity" refers to the ability of a binding protein to selectively bind an antigen.

"Affinity" is the strength of the interaction between a binding protein and an antigen, and is determined by the sequence of the CDRs of the binding protein as well as by the nature of the antigen, such as its size, shape, and/or charge. Binding proteins may be selected for affinities that provide desired therapeutic end-points while minimizing negative side-effects. Affinity may be measured using methods known to one skilled in the art (US 20090311253).

The term "potency" refers to the ability of a binding protein to achieve a desired effect, and is a measurement of its therapeutic efficacy. Potency may be assessed using methods known to one skilled in the art (US 20090311253).

The term "cross-reactivity" refers to the ability of a binding protein to bind a target other than that against which it was raised. Generally, a binding protein will bind its target tissue(s)/antigen(s) with an appropriately high affinity, but will display an appropriately low affinity for non-target normal tissues/antigens. Individual binding proteins are generally selected to meet two criteria: (1) antibody binding, as visualized using staining methods known in the art, to tissue appropriate for the known expression of the antibody target and (2) a similar staining pattern between human and tox species (e.g., mouse and cynomolgus monkey) tissues from the same organ. These and other methods of assessing cross-reactivity are known to one skilled in the art (US 20090311253).

The term "biological function" refers the specific in vitro or in vivo actions of a binding protein. Binding proteins may target several classes of antigens and achieve desired therapeutic outcomes through multiple mechanisms of action. Binding proteins may target soluble proteins, cell surface antigens, and/or extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve more than one distinct function in a single binding protein molecule. in vitro assays and in vivo models used to assess biological function are known to one skilled in the art (US 20090311253).

A "stable" binding protein is one in which the binding protein essentially retains its physical stability, chemical stability and/or biological activity upon storage. A multivalent binding protein that is stable in vitro at various temperatures for an extended period of time is desirable. Methods of stabilizing binding proteins and assessing their stability at various temperatures are known to one skilled in the art (US 20090311253).

The term "solubility" refers to the ability of a protein to remain dispersed within an aqueous solution. The solubility of a protein in an aqueous formulation depends upon the proper distribution of hydrophobic and hydrophilic amino acid residues, and therefore, solubility can correlate with the production of correctly folded proteins. A person skilled in the art will be able to detect an increase or decrease in solubility of a binding protein using routine HPLC techniques and methods known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art (US 20090311253).

The term "immunogenicity" means the ability of a substance to induce an immune response. Administration of a therapeutic binding protein may result in a certain incidence of an immune response. Potential elements that might induce immunogenicity in a multivalent format may be analyzed during selection of the parental antibodies, and steps to reduce such risk can be taken to optimize the parental antibodies prior to incorporating their sequences into a multivalent binding protein format. Methods of reducing the immunogenicity of antibodies and binding proteins are known to one skilled in the art (US 20090311253).

The terms "label" and "detectable label" mean a moiety attached to a member of a specific binding pair, such as an antibody or its analyte to render a reaction (e.g., a binding) between the members of the specific binding pair, detectable. The labeled member of the specific binding pair is referred to as "detectably labeled." Thus, the term "labeled binding protein" refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker, or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. In this regard, the moiety itself may not be detectably labeled but may become detectable upon reaction with yet another moiety.

The term "conjugate" refers to a binding protein, such as an antibody, that is chemically linked to a second chemical moiety, such as a therapeutic or cytotoxic agent. The term "agent" includes a chemical compound, a mixture of chemical compounds, a biological macromolecule, or an extract made from biological materials. Examples of therapeutic or cytotoxic agents include, but are not limited to, taxol, cytochalasin B, gramicidin D, emetine, mitomycin, etoposide, teniposide, vincristine, vinblastine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The terms "crystal" and "crystallized" refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, CRYSTALLIZATION OF NUCLEIC ACIDS AND PROTEINS, A PRACTICAL APPROACH, 2nd ea., pp. 20 1-16, Oxford University Press, New York, N.Y., (1999).

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Other vectors include RNA vectors. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, other forms of expression vectors are also included, such as viral vectors (e.g., replication defective retroviruses, adenoviruses and adeno-associated viruses), which serve equivalent functions. A group of pHybE vectors (U.S. Patent Application Ser. No. 61/021,282) can be used for parental antibody and DVD binding protein cloning. V1, derived from pJP183; pHybE-hCg1,z,non-a V2, can be used for cloning of antibody and DVD heavy chains with a wildtype constant region. V2, derived from pJP191; pHybE-hCk V3, can be used for cloning of antibody and DVD light chains with a kappa constant region. V3, derived from pJP192; pHybE-hCl V2, can be used for cloning of antibody and DVD light chains with a lambda constant region. V4, built with a lambda signal peptide and a kappa constant region, can be used for cloning of DVD light chains with a lambda-kappa hybrid V domain. V5, built with a kappa signal peptide and a lambda constant region, can be used for cloning of DVD light chains with a kappa-lambda hybrid V domain. V7, derived from pJP183; pHybE-hCg1,z,non-a V2, can be used for cloning of antibody and DVD heavy chains with a (234,235 AA) mutant constant region.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include, but are not limited to, the prokaryotic cell line *E. Coli*; mammalian cell lines CHO, HEK 293, COS, NS0, SP2 and PER.C6; the insect cell line Sf9; and the fungal cell *Saccharomyces cerevisiae*.

The term "transfection" encompasses a variety of techniques commonly used for the introduction of exogenous nucleic acid (e.g., DNA) into a host cell, e.g., electroporation, calcium-phosphate precipitation, DEAE-dextran transfection and the like.

The term "cytokine" refers to a protein released by one cell population that acts on another cell population as an intercellular mediator. The term "cytokine" includes proteins from natural sources or from recombinant cell culture and biologically active equivalents of the native sequence cytokines.

The term "biological sample" means a quantity of a substance from a living thing or formerly living thing. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "component" refers to an element of a composition. In relation to a diagnostic kit, for example, a component may be a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample. Thus, a "component" can include, in some embodiments, a polypeptide or other analyte as above, that is immobilized on a solid support, such as by binding to an anti-analyte (e.g., anti-polypeptide) antibody. In some embodiments, one or more components can be in solution or lyophilized.

"Control" refers to a composition that does not comprise an analyte ("negative control") or does comprise the analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

A "Pretreatment reagent," e.g., a lysis, precipitation and/or solubilization reagent, as used in a diagnostic assay as described herein, is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from an endogenous binding proteins present in the sample. A pretreatment reagent may be homogeneous (not requiring a separation step) or heterogeneous (requiring a separation step). In some embodiments, when using a heterogeneous pretreatment reagent, precipitated analyte-binding proteins are removed from the test sample prior to proceeding to the next step of the assay.

"Quality control reagents" in the context of immunoassays and kits described herein, include, but are not limited to, calibrators, controls, and sensitivity panels. One or more "calibrator(s)" or "standard(s)" are typically used in order to establish calibration (standard) curves for interpolation of the concentration of a target molecule, such as an antibody or an analyte. In some embodiments, a single calibrator, which is near a predetermined positive/negative cutoff, can be used. Alternatively, in other embodiments multiple calibrators (i.e., more than one calibrator or a varying amount of calibrator(s)) can be used to establish a "sensitivity panel" or a "sensitivity gradient"

The term "specific binding partner" refers to a member of a specific binding pair. A specific binding pair comprises two different molecules that specifically bind to each other through chemical or physical means. In various embodiments, in addition to antigen and antibody specific binding, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include, in some embodiments, members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

The term "Fc region" defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (e.g., U.S. Pat. Nos. 5,648,260 and 5,624,821). The Fc region mediates several important effector functions, e.g., cytokine induction, antibody dependent cell mediated cytotoxicity (ADCC), phagocytosis, complement dependent cytotoxicity (CDC), and the half-life/clearance rate of antibody and antigen-antibody complexes. In some cases these effector functions are desirable for a therapeutic immunoglobulin but in other cases might be unnecessary or even deleterious, depending on the therapeutic objectives.

The term "antigen-binding portion" of a binding protein means one or more fragments of a binding protein (e.g., an antibody) that retain the ability to specifically bind to an antigen. The antigen-binding function of a binding protein can be performed by fragments of a full-length antibody, as well as bispecific, dual specific, or multi-specific formats. Examples of binding fragments encompassed within the term "antigen-binding portion" of an binding protein include (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which comprises a single variable domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed. In addition, single chain antibodies also include "linear antibodies" comprising a pair of tandem Fv segments (VH-CH1-VH-CH1) which, together with complementary light chain polypeptides, form a pair of antigen binding regions.

The term "multivalent binding protein" means a binding protein comprising two or more antigen binding sites. In an embodiment, the multivalent binding protein is engineered to have three or more antigen binding sites, and is not a naturally occurring antibody. The term "multispecific binding protein" refers to a binding protein capable of binding two or more related or unrelated targets. In an embodiment, the DVD binding proteins provided herein comprise two or more antigen binding sites and are tetravalent or multivalent binding proteins.

The term "linker" means an amino acid residue or a polypeptide comprising two or more amino acid residues joined by peptide bonds that are used to link two polypeptides (e.g., two VH or two VL domains). Examples of such linker polypeptides are well known in the art (see, e.g., Holliger et al. (1993) Proc. Natl. Acad. Sci. USA 90:6444-6448; Poljak et al. (1994) Structure 2:1121-1123).

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "CDR" means a complementarity determining region within an immunoglobulin variable region sequence. There are three CDRs in each of the variable regions of the heavy chain and the light chain, which are designated CDR1, CDR2 and CDR3, for each of the heavy and light chain variable regions. The term "CDR set" refers to a group of three CDRs that occur in a single variable region capable of binding the antigen. The exact boundaries of these CDRs have been defined differently according to different systems. The system described by Kabat (Kabat et al. (1987) and (1991)) not only provides an unambiguous residue numbering system applicable to any variable region of an antibody, but also provides precise residue boundaries defining the three CDRs. These CDRs may be referred to as Kabat CDRs. Chothia and colleagues (Chothia and Lesk (1987) J. Mol. Biol. 196:901-917; Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The term "epitope" means a region of an antigen that is bound by a binding protein, e.g., a region capable of specifically binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In an embodiment, an epitope comprises the amino acid residues of a region of an antigen (or fragment thereof) known to bind to the complementary site on the specific binding partner. An antigenic fragment can contain more than one epitope. In certain embodiments, a binding protein specifically binds an antigen when it recognizes its target antigen in a complex mixture of proteins and/or macromolecules. Binding proteins "bind to the same epitope" if the antibodies cross-compete (e.g., one prevents the other from binding to the binding protein, or inhibits the modulating effect on the other of binding to the binding protein). The methods of visualizing and modeling epitope recognition are known to one skilled in the art (US 20090311253).

"Pharmacokinetics" refers to the process by which a drug is absorbed, distributed, metabolized, and excreted by an organism. In some embodiments, to generate a multivalent binding protein molecule with a desired pharmacokinetic profile, parent monoclonal antibodies with similarly desired pharmacokinetic profiles are selected. PK profiles of the selected parental monoclonal antibodies can be easily determined, for example using rodents in methods known to one skilled in the art (US 20090311253).

"Bioavailability" refers to the amount of active drug that reaches its target following administration. Bioavailability is function of several of the previously described properties, including stability, solubility, immunogenicity and pharmacokinetics, and can be assessed using methods known to one skilled in the art (US 20090311253).

The term "surface plasmon resonance" means an optical phenomenon that allows for the analysis of real-time biospecific interactions by detection of alterations in protein concentrations within a biosensor matrix, for example using the BIAcore® system (BIAcore International AB, a GE Healthcare Co., Uppsala, Sweden and Piscataway, N.J.). For further descriptions, see Jonsson et al. (1993) Ann. Biol. Clin. 51:19-26. The term "$K_{on}$" means the on rate constant for association of a binding protein (e.g., an antibody or DVD) to the antigen to form a bound complex (e.g., a DVD/antigen complex). The term "$K_{on}$" also means "association rate constant", or "ka", as is used interchangeably herein. This value indicating the binding rate of a binding protein to its target antigen or the rate of complex formation between a binding protein, (e.g., an antibody) and antigen. This is also shown by the equation below:

Antibody ("Ab")+Antigen ("Ag")→Ab-Ag

The term "$K_{off}$" means the off rate constant for dissociation, or "dissociation rate constant", of a binding protein (e.g., an antibody or DVD) from a bound complex (e.g., a DVD/antigen complex), as is known in the art. This value indicates the dissociation rate of a binding protein (e.g., an antibody)

from its target antigen or the separation of an Ab-Ag complex over time into free antibody and antigen, as shown by the equation below:

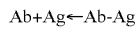

$$Ab+Ag \leftarrow Ab\text{-}Ag$$

The terms "$K_D$" and "equilibrium dissociation constant" means the value obtained in a titration measurement at equilibrium, or by dividing the dissociation rate constant ($K_{off}$) by the association rate constant ($K_{on}$). The association rate constant, the dissociation rate constant and the equilibrium dissociation constant, are used to represent the binding affinity of a binding protein (e.g., an antibody or DVD) to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

The term "variant" means a polypeptide that differs from a given polypeptide in amino acid sequence by the addition (e.g., insertion), deletion, or conservative substitution of amino acids, but that retains the biological activity of the given polypeptide (e.g., a variant VEGF antibody can compete with anti-VEGF antibody for binding to VEGF). A conservative substitution of an amino acid, i.e., replacing an amino acid with a different amino acid of similar properties (e.g., hydrophilicity and/or degree or distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). In one aspect, amino acids having hydropathic indexes of ±2 are substituted. The hydrophilicity of amino acids can also be used to reveal substitutions that would result in proteins that retain biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also includes polypeptides or fragments thereof that have been differentially processed, such as by proteolysis, phosphorylation, or other post-translational modification, yet retain biological activity and/or antigen reactivity, e.g., the ability to bind to VEGF and/or DLL4. The term "variant" encompasses fragments of a variant unless otherwise defined. A variant may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to the wild type sequence.

I. Generation of Binding Proteins

Binding proteins capable of binding two different antigens, and methods of making the same are provided. The binding protein can be generated using various techniques. Expression vectors, host cell and methods of generating the binding protein are also provided.

A. Generation of Parent Monoclonal Antibodies

The variable domains of the DVD binding protein can be obtained from parent antibodies (Abs), including polyclonal Abs and monoclonal Abs (mAbs) capable of binding antigens of interest. These antibodies may be naturally occurring or may be generated by recombinant technology. The person of ordinary skill in the art is well familiar with many methods for producing antibodies, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques.

B. Criteria for Selecting Parent Monoclonal Antibodies

An embodiment is provided comprising selecting parent antibodies with at least one or more properties desired in the DVD binding protein molecule. In an embodiment, the desired property is one or more antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

C. Binding Protein Molecules

In various embodiments, the binding protein may be designed such that two different light chain variable domains (VL) from the two different parent monoclonal antibodies are linked in tandem directly or via a linker by recombinant DNA techniques, followed by the light chain constant domain CL. Similarly, the heavy chain comprises two different heavy chain variable domains (VH) linked in tandem, directly or via a linker, followed by the constant domain CH1 and Fc region (FIG. 1).

In various embodiments, the variable domains can be obtained using recombinant DNA techniques from parent antibodies generated by any one of the methods described herein. In an embodiment, the variable domain is a murine heavy or light chain variable domain. In another embodiment, the variable domain is a CDR grafted or a humanized variable heavy or light chain domain. In an embodiment, the variable domain is a human heavy or light chain variable domain.

In various embodiments, the linker sequence may be a single amino acid or a polypeptide sequence. In an embodiment, the choice of linker sequences is based on crystal structure analysis of several Fab molecules. There is a natural flexible linkage between the variable domain and the CH1/CL constant domain in Fab or antibody molecular structure. This natural linkage generally comprises approximately 10-12 amino acid residues, contributed by 4-6 residues from the C-terminus of a V domain and 4-6 residues from the N-terminus of a CL/CH1 domain. In some embodiments, DVD binding proteins are generated using N-terminal 5-6 amino acid residues, or 11-12 amino acid residues, of a CL or CH1 as a linker in the light chain and heavy chains, respectively. The N-terminal residues of a CL or CH1 domains, particularly the first 5-6 amino acid residues, can adopt a loop conformation without strong secondary structures, and therefore can act as flexible linkers between the two variable domains.

The N-terminal residues of a CL or CH1 domains are natural extension of the variable domains, as they are part of the Ig sequences, and therefore their use minimizes to a large extent any immunogenicity potentially arising from the linkers and junctions.

In various embodiments, the binding proteins disclosed herein include at least one linker comprising one or more of SEQ ID NO: 1-38 (Table 1). In an embodiment, X2 is an Fc region. In another embodiment, X2 is a variant Fc region.

TABLE 1

List of Linker Sequences

| SEQ ID NO: | Sequence |
|---|---|
| 1 | ASTKGPSVFPLAP |
| 2 | ASTKGP |
| 3 | GGGGSG |
| 4 | GGGGSGGGGS |
| 5 | GGGGSGGGGSGGGG |
| 6 | TVAAPSVFIFPP |
| 7 | TVAAP |
| 8 | GGGGSG |
| 9 | GGSGGGGSG |
| 10 | GGSGGGGSGGGGS |
| 11 | GGSGG |
| 12 | GGSGGGGSGGGS |
| 13 | AKTTPKLEEGEFSEAR |
| 14 | AKTTPKLEEGEFSEARV |
| 15 | AKTTPKLGG |
| 16 | SAKTTPKLGG |
| 17 | SAKTTP |
| 18 | RADAAP |
| 19 | RADAAPTVS |
| 20 | RADAAAAGGPGS |
| 21 | RADAAAA |
| 22 | SAKTTPKLEEGEFSEARV |
| 23 | ADAAP |
| 24 | ADAAPTVSIFPP |
| 25 | TVAAP |
| 26 | TVAAPSVFIFPP |
| 27 | QPKAAP |
| 28 | QPKAAPSVTLFPP |
| 29 | AKTTPP |
| 30 | AKTTPPSVTPLAP |
| 31 | AKTTAP |

TABLE 1-continued

List of Linker Sequences

| SEQ ID NO: | Sequence |
|---|---|
| 32 | AKTTAPSVYPLAP |
| 33 | GGGGSGGGGSGGGGS |
| 34 | GENKVEYAPALMALS |
| 35 | GPAKELTPLKEAKVS |
| 36 | GHEAAAVMQVQYPAS |
| 37 | TVAAPSVFIFPPTVAAPSVFIFPP |
| 38 | ASTKGPSVFPLAPASTKGPSVFPLAP |

Other linker sequences may include any sequence of any length derived from a CL/CH1 domain but not all residues of a CL/CH1 domain; for example the first 5-12 amino acid residues of a CL/CH1 domain. In another example, the light chain linkers can be selected from Cκ or Cλ; and the heavy chain linkers can be derived from CH1 of any isotype, including Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR); G/S based sequences (e.g., G4S repeats (SEQ ID NO: 75)); hinge region-derived sequences; and other natural sequences from other proteins. Other linker sequences may include any sequence of any length comprising G/S repeats (e.g., a sequence comprising repeats of a GGGS motif (SEQ ID NO: 76)), or any other peptide linkers.

In an embodiment, a constant domain is linked to the two linked variable domains using recombinant DNA techniques. In an embodiment, a sequence comprising linked heavy chain variable domains is linked to a heavy chain constant domain and a sequence comprising linked light chain variable domains is linked to a light chain constant domain. In an embodiment, the constant domains are human heavy chain constant domains and human light chain constant domains respectively. In an embodiment, the DVD heavy chain is further linked to an Fc region. The Fc region may be a native sequence Fc region or a variant Fc region. In another embodiment, the Fc region is a human Fc region. In another embodiment, the Fc region includes Fc region from IgG1, IgG2, IgG3, IgG4, IgA, IgM, IgE, or IgD.

In another embodiment, two heavy chain DVD polypeptides and two light chain DVD polypeptides are combined to form a DVD binding protein. Table 2 lists amino acid sequences of VH and VL regions of exemplary antibodies useful for treating disease. In an embodiment, a DVD comprising at least two of the VH and/or VL regions listed in Table 2, in any orientation, is provided, wherein at least one of the VH and/or VL sequences is SEQ ID NO: 39 or SEQ ID NO: 40. In some embodiments, VD1 and VD2 are independently chosen. The VH and VL domain sequences provided below comprise complementarity determining regions (CDRs) and framework sequences. In some embodiments, one or more of these CDRs and/or framework sequences are replaced, without loss of function, by other CDRs and/or framework sequences from binding proteins that are known in the art to bind to the same antigen.

TABLE 2

List of Amino Acid Sequences of VH and VL Regions of Anti-DLL4 and Anti-VEGF Antibodies for Generating Binding Proteins, Including Multivalent Binding Proteins
(CDR sequences in bold)

| SEQ ID No. | ABT Unique ID | Protein region | Sequence<br>12345678901234567890123456789012345678 90 |
|---|---|---|---|
| 39 | h1A11.1 | DLL4 VH | EVQLVESGGGLVQPGGSLRLSCAASGFTFSNFPMAWVRQA PGKGLEWVATISSSDGTTYYRDSVKGRFTISRDNAKNSLY LQMNSLRAEDTAVYYCARGYYNSPFAYWGQGTLVTVSS |
| 40 | h1A11.1 | DLL4 VL | DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR |
| 41 | Av | VEGF VH (seq 1) | EVQLVESGGGLVQPGGSLRLSCAASGYTFTNYGMNWVRQAP GKGLEWVGWINTYTGEPTYAADFKRRFTFSLDTSKSTAYLQ MNSLRAEDTAVYYCAKYPHYYGSSHWYFDVWGQGTLVTVSS |
| 42 | Av | VEGF VL (seq 1) | DIQMTQSPSSLSASVGDRVTITCSASQDISNYLNWYQQKPG KAPKVLIYFTSSLHSGVPSRFSGSGSGTDFTLTISSLQPED FATYYCQQYSTVPWTFGQGTKVEIKR |
| 43 | AB285VH | VEGF VH (seq 2) | EVTLRESGPALVKPTQTLTLTCTASGYTFTNYGMNWVRQPP GKGLEWVGWINTYTGEPTYAADFKRRFTFSLDTSKSQAVLT MTNMDPVDTATYYCAKYPHYYGSSHWYFDVWGQGTTVTVSS |
| 44 | AB285VL | VEGF VL (seq 2) | DIVMTQSPDSLAVSLGERATINCSASQDISNYLNWYQQKPG QAPKVLIYFTSSLHSGVPDRFSGSGSGTDFTLTISSLQAED VAVYYCQQYSTVPWTFGGGTKVEIKR |
| 45 | AB288VH | VEGF VH (seq 3) | EVQLVQSGTEVKKPGESLKISCKASGYTFTNYGMNWVRQMP GKGLEWVGWINTYTGEPTYAADFKRQFTFSLDTSFSTAFLQ WSSLKASDTAMYYCAKYPHYYGSSHWYFDVWGQGTMVTVSS |
| 46 | AB288VL | VEGF VL (seq 3) | EIVMTQSPATLSVSPGERATLSCSASQDISNYLNWYQQKPG QAPRVLIYFTSSLHSDVPARFSGSGSGTEFTLTISSLQSED FAVYYCQQYSTVPWTFGQGTRLEIKR |
| 47 | AB305VH | VEGF VH (seq 4) | EVQLLESGGGLVQPGGSLRLSCAASGYTFTNYGMNWVRQAP GKGLEWVGWINTYTGEPTYAADFKRRFTFSLDTSKSTAYLQ MNSLRAEDTAVYYCAKYPHYYGSSHWYFDVWGQGTLVTVSS |
| 48 | AB305VL | VEGF VL (seq 4) | EIVMTQSPGTLSLSPGERATLSCSASQDISNYLNWYQQKPG QAPRVLIYFTSSLHSGVPDRFSGSGSGTDFTLTISRLEPED FAVFYCQQYSTVPWTFGQGTKVEIKR |
| 49 | AB308VH | VEGF VH (seq 5) | EVQLVESGGGLVQPGRSLRLSCAASGYTFTNYGMNWVRQAP GKGLEWVGWINTYTGEPTYAADFKRRFTFSLDTAKSSAYLQ MNSLRAEDTAVYYCAKYPHYYGSSHWYFDVWGQGTLVTVSS |
| 50 | AB308VL | VEGF VL (seq 5) | DIQMTQSPSSLSASVGDRVTITCSASQDISNYLNWYQQKPG KAPKVLIYFTSSLHSGVPSRFSGSGSGTDFTLTISSL QPEDVATYYCQQYSTVPWTFGQGTKVEIKR |
| 51 | AB318VH | VEGF VH (seq 6) | EVQLVESGGGLVQPANSLKLSCAASGYTFTNYGMNWVRQSP KKGLEWVGWINTYTGEPTYAADFKRRFTFSLDTAKSTAYLQ MDSLRSEDTATYYCAKYPHYYGSSHWYFDVWGQGVLVTVSS |
| 52 | AB318VL | VEGF VL (seq 6) | DIRMTQSPASLSASLGETVNIECSASQDISNYLNWYQQKPG KAPQVLIYFTSSLHSGVPSRFSGSGSGTQFSLKINSLQSED VATYYCQQYSTVPWTFGGGTKLELKR |
| 53 | AB333VH | VEGF VH (seq 7) | QVQLQQSGAELMKPGASVKLSCKATGYTFTNYGMNWVKQRP GHGLEWVGWINTYTGEPTYAADFKRKFTFTLDTSSSTAYIQ LISLTTEDSAIYYCAKYPHYYGSSHWYFDVWGQGTLLTVSA |
| 54 | AB333VL | VEGF VL (seq 7) | DILMTQSPAILSVSPGERVSFSCSASQDISNYLNWYQQRTN GAPRVLIYFTSSLHSGVPSRFSGGGSGTDFTLSINSVESED IADYYCQQYSTVPWTFGAGTKLELKR |

In some embodiments, DVD binding proteins are provided, comprising a VH region selected from SEQ ID NO: 55-63. In certain embodiments, a DVD binding protein comprises a VL region selected from SEQ ID NO: 64-73. In some embodiments, a DVD binding protein comprises a VH region selected from SEQ ID NO: 55-63 and 74 and a VL region selected from SEQ ID NO: 64-73. The amino acid sequences for these VH and VL domains are shown below in Table 3.

Table 3

DVD binding proteins directed against epitopes of DLL4 and VEGF (Linker sequence in italics; CDR sequences in bold)

| SEQ ID No. | ABT Unique ID | Protein region | Sequence 12345678901234567890123456789012345678 90 |
|---|---|---|---|
| 55 | h1A11.1-L-Av VH | DLL4 VH and VEGF VH | EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS*ASTKGPSVFPLAPE*VQLVESGGGLVQPGGSLRLSCAASSGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS |
| 56 | h1A11.1-S-Av VH | DLL4 VH and VEGF VH | EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS*ASTKGP*EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS |
| 57 | h1A11.1-GS10-Av VH | DLL4 VH and VEGF VH | EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS*GGGGSGGGGS*EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS |
| 58 | h1A11.1-GS14-Av VH | DLL4 VH and VEGF VH | EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS*GGGGSGGGGSGGGG*EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS |
| 59 | Av-L-h1A11.1 VH | VEGF VH and DLL4 VH | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS*ASTKGPSVFPLAPE*VQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS |
| 60 | Av-S-h1A11.1 VH | VEGF VH and DLL4 VH | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS*ASTKGP*EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS |
| 61 | Av-GS6-h1A11.1 VH | VEGF VH and DLL4 VH | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS*GGGGSG*EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS |
| 62 | Av-GS10-h1A11.1 VH | VEGF VH and DLL4 VH | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS*GGGGSGGGGS*EVQLVESGGGLVQPGGSLRLSCAASGFTFSNFPMAWVRQAPGKGLEWVATISSSDGTTYYRDSVKGRFTISRDNAKNSLYLQMNSLRAEDTAVYYCARGYYNSPFAYWGQGTLVTVSS |
| 63 | Av-GS14-h1A11.1 VH | VEGF VH and DLL4 VH | EVQLVESGGGLVQPGGSLRLSCAASGYTFTNYGMNWVRQAPGKGLEWVGWINTYTGEPTYAADFKRRFTFSLDTSKSTAY |

TABLE 3-continued

DVD binding proteins directed against epitopes of DLL4 and VEGF (Linker sequence in italics; CDR sequences in bold)

| SEQ ID No. | ABT Unique ID | Protein region | Sequence |
|---|---|---|---|
|  |  | DLL4 VH | LQMNSLRAEDTAVYYCAKYPHYYGSSHWYFDVWGQGTLVT VSS*GGGGSGGGGSGGGG*EVQLVESGGGLVQPGGSLRLSCA ASGFTFSNFPMAWVRQAPGKGLEWVATISSSDGTTYYRDS VKGRFTISRDNAKNSLYLQMNSLRAEDTAVYYCARGYYNS PFAYWGQGTLVTVSS |
| 64 | h1A11.1-L-Av VL | DLL4 VL and VEGF VL | DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR*TVAAPSVFIFPP* DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR |
| 65 | h1A11.1-S-Av VL | DLL4 VL and VEGF VL | DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR*TVAAP*DIQMTQS PSSLSASVGDRVTITCSASQDISNYLNWYQQKPGKAPKVL IYFTSSLHSGVPSRFSGSGSGTDFTLTISSLQPEDFATYY CQQYSTVPWTFGQGTKVEIKR |
| 66 | h1A11.1-GS10-Av VL | DLL4 VL and VEGF VL | DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR*GGSGGGGSG*DIQ MTQSPSSLSASVGDRVTITCSASQDISNYLNWYQQKPGKA PKVLIYFTSSLHSGVPSRFSGSGSGTDFTLTISSLQPEDF ATYYCQQYSTVPWTFGQGTKVEIKR |
| 67 | h1A11.1-GS14-Av VL | DLL4 VL and VEGF VL | DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR*GGSGGGGSGGGG SDIQ*MTQSPSSLSASVGDRVTITCSASQDISNYLNWYQQK PGKAPKVLIYFTSSLHSGVPSRFSGSGSGTDFTLTISSLQ PEDFATYYCQQYSTVPWTFGQGTKVEIKR |
| 68 | Av-L-h1A11.1 VL | VEGF VL and DLL4 VL | DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR*TVAAPSVFIFPP* DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR |
| 69 | Av-S-h1A11.1 VL | VEGF VL and DLL4 VL | DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR*TVAAP*DIQMTQS PSSLSASVGDRVTITCRASEDIYSNLAWYQQKPGKAPKLL IYDTNNLADGVPSRFSGSGSGTDFTLTISSLQPEDFATYY CQQYNNYPPTFGQGTKLEIKR |
| 70 | Av-GS6-h1A11.1 VL | VEGF VL and DLL4 VL | DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR*GGSGG*DIQMTQS PSSLSASVGDRVTITCRASEDIYSNLAWYQQKPGKAPKLL IYDTNNLADGVPSRFSGSGSGTDFTLTISSLQPEDFATYY CQQYNNYPPTFGQGTKLEIKR |
| 71 | Av-GS10-h1A11.1 VL | VEGF VL and DLL4 VL | DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR*GGSGGGGSG*DIQ MTQSPSSLSASVGDRVTITCRASEDIYSNLAWYQQKPGKA PKLLIYDTNNLADGVPSRFSGSGSGTDFTLTISSLQPEDF ATYYCQQYNNYPPTFGQGTKLEIKR |
| 72 | Av-GS14-h1A11.1 VL | VEGF VL and DLL4 VL | DIQMTQSPSSLSASVGDRVTITCSASQDISNYLNWYQQKP GKAPKVLIYFTSSLHSGVPSRFSGSGSGTDFTLTISSLQP EDFATYYCQQYSTVPWTFGQGTKVEIKR*GGSGGGGSGGGGS* DIQMTQSPSSLSASVGDRVTITCRASEDIYSNLAWYQQKP GKAPKLLIYDTNNLADGVPSRFSGSGSGTDFTLTISSLQP EDFATYYCQQYNNYPPTFGQGTKLEIKR |

TABLE 3a

Full length binding proteins directed
against epitopes of DLL4 and VEGF

| | | |
|---|---|---|
| 73 | h1A11.1-<br>SL-Av<br>light<br>chain | DIQMTQSPSSLSASVGDRVTITCRASEDIYSNLAWY<br>QQKPGKAPKLLIYDTNNLADGVPSRFSGSGSGTDFT<br>LTISSLQPEDFATYYCQQYNNYPPTFGQGTKLEIKR<br>TVAAPSVFIFPPDIQMTQSPSSLSASVGDRVTITCS<br>ASQDISNYLNWYQQKPGKAPKVLIYFTSSLHSGVPS<br>RFSGSGSGTDFTLTISSLQPEDFATYYCQQYSTVPW<br>TFGQGTKVEIKRTVAAPSVFIFPPSDEQLKSGTASV<br>VCLLNNFYPREAKVQWKVDNALQSGNSQESVTEQDS<br>KDSTYSLSSTLTLSKADYEKHKVYACEVTHQGLSSP<br>VTKSFNRGEC |
| 74 | h1A11.1-<br>SL-Av<br>heavy<br>chain | EVQLVESGGGLVQPGGSLRLSCAASGFTFSNFPMAWV<br>RQAPGKGLEWVATISSSDGTTYYRDSVKGRFTISRDN<br>AKNSLYLQMNSLRAEDTAVYYCARGYYNSPFAYWGQG<br>TLVTVSSASTKGPEVQLVESGGGLVQPGGSLRLSCAA<br>SGYTFTNYGMNWVRQAPGKGLEWVGWINTYTGEPTYA<br>ADFKRRFTFSLDTSKSTAYLQMNSLRAEDTAVYYCAK<br>YPHYYGSSHWYFDVWGQGTLVTVSSASTKGPSVFPLA<br>PSSKSTSGGTAALGCLVKDYFPEPVTVSWNSGALTSG<br>VHTFPAVLQSSGLYSLSSVVTVPSSSLGTQTYICNVN<br>HKPSNTKVDKKVEPKSCDKTHTCPPCPAPEAAGGPSV<br>FLFPPKPKDTLMISRTPEVTCVVVDVSHEDPEVKFNW<br>YVDGVEVHNAKTKPREEQYNSTYRVVSVLTVLHQDWL<br>NGKEYKCKVSNKALPAPIEKTISKAKGQPREPQVYTL<br>PPSREEMTKNQVSLTCLVKGFYPSDIAVEWESNGQPE<br>NNYKTTPPVLDSDGSFFLYSKLTVDKSRWQQGNVFSC<br>SVMHEALHNHYTQKSLSLSPGK |

Table 3a provides the full-length heavy and light chan sequences for binding proteins directed against VEGF and DLL4. Linker sequences are underlined, while constant region sequences are in bold.

Detailed descriptions of specific DVD binding proteins capable of binding specific targets, and methods of making the same, are provided in the Examples section below.

D. Production of Binding Proteins

The binding proteins provided herein may be produced by any of a number of techniques known in the art. For example, the binding proteins can be expressed in host cells, wherein expression vector(s) encoding the DVD heavy and DVD light chains is (are) transfected into a host cell by standard techniques. In some embodiments, the DVD binding proteins provided herein are expressed in prokaryotic host cells. In other embodiments, the DVD binding proteins are expressed in eukaryotic cells, for example, mammalian host cells.

In an exemplary system for recombinant expression of DVD proteins, a recombinant expression vector encoding both the DVD heavy chain and the DVD light chain is introduced into DHFR-CHO cells by calcium phosphate-mediated transfection. Within the recombinant expression vector, the DVD heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected host cells are cultured to allow for expression of the DVD heavy and light chains and intact DVD protein is recovered from the culture medium. Standard molecular biology techniques are used to prepare the recombinant expression vector, transfect the host cells, select for transformants, culture the host cells and recover the DVD protein from the culture medium. In various embodiments, a method of synthesizing a DVD protein by culturing a host cell in a suitable culture medium until a DVD protein is synthesized is also provided herein. In some embodiments, the method can further comprise isolating the DVD protein from the culture medium.

A feature of a DVD binding protein is that it can be produced and purified in a similar way to a conventional antibody. In some embodiments, the production of a DVD binding protein results in a homogeneous, single major product with desired dual-specific activity, without the need for sequence modification of the constant region or chemical modifications. Other previously described methods to generate "bi-specific", "multi-specific", and "multi-specific multivalent" full length binding proteins can lead to the intracellular or secreted production of a mixture of assembled inactive, mono-specific, multi-specific, multivalent, full length binding proteins, and multivalent full length binding proteins with a combination of different binding sites.

In some embodiments, the design of the DVD proteins provided herein leads to a dual variable domain light chain and a dual variable domain heavy chain that assemble primarily to the desired "dual-specific multivalent full length binding proteins" after expression in host cells.

In some embodiments, at least 50%, at least 75% or at least 90% (or any percentage in between) of the expressed and assembled dual variable domain immunoglobulin molecules are the desired dual-specific tetravalent protein, and therefore possess enhanced commercial utility. Thus, in certain embodiments, a method to express a dual variable domain light chain and a dual variable domain heavy chain in a single cell leading to a single primary product of a "dual-specific tetravalent full length binding protein" is provided.

In various embodiments, methods of expressing a dual variable domain light chain and a dual variable domain heavy chain in a single cell leading to a "primary product" of a "dual-specific tetravalent full length binding protein", where the "primary product" is more than 50%, such as more than 75% or more than 90% (or any percentage in between), of all assembled protein, comprising a dual variable domain light chain and a dual variable domain heavy chain are provided.

II. Uses of Binding Proteins

Given their ability to bind to one, two, or more antigens, the binding proteins provided herein can be used, in certain embodiments, to detect the antigen(s) in a sample (e.g., a biological sample, such as serum or plasma), using a conventional immunoassay, such as an enzyme linked immunosorbent assays (ELISA), a radioimmunoassay (RIA), or tissue immunohistochemistry. In some embodiments, the binding protein is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin. An example of a luminescent material is luminol and examples of suitable radioactive materials include $^{3}$H, $^{14}$C $^{35}$S, $^{90}$Y, $^{99}$Tc, $^{111}$In, $^{125}$I, $^{131}$I, $^{177}$Lu, $^{166}$Ho, and $^{153}$Sm.

In various embodiments, the binding proteins provided herein are capable of neutralizing the activity of their antigen targets in vitro and/or in vivo. Accordingly, in certain embodiments the binding proteins can be used to inhibit antigen activity, e.g., in a cell culture containing the antigens, in human subjects, or in other mammalian subjects who have the antigens with which a binding protein cross-reacts. In another embodiment, a method for reducing antigen activity in a human or non-human animal subject suffering from a disease or disorder in which the antigen is detrimental is provided. In various embodiments, a binding protein provided herein can be administered to a human or non-human animal subject for diagnostic or therapeutic purposes (e.g., to detect or treat a disease, such as a disease characterized by abherrant VEGF and/or DLL4 expression).

As used herein, the term "a disorder in which antigen activity is detrimental" is intended to include diseases and/or other disorders in which the presence of the antigen in a subject suffering from the disorder has been shown to be or is suspected of being responsible for the pathophysiology of the disorder and/or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc., of the subject). Non-limiting examples of disorders that can be treated with the binding proteins provided herein include those disorders discussed below and in the section pertaining to pharmaceutical compositions comprising the binding proteins.

In various embodiments, DVD binding proteins are useful as therapeutic agents to increase the binding to a detrimental antigens and/or to simultaneously block two different antigen targets (DLL4 and/or VEGF) to enhance efficacy/safety and/or increase patient coverage.

Additionally, in some embodiments, DVD binding proteins provided herein can be employed for tissue-specific delivery (e.g., to target a tissue marker and/or a disease mediator for enhanced local PK, thus providing higher efficacy and/or lower toxicity), including intracellular delivery (e.g., targeting a DVD to an intracellular molecule). In some embodiments, DVD binding proteins can also serve as carrier proteins to deliver antigens to a specific location via binding to a non-neutralizing epitope of that antigen and also to increase the half-life of the antigen. Furthermore, a DVD binding protein can be designed, in certain embodiments, to either be physically linked to medical devices implanted into patients or to target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397).

A. Use of Binding Proteins in Various Diseases

In various embodiments, the binding proteins provided herein are useful as therapeutic molecules to treat various diseases or disorders, e.g., diseases or disorders associated with detrimental expression or expression levels of DLL4 and/or VEGF. In some embodiments, one or more binding proteins can be administered to diagnose, treat or enhance anti-tumor therapies and/or may be beneficial in the treatment of primary and/or metastatic cancers. In various embodiments, one or more binding proteins can be administered to diagnose, treat or enhance treatment an oncologic condition. In other embodiments, one or more binding proteins can be administered to diagnose, treat or enhance treatment of any other disease or disorder characterized by abherrant angiogenesis (e.g., general autoimmune and inflammatory disorders, wound healing). In various embodiments, administration of one or more binding proteins leads to binding to VEGF and/or DLL4, which may neutralize or otherwise reduce the levels of VEGF and/or DLL4 in a patient suffering from a condition characterized by excessive VEGF and/or DLL4 levels.

Without limiting the disclosure, further information on certain disease conditions is provided.

1. Oncological Disorders

Monoclonal antibody therapy has emerged as an important therapeutic modality for cancer (von Mehren et al. (2003) Annu. Rev. Med. 54:343-69). The use of a dual-specific antibody, as disclosed herein, that targets two separate oncongenic mediators, will likely provide additional benefit compared to a mono-specific therapy.

In various embodiments, oncologic diseases that can be diagnosed and/or treated with the compositions and methods provided herein include, but are not limited to, primary or metastatic cancer, breast cancer, colon cancer, rectum cancer, lung cancer, non-small cell lung cancer, adenocarcinoma, oropharynx cancer, hypopharynx cancer, esophageal cancer, stomach cancer, pancreatic cancer, liver cancer, gallbladder cancer, bile duct cancer, small intestine cancer, urinary tract cancer (including kidney, bladder and urothelium), female genital tract cancer (including cervix, uterus, and ovaries as well as choriocarcinoma and gestational trophoblastic disease), male genital tract cancer (including prostate, seminal vesicles, testes and germ cell tumors), endocrine gland cancer (including the thyroid, adrenal, and pituitary glands), skin cancer, hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas), stomach cancer, bladder cancer, prostate cancer, rectal cancer, hematopoietic malignancies, leukemia, lymphoma, Abetalipoprotemia, acrocyanosis, acute and chronic parasitic or infectious processes, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), colorectal carcinoma, hairy cell leukemia, Hodgkin's disease, Kaposi's sarcoma, malignant lymphoma, malignant histiocytosis, malignant melanoma, multiple myeloma, non-hodgkins lymphoma, pancreatic carcinoma, paraneoplastic syndrome/hypercalcemia of malignancy, sarcomas, solid tumors, or any other angiogenesis independent or dependent diseases characterized by aberrant DLL4 or VEGF activity.

In various embodiments, DVD binding proteins that bind DLL4 and/or VEG, or antigen-binding portions thereof, are used to diagnose and/or to treat cancer and/or to prevent metastasis, either when used alone or in combination with radiotherapy and/or other chemotherapeutic agents.

2. Macular Degeneration

In various embodiments, the compositions and methods provided herein can be used to treat macular degeneration, including neovascular (wet) macular degeneration. Macular degeneration is a medical condition that results in a loss of vision in the center of the visual field due to retina damage. Neovascular (wet) macular degeneration results from abnormal blood vessel growth, ultimately leading to blood and protein leakage below the macula that can cause irreversible damage to the photoreceptors.

In various embodiments, DVDs that bind DLL4 and/or VEGF, or antigen-binding portions thereof, are used to diagnose and/or to treat macular degeneration, either when used alone or in combination with other therapeutic agents.

3. Diabetes and Diabetic Retinopathy

Diabetes mellitus type 1 is a form of diabetes mellitus that results from autoimmune destruction of insulin-producing beta cells in the pancreas. The subsequent lack of insulin leads to increased blood and urine glucose. Diabetic retinopathy involves damage to the retina as a complication of diabetes.

Diabetic retinopathy is the result of small changes in the vascular system of the retina that result from hyperglycemia-induced pericyte death and weakening of the vascular walls. As the disease progresses, severe nonproliferative diabetic retinopathy enters an advanced stage where blood vessels proliferate. Without treatment, the new blood vessels can bleed, cloud vision, and further damage the retina. Fibrovascular proliferation can also cause retinal detachment. The proliferating blood vessels can also grow into the anterior chamber of the eye and cause neovascular glaucoma.

VEGF and DLL4 signaling are believed to play important roles in mediating diabetic endothelial dysfunction and vasculopathy, including involvement in the pathogenesis of both diabetic nephropathy and retinopathy. *J. Exp. Med.* 209(5): 1011-28 (2012); *Nephrol. Dial. Transplant.* 18 (8): 1427-1430 (2003); *PNAS* 109(27): E1868-77 (2012); US Patent Application No. 20110189176 (Skokos et al). Thus, VEGF and DLL4 may represent potential targets for diagnosis and/or therapy for diabetes and/or diabetic retinopathy using a DVD of the present disclosure (e.g., to identify serum levels and/or to alter levels of VEGF and/or DLL4 in a patient). In various embodiments, DVDs that bind DLL4 and/or VEGF, or antigen-binding portions thereof, are used to diagnose and/or to treat diabetes mellitus type 1 and/or diabetic retinopathy, either when used alone or in combination with other therapeutic agents.

4. Atherosclerosis

VEGF and DLL4 are believed to be involved in the progression of atherosclerosis. *Circulation* 98(20):2108-16 (1998); *PNAS* 109(27): E1868-77 (2012). In particular, VEGF expression has been shown in atherosclerotic lesions in human coronary arteries, suggesting a role for VEGF in the progression of human coronary atherosclerosis, as well as in recanalization processes in obstructive coronary diseases. Similarly, inhibition of DLL4 signaling using a neutralizing anti-DLL4 antibody has been shown to attenuate the development of atherosclerosis and diminishes plaque calcification. Thus, VEGF and DLL4 levels may represent potential targets for diagnosis and/or therapy for atherosclerosis using a DVD of the present disclosure (e.g., to identify serum levels and/or to alter levels of VEGF and/or DLL4 in a patient). In various embodiments, DVDs that bind DLL4 and/or VEGF, or antigen-binding portions thereof, are used to diagnose and/or to treat atherosclerosis, either when used alone or in combination with other therapeutic agents.

III. Pharmaceutical Compositions

In various embodiments, pharmaceutical compositions comprising one or more binding proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

Methods of administering a prophylactic or therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a binding protein provided herein is about 0.1-100 mg/kg, (e.g., about 0.1-0.5, 0.1-1, 0.1-10, 0.1-20, 0.1-50, 0.1-75, 1-10, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the binding protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

IV. Combination Therapy

In various embodiments, a binding protein provided herein can also be administered alone or in combination with one or more additional therapeutic agents used to treat a disease or disorder, e.g., a disease or disorder associated with detrimental expression or expression levels of DLL4 and/or VEGF. In some embodiments, the one or more binding proteins can be administered in combination with one or more therapeutic agents to diagnose, treat or enhance anti-tumor therapies and/or to treat primary and/or metastic cancers. In various embodiments, one or more binding proteins can be administered in combination with one or more therapeutic agents to diagnose, treat or enhance treatment an oncologic condition. In other embodiments, one or more binding proteins can be administered in combination with one or more therapeutic agents to diagnose, treat or enhance treatment of any other disease or disorder characterized by abherrant angiogenesis (e.g., general autoimmune and inflammatory disorders, wound healing). In various embodiments, administration of one or more binding proteins in combination with one or more therapeutic agents leads to a neutralization or other reduction in the levels of VEGF and/or DLL4 in a patient suffering from a condition characterized by excessive VEGF and/or DLL4 levels, as well as other therapeutic changes resulting from administration of the binding proteins and/or one or more therapeutic agents.

In various embodiments, the one or more additional agents is selected by the skilled artisan for its intended purpose. For example, the additional agent can be a therapeutic agent recognized in the art as being useful to treat cancer. The combination therapy can also include more than one additional agent, e.g., two, three, four, five, or more additional agents.

In various embodiments, combination therapy agents include, but are not limited to, antiangiogenic agents, antineoplastic agents, radiotherapy, chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), and siRNAs.

Non-limiting examples of chemotherapeutic agents with which binding proteins provided herein can be combined include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Anmidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine; Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Efudex®; Eligard™; Ellence™; Eloxatin™; Elspar®; Emcyt®; Epirubicin; Epoetin Alfa; Erbitux; Erlotinib; *Erwinia* L-asparaginase; Estramustine; Ethyol; Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol®; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; Iressa®; Irinotecan; Isotretinoin; Ixabepilone; Ixempra™; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Novantrone®; Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pentostatin; Phenylalanine Mustard; Platinol®; Platinol-AQ®; Prednisolone; Prednisone; Prelone®; Procarbazine; PROCRIT®; Proleukin®; Prolifeprospan 20 with Carmustine Implant; Purinethol®; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tretinoin; Trexall™; Trisenox®; TSPA; TYKERB®; VCR; Vectibix™; Velban®; Velcade®; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®.

In an embodiment, the binding proteins provided herein are used in combination with one or more of: Temozolomide®, irinotecan, leucovorin, 5-FU, gemcitabine, and paclitaxel. In an embodiment, binding protein h1A11.1-SL-Av is used in combination with one or more of: Temozolomide®, irinotecan, leucovorin, 5-FU, gemcitabine, and paclitaxel.

In various embodiments, the binding proteins provided herein may also be combined with an agent, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, a corticosteroid (oral, inhaled and local injection), a beta-2 adrenoreceptor agonist (salbutamol, terbutaline, salmeteral), a xanthine (theophylline, aminophylline), cromoglycate, nedocromil, ketotifen, ipratropium, oxitropium, cyclosporin, FK506, rapamycin, mycophenolate mofetil, leflunomide, an NSAID, for example, ibuprofen, a corticosteroid such as prednisolone, a phosphodiesterase inhibitor, an adensosine agonist, an antithrombotic agent, a complement inhibitor, an adrenergic agent, an agent which interferes with signalling by proinflammatory cytokines such as TNF-α or IL-1 (e.g., IRAK, NIK, IKK, p38 or a MAP kinase inhibitor), an IL-1β converting enzyme inhibitor, a TNFα converting enzyme (TACE) inhibitor, a T-cell signalling inhibitor such as a kinase inhibitor, a metalloproteinase inhibitor, sulfasalazine, azathioprine, a 6-mercaptopurine, an angiotensin converting enzyme inhibitor, a soluble cytokine receptor or derivative thereof (e.g., a soluble p55 or p75 TNF receptor or the derivative p75TNFRIgG (Enbrel™) or p55TNFRIgG (Lenercept), sIL-1RI, sIL-1RII, sIL-6R), an antiinflammatory cytokine (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, or Mesopram. In some embodiments, combinations can include methotrexate or leflunomide and cyclosporine.

In some embodiments, the pharmaceutical compositions provided herein may include a "therapeutically effective amount" or a "prophylactically effective amount" of a binding protein provided herein. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the antibody, or antibody binding portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

V. Diagnostics

The disclosure herein also provides diagnostic applications, including, but not limited to, diagnostic assay methods using one or more binding proteins, diagnostic kits containing one or more binding proteins, and methods and kits for use in automated and/or semi-automated systems. In some embodiments, the methods and kits can be employed in the detection, monitoring, and/or treatment of a disease or disorder in an individual.

A. Assay Method

In various embodiments, methods are provided for determining the presence, amount and/or concentration of at least one analyte, or fragment thereof, in a test sample using at least one binding protein. Exemplary assays include, but are not limited to, immunoassays and/or methods employing mass spectrometry.

For example, immunoassays provided by the present disclosure may include sandwich immunoassays, radioimmunoassays (RIA), enzyme immunoassays (EIA), enzyme-linked immunosorbent assays (ELISA), competitive-inhibition immunoassays, fluorescence polarization immunoassays (FPIA), enzyme multiplied immunoassay techniques (EMIT), bioluminescence resonance energy transfer (BRET), and homogenous chemiluminescent assays, among others.

In some embodiments, a method of determining the presence, amount or concentration of one or more antigens, or fragments thereof, in a test sample is provided, wherein the one or more antigens or fragments thereof are DLL4 and/or VEGF. The method comprises assaying the test sample for the antigen, or fragment thereof, by an immunoassay. The immunoassay (i) employs at least one binding protein and at least one detectable label and (ii) comprises comparing a signal generated by the detectable label as a direct or indirect indication of the presence, amount or concentration of the antigen, or fragment thereof, in the test sample to a signal generated as a direct or indirect indication of the presence, amount or concentration of the antigen, or fragment thereof, in a control or a calibrator. The calibrator is optionally part of a series of calibrators in which each of the calibrators differs from the other calibrators in the series by the concentration of the antigen, or fragment thereof. The method can comprise (i) contacting the test sample with at least one capture agent, which binds to an epitope on the antigen, or fragment thereof, so as to form a complex comprising the capture agent and the antigen or fragment thereof (ii) contacting the complex comprising the capture agent and the antigen or fragment thereof with at least one detection agent, which comprises a detectable label and binds to an epitope on the antigen, or fragment thereof, that is not bound by the capture agent, to form a detection complex, and (iii) determining the presence, amount or concentration of the antigen, or fragment thereof, in the test sample based on the signal generated by the detectable label in the detection complex formed in (ii), wherein at least one capture agent and/or at least one detection agent is the at least one binding protein.

Alternatively, in some embodiments, the method of determining the presence, amount or concentration of one or more antigens, or fragments thereof, in a test sample can comprise (i) contacting the test sample with at least one capture agent, which binds to an epitope on the antigen, or fragment thereof, so as to form a complex comprising the capture agent and the antigen or fragment thereof and simultaneously or sequentially, in either order, contacting the test sample with detectably labeled antigen, or fragment thereof, which can compete with any antigen, or fragment thereof, in the test sample for binding to the at least one capture agent, wherein any antigen, or fragment thereof, present in the test sample and the detectably labeled antigen compete with each other to form a detection complex and (ii) determining the presence, amount or concentration of the antigen, or fragment thereof, in the test sample based on the signal generated by the detectable label in the detection complex formed in (i), wherein at least one capture agent is the at least one binding protein and wherein the signal generated by the detectable label in the capture detection complex is inversely proportional to the amount or concentration of antigen, or fragment thereof, in the test sample.

In various embodiments, the test sample can be from a patient, in which case the method can further comprise diagnosing, prognosticating, or assessing the efficacy of therapeutic/prophylactic treatment of the patient. If the method further comprises assessing the efficacy of therapeutic/prophylactic treatment of the patient, the method optionally further comprises modifying the therapeutic/prophylactic treatment of the patient as needed to improve efficacy. The method can be adapted for use in an automated system or a semi-automated system. Accordingly, the methods described herein also can be used to determine whether or not a subject has or is at risk of developing a given disease, disorder or condition. Specifically, such a method can comprise the steps of:

(a) determining the concentration or amount of one or more analytes, or fragments thereof, in a test sample from a subject (e.g., using the methods described herein, or methods known in the art); and (b) comparing the concentration or amount of the analyte(s), or fragment(s) thereof, as determined in step (a) with a predetermined level, wherein, if the concentration or amount of analyte(s) determined in step (a) is favorable with respect to a predetermined level, then the subject is determined not to have or be at risk for a given disease, disorder or condition. However, if the concentration or amount of analyte(s) determined in step (a) is unfavorable with respect to the predetermined level, then the subject is determined to have or be at risk for a given disease, disorder or condition.

Additionally, provided herein are methods of monitoring the progression of a disease in a subject. In some embodiments, the methods comprise the steps of:
(a) determining the concentration or amount in a test sample from a subject of one or more analyte(s);
(b) determining the concentration or amount of analyte(s) in a later test sample from the same subject; and
(c) comparing the concentration or amount of analyte(s) as determined in step (b) with the concentration or amount of analyte(s) determined in step (a), wherein if the concentration or amount determined in step (b) is unchanged or is unfavorable when compared to the concentration or amount determined in step (a), then the disease in the subject is determined to have continued, progressed or worsened. By comparison, if the concentration or amount as determined in step (b) is favorable when compared to the concentration or amount as determined in step (a), then the disease in the subject is determined to have discontinued, regressed or improved.

Optionally, the methods of monitoring the progression of a disease further comprises comparing the concentration or amount of analyte(s) as determined in step (b), for example, with a predetermined level. Further, optionally the methods comprise treating the subject with one or more pharmaceutical compositions for a period of time if the comparison shows that the concentration or amount of analyte(s) as determined in step (b), for example, is unfavorably altered with respect to the predetermined level.

In some embodiments, the presence, amount, or concentration of an analyte or fragment thereof is detected in a sample using a detectable label such as a chemiluminescent label (acridinium compound). In some embodiments, the chemiluminescent signal that is generated can be detected using routine techniques known to those skilled in the art. Based on the intensity of the signal generated, the amount or concentration of analyte in the sample can be quantified. Specifically, in some embodiments, the amount of analyte in the sample may be proportional to the intensity of the signal generated. In certain embodiments, the amount of analyte present can be quantified by comparing the amount of light generated to a standard curve for analyte or by comparison to a reference standard or calibrator. The standard curve can be generated using serial dilutions or solutions of known concentrations of analyte by mass spectroscopy, gravimetric methods, and other techniques known in the art.

Analyte immunoassays generally can be conducted using any format known in the art, such as, but not limited to, a sandwich format. For example, in the immunoassays one or more binding proteins can be used to capture the analyte (or a fragment thereof) in the test sample (these binding proteins are frequently referred to as a "capture" binding proteins) and one or more binding proteins can be used to bind a detectable (namely, quantifiable) label to the sandwich (these binding proteins are frequently referred to as the "detection" binding proteins, the "conjugate," or the "conjugates"). Thus, in the context of an exemplary sandwich immunoassay format, a DVD (or a fragment, a variant, or a fragment of a variant thereof) as described herein can be used as a capture binding protein, a detection binding protein, or both. For example, a DVD having a first domain that can bind an epitope on a first analyte (or a fragment thereof) and a second domain that can bind an epitope on a second analyte (or a fragment thereof) can be used as a capture and/or detection binding protein to detect, and optionally quantify, one or more analytes (e.g., DLL4 and/or VEGF). In a further example, employing DVD having differential affinities within a sandwich assay can provide an avidity advantage. In the context of immunoassays as described herein, it generally may be helpful or desired to incorporate one or more linkers within the structure of a DVD. When present, optimally the linker should be of sufficient length and structural flexibility to enable binding of an epitope by the inner domains as well as binding of another epitope by the outer domains. In this regard, if a DVD can bind two different analytes and one analyte is larger than the other, desirably the larger analyte is bound by the outer domains.

In various embodiments, a sample being tested (e.g., a sample suspected of containing analyte or a fragment thereof) can be contacted with at least one capture binding protein and at least one detection binding protein either simultaneously or sequentially and in any order. For example, the test sample can first be contacted with at least one capture binding protein and then (sequentially) with at least one detection binding protein. Alternatively, the test sample can be first contacted with at least one detection binding protein and then (sequentially) with at least one capture binding protein. In yet another alternative, the test sample can be contacted simultaneously with a capture binding protein and a detection binding protein. In various embodiments, competitive inhibition immunoassays comprising one or more DVD disclosed herein can be used to detect the presence, amount, or concentration of one or more analytes or fragments thereof (e.g., DLL4 and/or VEGF).

In various embodiments, the detectable label can be bound to the binding proteins either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to a binding protein are known in the art.

In various embodiments, the presence or amount of label bound to a complex comprising analyte and DVD in a detection assay can be quantified using techniques known in the art. For example, if an enzymatic label is used, the labeled complex can be reacted with a substrate for the label that gives a quantifiable reaction such as the development of color. If the label is a radioactive label, the label can be quantified using appropriate means, such as a scintillation counter. If the label is a fluorescent label, the label can be quantified by stimulating the label and detecting a fluorescent signal. If the label is a chemiluminescent label, the label can be quantified by detecting the light emitted either visually or by using luminometers, x-ray film, high speed photographic film, a CCD camera, etc. In some embodiments, once the amount of the label in the complex has been quantified, the concentration of analyte or a fragment thereof in the test sample can determined by appropriate means, such as by use of a standard curve that has been generated using serial dilutions of analyte or a fragment thereof of known concentration or by any other calibrator.

In an embodiment, a chemiluminescent microparticle immunoassay, in particular one employing the ARCHITECT® automated analyzer (Abbott Laboratories, Abbott Park, Ill.), is used.

In some embodiments, methods employing mass spectrometry are provided by the present disclosure and include, but are not limited to MALDI (matrix-assisted laser desorption/ionization) and SELDI (surface-enhanced laser desorption/ionization).

Methods for collecting, handling, processing, and analyzing biological test samples using immunoassays and mass spectrometry are well-known to one skilled in the art and are provided for in the practice of the present disclosure (US 2009-0311253 A1).

B. Kit

In various embodiments, a kit for assaying a test sample for the presence, amount and/or concentration of at least one analyte, or fragment thereof, in a test sample is also provided. In some embodiments, the kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or a fragment, a variant, or a fragment of a variant thereof. In some embodiments, the component is optionally immobilized on a solid phase.

Optionally, in some embodiments, the kit may comprise a calibrator or control, which may comprise isolated or purified analyte. In certain embodiments, the kit can comprise at least one component for assaying the test sample for an analyte by immunoassay and/or mass spectrometry. The kit components, including the analyte, binding protein, and/or anti-analyte binding protein, or fragments thereof, may be optionally labeled using any art-known detectable label (US 2009-0311253 A1).

C. Automation

In various embodiments, the kits (or components thereof) and the methods of determining the presence, amount and/or concentration of at least one analyte in a test sample can be adapted for use in a variety of automated and semi-automated systems, as described, for example, in U.S. Pat. Nos. 5,089,424 and 5,006,309, and as commercially marketed, for example, by Abbott Laboratories (Abbott Park, Ill.) as ARCHITECT®.

Other automated or semiautomated platforms that could be used with the binding proteins include, but are not limited to, AxSYM®, IMx® (see, for example, U.S. Pat. No. 5,294,404, PRISM®, EIA (bead), and Quantum™ II (all from Abbott Laboratories), as well as other platforms known in the art. Additionally, the assays, kits and kit components can be employed in other formats, for example, on electrochemical and/or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Construction of Anti-DLL4/Anti-VEGF DVD Molecules

The variable domain sequences from a humanized anti-DLL4 mAb (h1A11.1) and anti-VEGF mAb (Av) were used to design the VH and VL domains of anti-DLL4/anti-VEGF DVD molecules. Variable regions were synthesized using two-step PCR. Primers were designed with homologous flanking regions to the cloning vector and the linker region between each DVD variable pair. Bacterial transformation was performed to identify positive clones and constructs were harvested and purified for use in mammalian transformation using standard protocols known in the art.

The variable domains of the heavy and light chain were cloned in-frame into mutant human IgG1 (L234, 235A) heavy-chain and kappa light-chain constant regions, respectively, to generate anti-DLL4/anti-VEGF DVD molecules (Table 4).

TABLE 4

| Anti-DLL4/Anti-VEGF DVD Constructs | | |
|---|---|---|
| DVD Name | Heavy Chain (HC) | Light Chain (LC) |
| h1A11.1-LL-Av | h1A11.1-L-Av HC | h1A11.1-L-Av LC |
| h1A11.1-LS-Av | h1A11.1-L-Av HC | h1A11.1-S-Av LC |
| h1A11.1-SL-Av | h1A11.1-S-Av HC | h1A11.1-L-Av LC |
| h1A11.1-SS-Av | h1A11.1-S-Av HC | h1A11.1-S-Av LC |
| h1A11.1-GS10-Av | h1A11.1-GS10-Av HC | h1A11.1-GS10-Av LC |
| h1A11.1-GS14-Av | h1A11.1-GS14-Av HC | h1A11.1-GS14-Av LC |
| Av-LL-h1A11.1 | Av-L-h1A11.1 HC | Av-L-h1A11.1 LC |
| Av-LS-h1A11.1 | Av-L-h1A11.1 HC | Av-S-h1A11.1 LC |
| Av-SL-h1A11.1 | Av-S-h1A11.1 HC | Av-L-h1A11.1 LC |
| Av-SS-h1A11.1 | Av-S-h1A11.1 HC | Av-S-h1A11.1 LC |
| Av-GS6-h1A11.1 | Av-GS6-h1A11.1 HC | Av-GS6-h1A11.1 LC |
| Av-GS10-h1A11.1 | Av-GS10-h1A11.1 HC | Av-GS10-h1A11.1 LC |
| Av-GS14-h1A11.1 | Av-GS14-h1A11.1 HC | Av-GS14-h1A11.1 LC |

Example 2

Affinity Determination of Anti-DLL4/Anti-VEGF DVD Constructs

A BIACORE assay (Biacore, Inc, Piscataway, N.J.) was used to evaluate the binding of DVDs to a purified recombinant DLL4 extracellular domain (ECD) or to $VEGF_{165}$, as determined by surface plasmon resonance-based measurements made on a Biacore 2000, Biacore 3000 or Biacore T100 (GE Healthcare, Piscataway, N.J.) at 25° C. For DLL4 binding kinetic measurements the assay buffer was HBS-EPB: 10 mM Hepes, pH7.5, 150 mM NaCl, 3 mM EDTA, 0.005% Tween 20, 0.1 mg/ml BSA (Sigma A7906). For VEGF binding kinetic measurements the assay buffer was HBS-EP+ (3N01B): 10 mM Hepes, pH7.5, 300 mM NaCl, 3 mM EDTA, 0.05% Tween 20, 0.1 mg/ml BSA (Sigma A7906). For example, approximately 9000 RU of goat anti-human Fc specific polyclonal antibody (Thermo Fisher Scientific Inc., Rockford, Ill.) diluted in 10 mM sodium acetate (pH 4.5) is directly immobilized across a CM5 research grade biosensor chip using a standard amine coupling kit according to manufacturer's instructions and procedures at 25 ug/ml. Unreacted moieties on the biosensor surface are blocked with ethanolamine. For kinetic analysis, rate equations derived from the 1:1 Langmuir binding model are fitted simultaneously to multiple antigen injections (using global fit analysis) with the use of Scrubber 2 (BioLogic Software), Biacore Biaevaluation 4.0.1 software or Biacore T100 Evaluation software. Purified antibodies are diluted in running buffer for capture across goat anti-human Fc reaction surfaces. Antibodies to be captured as a ligand (1 ug/ml) are injected over reaction matrices at a flow rate of 10 ul/min. During the assay, all measurements are referenced against the capture surface alone (i.e. with no captured antibody). The association and dissociation rate constants, $K_{on}$ ($M^{-1}s^{-1}$) and $K_{off}$ ($s^{-1}$) are determined under a continuous flow rate of 80 ul/min. Rate constants are derived by making kinetic binding measurements at different antigen concentrations ranging from 1.23-900 nM, as a 3-fold dilution series, and included buffer-only injections (to be used for double referencing). The equilibrium dissociation constant $K_D$ (M) of the reaction between antibodies and the target antigen is then calculated from the kinetic rate constants by the following formula: $K_D = K_{off}/K_{on}$. Binding is recorded as a function of time and kinetic rate constants are calculated. In this assay, on-rates as fast as $10^6$ $M^{-1}s^{-1}$ and off-rates as slow as $10^{-6}$ $s^{-1}$ can be measured. The antigen binding affinities of the anti-DLL4/anti-VEGF DVDs are summarized in Table 5 and 6.

TABLE 5

Biacore Kinetics of Anti-DLL4/Anti-VEGF DVD Binding Proteins

| DVD Name | BIAcore human $DLL4_{529}$ | | | BIAcore human $VEGF_{165}$ | | |
|---|---|---|---|---|---|---|
| | Kon ($M^{-1}s^{-1}$) | Koff ($s^{-1}$) | $K_D$ (M) | Kon ($M^{-1}s^{-1}$) | Koff ($s^{-1}$) | $K_D$ (M) |
| Av | N/A | N/A | N/A | 1.19E+05 | 3.47E−05 | 2.9E−10 |
| h1A11.1 | 1.60E+05 | 1.93E−03 | 1.2E−08 | N/A | N/A | N/A |
| h1A11.1-LL-Av | 2.05E+05 | 2.63E−03 | 1.2E−08 | 5.19E+04 | 2.44E−05 | 4.7E−10 |
| h1A11.1-LS-Av | 2.15E+05 | 2.36E−03 | 1.1E−08 | 2.26E+04 | 2.83E−05 | 1.3E−09 |
| h1A11.1-SL-Av | 2.17E+05 | 2.24E−03 | 1.0E−08 | 4.57E+04 | 3.20E−05 | 7.0E−10 |
| h1A11.1-SS-Av | 1.92E+05 | 2.25E−03 | 1.2E−08 | 7.32E+03 | 5.42E−05 | 7.4E−09 |
| h1A11.GS10-Av | 2.52E+05 | 2.33E−03 | 9.3E−09 | 1.92E+04 | 4.26E−05 | 2.2E−09 |
| h1A11.1-GS14-Av | 2.40E+05 | 2.33E−03 | 9.7E−09 | 2.87E+04 | 3.72E−05 | 1.3E−09 |
| Av-GS6-h1A11.1 | 1.41E+04 | 7.03E−04 | 5.0E−08 | 1.94E+05 | 3.72E−05 | 1.9E−10 |
| Av-GS10-h1A11.1 | 3.45E+04 | 1.01E−03 | 2.9E−08 | 1.84E+05 | 3.59E−05 | 1.9E−10 |
| Av-GS14-h1A11.1 | 3.97E+04 | 1.34E−03 | 3.4E−08 | 1.82E+05 | 3.08E−05 | 1.7E−10 |

N/A: not applicable

TABLE 6

Additional Biacore Kinetics of h1A11.1-SL-Av DVD

| DVD Name | BIAcore cynomolgus monkey $DLL4_{529}$ | | | BIAcore mouse $DLL4_{530}$ | | |
|---|---|---|---|---|---|---|
| | Kon ($M^{-1}s^{-1}$) | Koff ($s^{-1}$) | $K_D$ (M) | Kon ($M^{-1}s^{-1}$) | Koff ($s^{-1}$) | $K_D$ (M) |
| h1A11.1-SL-Av | 4.43E+05 | 2.49E−03 | 5.6E−09 | 3.22E+05 | 7.74E−03 | 2.4E−08 |

Example 3

In Vitro Characterization of the Anti-DLL4/Anti-VEGF DVD Molecules

Example 3.1

DLL4 Binding Activity as Determined by Flow Cytometry (FACS)

Stable HEK293G cell lines overexpressing full-length DLL4 were harvested from tissue culture flasks, washed four times and resuspended in phosphate buffered saline (PBS) containing 1% bovine serum albumin and 1 mM $CaCl_2$ (FACS buffer). $1.5 \times 10^5$ cells were incubated with DVD binding proteins at various concentrations in FACS buffer for 60 minutes on ice. Cells were washed twice and 50 uL of R-phycoerythrin-conjugated anti-rat IgG F(ab')$_2$ fragment (1:200 dilution in FACS buffer) (Jackson ImmunoResearch, West Grove, Pa., Cat. #112-116-072) was added. Following an incubation on ice (4° C., 60 minutes), cells were washed three times and resuspended in FACS buffer. Fluorescence was measured using a Becton Dickinson FACSCalibur-HTS (Becton Dickinson, San Jose, Calif.). Data was analyzed using Graphpad Prism software and $EC_{50}$ values were reported as the concentration of antibody to achieve 50% of maximal antibodies binding to DLL4 expressing cells.

Example 3.2

DLL4-Blocking Activity of the Anti-DLL4/Anti-VEGF DVD Proteins as Determined by Inhibition of Notch-1 Interaction with Soluble DLL4 Extracellular Domain 96-well Nunc-Immuno plates (#439454 for huDLL4 ELISA) and 96-well Costar plates (#9018 for muDLL4 ELISA) were coated with 16 nM human Notch-1 (R&D Systems #3647-TK, 100 µl/well in D-PBS) and incubated overnight at 4° C. Plates were then washed 3× with wash buffer (PBS, 0.05% Tween-20) and blocked with 200 µl/well blocking buffer (D-PBS, 1% BSA, 1 mM $CaCl_2$, 0.05% Tween-20) for 1 hour at 25° C. While blocking, biotin labeled DLL4 extracellular domain (14 nM) was mixed with antibody (30 pM-66 nM, 3-fold serial dilution in blocking buffer) for 1 hour at 25° C. with shaking. Assay plates were washed after blocking, and incubated with DLL4/antibody mixtures (100 µl/well, 1 hour at 25° C. with shaking). Plates were washed again and 100 µl/well of streptavidin conjugated with HRP (Fitzgerald #65R-S104PHRPx, diluted 1:5,000 in blocking buffer) was added for 1 hour at 25° C. with shaking. After a final wash, plates were developed using 100 µl/well substrate (TMB Sigma #T8665), and the reaction was stopped using 100 µl/well 1N HCl, and the absorbance was read at 450 nm. Data was analyzed using Graphpad Prism software and $IC_{50}$ values were reported as the concentration of antibody required to achieve 50% reduction of DLL4 binding to Notch1.

Example 3.3

DLL4-Blocking Activity of the Anti-DLL4/Anti-VEGF DVD Proteins as Determined by Inhibition of DLL4-Dependent Notch Activation Using a Notch Reporter Assay 96-well black clear-bottom tissue culture plates were seeded overnight with engineered EA.hy926 cells expressing luciferase driven by a Notch-responsive promoter (7,000 cells/well). Antibodies serially diluted from 200 nM were mixed for 15 minutes with an equal volume of solution containing HEK293G cells expressing full-length DLL4 (5,000 cells/well). The 293G/DLL4 cells were co-cultured with EA.hy926 Notch reporter cells for 24 hrs in the presence of testing antibodies. Luciferase activity was analyzed using Promega's substrate (Promega # E2940). Data was analyzed using Graphpad Prism software and $IC_{50}$ values were reported as the concentration of antibody required to achieve a 50% reduction of DLL4-induced Notch activation.

Example 3.4

VEGF Binding Activity of Anti-DLL4/Anti-VEGF DVD Proteins as Determined by Capture ELISA ELISA plates (Nunc, MaxiSorp, Rochester, N.Y.) were incubated overnight at 4° C. with anti-human Fc antibody (5 µg/ml in PBS, Jackson Immunoresearch, West Grove, Pa.). Plates were washed three times in wash buffer (PBS containing 0.05% Tween 20), and blocked for 1 hour at 25° C. in blocking buffer (PBS containing 1% BSA). Wells were washed three times, and each antibody or DVD was serially diluted in PBS containing 0.1% BSA before incubating at 25° C. for 1 hour. The wells were washed three times, and biotinylated VEGF (2 nM) was added to the plates and incubated for 1 hour at 25° C. The wells were washed three times, and then incubated for 1 hour at 25° C. with streptavidin-HRP (KPL #474-3000, Gaithersburg, Md.). The wells were washed three times, and 100 µl of ULTRA-TMB ELISA (Pierce, Rockford, Ill.) was added per well. Following color development, the reaction was stopped with 1M HCl and absorbance at 450 nM was measured.

Example 3.5

VEGF-Blocking Activity of Anti-DLL4/Anti-VEGF DVD Proteins as Determined by Inhibition of VEGF Interaction with VEGFR1

ELISA plates (Nunc, MaxiSorp, Rochester, N.Y.) were incubated overnight at 4° C. with 100 µl of PBS containing recombinant VEGFR1 extra-cellular domain-Fc fusion protein (5 µg/ml, R&D systems, Minneapolis, Minn.). Plates were washed three times in washing buffer (PBS containing 0.05% Tween 20), and blocked for 1 hour at 25° C. in blocking buffer (PBS containing 1% BSA). Each antibody and DVD was serially diluted in PBS containing 0.1% BSA and incubated with 50 µl of 2 nM biotinylated VEGF for 1 hour at 25° C. The mixtures of antibody and biotinylated VEGF or DVD and biotinylated VEGF (100 µl) were then added to the VEGFR1-Fc coated wells and incubated at 25° C. for 10 minutes. The wells were washed three times, and then incubated for 1 hour at 25° C. with 100 µl of streptavidin-HRP (KPL #474-3000, Gaithersburg, Md.). The wells were washed three times, and 100 µl of ULTRA-TMB ELISA (Pierce, Rockford, Ill.) was added per well. Following color development, the reaction was stopped with 1M HCl and absorbance at 450 nM was measured.

Example 3.6

VEGF-Blocking Activity of Anti-DLL4/Anti-VEGF DVD Protein as Determined by Inhibition of VEGF-Stimulated Endothelial Cell Proliferation/Survival Prior to plating for the assay, TIME (ATCC) or HUVEC (passage 2-6) endothelial cells were maintained in EBM-2

(Lonza-Clonetics, Walkersville, Md.) supplemented with EGM-2 SingleQuots (Lonza-Clonetics, Walkersville, Md., #CC-4176). Cells were plated at 10,000 cells/well on collagen-coated black 96-well plates in 100 µl EMB-2 with 0.1% FBS in the absence of growth factors. The following day the media was replaced with 0.1% FBS in the absence of growth factors. The following day the media was replaced with 100 µl of EMB-2 (without growth factors or serum) and incubated for four hours prior to the addition of VEGF and antibodies or DVDs. Anti-VEGF monoclonal antibodies or DVDs were serially diluted in EMB-2 with 0.1% BSA and were pre-incubated with recombinant human $VEGF_{165}$ (50 ng/ml) for 1 hour at 25° C. in 50 µl. Mixtures of antibody and VEGF or DVD and VEGF were then added to the cells (50 µl), and the plates were incubated at 37° C. in a humidified, 5% $CO_2$ atmosphere for 72 hours. Cell survival/proliferation was measured indirectly by assessing ATP levels using an ATPlite kit (Perkin Elmer, Waltham, Mass.) according to the manufacturer's instructions.

The in vitro activities of the anti-DLL4/anti-VEGF DVDs, as characterized by the above-mentioned assays, are summarized in Table 7.

TABLE 7

In Vitro Characterization of Anti-DLL4/Anti-VEGF DVDs

| | Human DLL4 | | | Human VEGF | | |
|---|---|---|---|---|---|---|
| | | Functional Blockade | | | Functional Blockade | |
| DVD Name | Binding FACS $EC_{50}$ (nM) | Notch Competition ELISA $IC_{50}$ (nM) | Notch Activation $IC_{50}$ (nM) | Binding ELISA $EC_{50}$ (nM) | VEGFR1 Competition ELISA $IC_{50}$ (nM) | Endothelial Cell Proliferation $IC_{50}$ (nM) |
| Av-LL-h1A11.1 | | 2.43 | | | | |
| Av-LS-h1A11.1 | | 2.77 | | | | |
| Av-SL-h1A11.1 | | 7.38 | | | | |
| Av-SS-h1A11.1 | | 3503 | | | | |
| h1A11.1-LL-Av | 5.04 | 0.79 | 4.56 | 0.12 | 3.8 | 0.42 |
| h1A11.1-LS-Av | 5 | 0.76 | 4.59 | 0.16 | 7.7 | 0.57 |
| h1A11.1-SL-Av | 4.35 | 1.09 | 5.34 | 0.55 | 3.8 | 0.61 |
| h1A11.1-SS-Av | 3.75 | 0.91 | 7.47 | 2.5 | 26 | 4.2 |
| h1A11.1-GS10-Av | | 0.65 | | 0.99 | 37.2 | 1.21 |
| h1A11.1-GS14-Av | | 0.68 | | 0.41 | 20.2 | 0.84 |
| Av-GS6-h1A11.1 | | 3.41 | | 0.25 | 7.44 | 4.14 |
| Av-GS10-h1A11.1 | | 1.5 | | 0.12 | 2.01 | 0.57 |
| Av-GS14-h1A11.1 | | 1.54 | | 0.17 | 4.69 | 0.48 |

Example 4

In Vivo Pharmacokinetic Results of Anti-DLL4/Anti-VEGF DVD

The pharmacokinetics properties of h1A11.1-SL-Av DVD were assessed in cynomolgus monkeys (n=2 for each dose group) and CD1 mice (n=6 for each dose group) following bolus intravenous administration. The h1A11.1-SL-Av DVD pharmacokinetic profile in both CD1 mice and cynomolgus monkeys was characteristic of a traditional monoclonal antibody (Table 8).

TABLE 8

Mean PK Parameters of h1A11.1-SL-Av DVD after Bolus Intravenous Administration

| Species | Dose | AUC | Cmax | Vss | CL | T½ | MRT |
|---|---|---|---|---|---|---|---|
| Mouse | 1 | 30.4 | 16.6 | 56.6 | 33.6 | 1.4 | 1.8 |
| | 3 | 203.1 | 68.9 | 46.2 | 14.9 | 2.3 | 3.1 |
| | 10 | 570.3 | 187.2 | 102.8 | 18.3 | 4.7 | 5.9 |
| | 30 | 4488.1 | 496.2 | 94.4 | 6.8 | 9.8 | 13.7 |
| Monkey | 1 | 109.7 | 30.3 | 35.9 | 10.5 | 3.1 | 3.9 |
| | 3 | 403.9 | 92.8 | 33.9 | 7.5 | 4.3 | 4.6 |
| | 10 | 1957.1 | 395.1 | 35.9 | 5.1 | 5.0 | 7.1 |
| | 30 | 8626.9 | 1344.4 | 27.0 | 3.7 | 5.5 | 7.8 |

Dose: mg/kg;
AUC: Area under the concentration curve from 0 to time infinity (d*ug/mL);
Cmax: First observed conc. post dosing (ug/mL);
Vss: volume of distribution (mL/kg);
CL: clearance (mL/day/kg);
T½: terminal half-life (days);
MRT: Mean residence time from 0 to infinity (days).

Example 5

In Vivo Anti-Tumor Efficacy of Anti-DLL4/Anti-VEGF DVDs

The effect of anti-DLL4/anti-VEGF DVDs on tumor growth was initially evaluated on HT-29 human colorectal adenocarcinoma xenograft tumors in female athymic nude mice. Briefly, $2 \times 10^6$ cells were inoculated subcutaneously into the right hind flank. Tumors were allowed to establish for 25 days, at which point tumor volume was determined using electronic caliper measurements using the formula: $L \times W^2/2$. Mice were allocated into treatment groups (n=10 per group) so that each cohort had equivalent mean tumor volume of 214 $mm^3$ prior to initiation of therapy. Animals were dosed intraperitoneally weekly for four weeks, with tumor volume measured twice a week for the duration of the experiment. Results are shown in Table 9.

The effect of anti-DLL4/anti-VEGF DVDs on tumor growth was subsequently evaluated on U87-MG human glioblastoma xenograft tumors in female SCID mice. Briefly, $3\times10^6$ cells were inoculated subcutaneously into the right hind flank. Tumors were allowed to establish for 17 days, at which point tumor volume was determined using electronic caliper measurements using the formula: $L\times W^2/2$. Mice were allocated into treatment groups (n=10 per group) so that each cohort had equivalent mean tumor volume of 221 mm$^3$ prior to initiation of therapy. Animals were dosed intraperitoneally weekly for four weeks, with tumor volume measured twice a week for the duration of the experiment. Results are shown in Table 9.

TABLE 9

Efficacy of Anti-DLL4/Anti-VEGF DVDs in the HT-29 Colorectal Adenocarcinoma and U87-MG Glioblastoma Xenograft Models

| Treatment | Dose Route, Regimen | HT-29 % TGI[a] | HT-29 % TGD[b] | 87-MG % TGI[c] | 87-MG % TGD[b] |
|---|---|---|---|---|---|
| h1A11.1-LL-Av | 6.7 mg/kg IP, q7dX4 | 59** | 42*** | 74*** | 100*** |
| h1A11.1-LS-Av | 6.7 mg/kg IP, q7dX4 | 59** | 42*** | 77*** | 124*** |
| h1A11.1-SL-Av | 6.7 mg/kg IP, q7dX4 | 68*** | 61*** | 81*** | 100*** |
| h1A11.1-SS-Av | 6.7 mg/kg IP, q7dX4 | 47* | 49* | 64*** | 48*** |

[a]% TGI = Percent tumor growth inhibition = 100 − (T/C × 100), where T = mean tumor volume of treatment group and C = mean tumor volume of treatment control group. Based on day 29 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$. P values (as indicated by asterisks) derived from Kaplan Meier log-rank comparison of treatment group vs. treatment control group.
[c]% TGI = Percent tumor growth inhibition = 100 − (T/C × 100), where T = mean tumor volume of treatment group and C = mean tumor volume of treatment control group. Based on day 24 post size match measurements.
P values (as indicated by asterisks) are derived from Student's T test comparison of treatment group vs. treatment control group (*p <0.01, p < 0.001, *p < 0.0001)

Example 6

In Vivo Combination Efficacy of Anti-DLL4/Anti-VEGF DVDs

The effect of anti-DLL4/anti-VEGF DVDs in combination with chemotherapy on tumor growth was evaluated on U87-MG human glioblastoma xenograft tumors in female SCID mice. Briefly, $3\times10^6$ cells were inoculated subcutaneously into the right hind flank. Tumors were allowed to establish for 22 days, at which point tumor volume was determined using electronic caliper measurements using the formula: $L\times W^2/2$. Mice were allocated into treatment groups (n=10 per group) so that each cohort had equivalent mean tumor volume of 207 mm$^3$ prior to initiation of therapy. Animals were dosed intraperitoneally with a single dose of Temozolomide® and/or four weekly doses of anti-DLL4/anti-VEGF DVD, with tumor volume measured twice a week for the duration of the experiment. Results are shown in Table 10.

TABLE 10

Combination Efficacy of Anti-DLL4/Anti-VEGF DVD and Temozolomide in the U87-MG Glioblastoma Xenograft Model

| Treatment | Dose Route, Regimen | % TGI[a] | % TGD[b] |
|---|---|---|---|
| Temozolomide | 5 mg/kg IP, qdX1 | 65*** | 45*** |
| h1A11.1-SL-Av | 6.7 mg/kg IP, q7dX4 | 69*** | 100*** |
| Temozolomide + h1A11.1-SL-Av | 5 mg/kg IP, qdX1 + 6.7 mg/kg IP, q7dX4 | 78*** | 147*** |

[a]% TGI = Percent tumor growth inhibition = 100 − (T/C × 100), where T = mean tumor volume of treatment group and C = mean tumor volume of treatment control group. Based on day 19 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group (*p < 0.01, p < 0.001, *p < 0.0001).

Example 7

Preformulation Characterization of Anti-DLL4/Anti-VEGF DVDs

The storage stability (5° C.) and accelerated stability (40° C.) of an anti-DLL4/anti-VEGF DVD (h1A11.1-SL-Av) was evaluated in the formulations and protein concentrations listed below. Stability was evaluated by size exclusion chromatography (SE-HPLC) and % aggregate, % monomer, % fragment, and total species recovered were quantitated. Overall, the formulations cover a pH range of 5 to 7 and a protein concentration range of 1.0 to 118 mg/ml.

At 5° C. and 40° C. temperatures and at protein concentrations of 50, 30, and 10 mg/ml, formulations were: 15 mM acetate pH 5; 15 mM phosphate pH 7; 30 mM acetate, 80 mg/ml sucrose, 0.02% Tween 80 at pH 5; 30 mM histidine, 80 mg/ml sucrose, 0.02% Tween 80 at pH 6; PBS (phosphate buffered saline). All formulations contained 0.02% sodium azide to prevent microbial growth during storage. At 5° C. and 40° C. temperatures and at protein concentrations of 60, 50, 30, and 10 mg/ml, the formulation was 15 mM histidine pH 6 (also containing 0.02% sodium azide to prevent microbial growth during storage). At 5° C. and at a protein concentration of 118 mg/ml, the formulation was 15 mM histidine pH 6 (also containing 0.02% sodium azide to prevent microbial growth during storage). At 40° C. and at a protein concentration of 1.0 mg/ml, the formulations were 10 mM citrate+10 mM phosphate at pHs 5, 6, 7. Formulations with protein were filtered to remove possible microbes.

Freeze-thaw stability was performed by subjecting the protein in formulation to four cycles of freezing at −80° C. for at least 20 hours and thawing in a 30° C. water bath. The formulations that were tested for freeze-thaw stability are listed below. Stability was evaluated by SE-HPLC and % aggregate, % monomer, % fragment, and total species recovered were quantitated. The formulations were 15 mM histidine pH 6 at 60 mg/ml protein (also containing 0.02% sodium azide to prevent microbial growth) and 10 mM citrate+10 mM phosphate at pHs 5, 6, 7 and 1.0 mg/ml protein (filtered to remove possible microbes).

Finally, differential scanning calorimetry to measure thermal stability was performed on the protein in 10 mM citrate+10 mM phosphate buffer at pHs 5, 6, 7 and 1.0 mg/ml protein. The onset temperature of unfolding and the midpoint temperatures of unfolding (Tm) of each protein domain were quantitated.

TABLE 11

Accelerated stability at 40° C. of h1A11.1-SL-Av at different concentrations and in different buffers, excipients, and pHs

| Protein conc (mg/ml) | time | temp (° C.) | buffer | pH | % Aggregate | % Monomer | % Fragment | Total Area |
|---|---|---|---|---|---|---|---|---|
| — | pre-dialysis | — | — | — | 2.71 | 96.31 | 0.98 | 53058 |
| 50, 30, 10 | T0 | — | ace | 5 | 2.89 | 96.08 | 1.03 | 48033 |
| 50, 30, 10 | T0 | — | his | 6 | 2.81 | 96.23 | 0.96 | 46995 |
| 50, 30, 10 | T0 | — | phos | 7 | 2.91 | 96.09 | 1.00 | 52571 |
| 50, 30, 10 | T0 | — | ace-suc-tw | 5 | 2.54 | 96.50 | 0.96 | 50185 |
| 50, 30, 10 | T0 | — | his-suc-tw | 6 | 2.37 | 96.62 | 1.01 | 50771 |
| 50, 30, 10 | T0 | — | PBS | 7 | 2.90 | 96.08 | 1.01 | 49170 |
| 50 | T7 d | 40 | ace | 5 | 5.19 | 93.32 | 1.49 | 49028 |
| 30 | T7 d | 40 | ace | 5 | 3.86 | 94.68 | 1.47 | 48171 |
| 10 | T7 d | 40 | ace | 5 | 2.60 | 95.97 | 1.43 | 48379 |
| 50 | T7 d | 40 | his | 6 | 5.25 | 93.46 | 1.29 | 47731 |
| 30 | T7 d | 40 | his | 6 | 4.13 | 94.58 | 1.29 | 46684 |
| 10 | T7 d | 40 | his | 6 | 2.73 | 95.84 | 1.42 | 46877 |
| 50 | T7 d | 40 | phos | 7 | 9.02 | 89.52 | 1.46 | 53429 |
| 30 | T7 d | 40 | phos | 7 | 6.11 | 92.40 | 1.49 | 51923 |
| 10 | T7 d | 40 | phos | 7 | 3.94 | 94.57 | 1.49 | 53098 |
| 50 | T7 d | 40 | ace-suc-tw | 5 | 5.42 | 92.85 | 1.73 | 50373 |
| 30 | T7 d | 40 | ace-suc-tw | 5 | 4.07 | 94.06 | 1.87 | 48768 |
| 10 | T7 d | 40 | ace-suc-tw | 5 | 2.66 | 95.20 | 2.14 | 49396 |
| 50 | T7 d | 40 | his-suc-tw | 6 | 3.44 | 95.02 | 1.54 | 50040 |
| 30 | T7 d | 40 | his-suc-tw | 6 | 4.16 | 94.14 | 1.70 | 48715 |
| 10 | T7 d | 40 | his-suc-tw | 6 | 2.86 | 95.24 | 1.90 | 49871 |
| 50 | T7 d | 40 | PBS | 7 | 8.13 | 90.28 | 1.60 | 49207 |
| 30 | T7 d | 40 | PBS | 7 | 5.82 | 92.55 | 1.63 | 48853 |
| 10 | T7 d | 40 | PBS | 7 | 3.62 | 94.82 | 1.56 | 48166 |
| 50 | T21 d | 40 | ace | 5 | 6.65 | 90.83 | 2.51 | 48536 |
| 30 | T21 d | 40 | ace | 5 | 4.55 | 92.91 | 2.54 | 48520 |
| 10 | T21 d | 40 | ace | 5 | 2.71 | 94.70 | 2.59 | 48395 |
| 50 | T21 d | 40 | his | 6 | 7.01 | 90.71 | 2.27 | 46729 |
| 30 | T21 d | 40 | his | 6 | 4.69 | 93.10 | 2.21 | 46687 |
| 10 | T21 d | 40 | his | 6 | 2.77 | 94.93 | 2.30 | 46866 |
| 50 | T21 d | 40 | phos | 7 | 13.39 | 83.83 | 2.78 | 52244 |
| 30 | T21 d | 40 | phos | 7 | 9.38 | 87.76 | 2.86 | 53556 |
| 10 | T21 d | 40 | phos | 7 | 4.77 | 92.32 | 2.91 | 52536 |
| 50 | T21 d | 40 | ace-suc-tw | 5 | 6.37 | 90.34 | 3.30 | 48268 |
| 30 | T21 d | 40 | ace-suc-tw | 5 | 4.27 | 91.91 | 3.82 | 47211 |
| 10 | T21 d | 40 | ace-suc-tw | 5 | 2.26 | 93.02 | 4.72 | 46322 |
| 50 | T21 d | 40 | his-suc-tw | 6 | 6.84 | 89.82 | 3.34 | 47140 |
| 30 | T21 d | 40 | his-suc-tw | 6 | 4.60 | 91.90 | 3.50 | 47416 |
| 10 | T21 d | 40 | his-suc-tw | 6 | 2.67 | 93.66 | 3.67 | 48166 |
| 50 | T21 d | 40 | PBS | 7 | 12.13 | 84.81 | 3.06 | 49845 |
| 30 | T21 d | 40 | PBS | 7 | 8.09 | 88.78 | 3.13 | 48108 |
| 10 | T21 d | 40 | PBS | 7 | 4.20 | 92.63 | 3.17 | 48803 |

Buffer Key (all buffers contain 0.02% sodium azide to prevent microbial growth):
ace = 15 mM acetate pH5;
his = 15 mM histidine pH 6;
phos = 15 mM phosphate pH 7
ace-suc-tw = 30 mM acetate, 80 mg/ml sucrose, 0.02% Tw80
his-suc-tw = 30 mM histidine, 80 mg/ml sucrose, 0.02% Tw80
PBS = phosphate buffered saline

TABLE 12

Storage stability at 5° C. of h1A11.1-SL-Av at different concentrations and in different buffers, excipients, and pHs (buffer key same as in Table 11)

| Protein conc (mg/ml) | time | temp (° C.) | buffer | pH | % Aggregate | % Monomer | % Fragment | Total Area |
|---|---|---|---|---|---|---|---|---|
| — | pre-dialysis | — | — | — | 2.71 | 96.31 | 0.98 | 53058 |
| 50, 30, 10 | T0 | — | ace | 5 | 2.89 | 96.08 | 1.03 | 48033 |
| 50, 30, 10 | T0 | — | his | 6 | 2.81 | 96.23 | 0.96 | 46995 |
| 50, 30, 10 | T0 | — | phos | 7 | 2.91 | 96.09 | 1.00 | 52571 |
| 50, 30, 10 | T0 | — | ace-suc-tw | 5 | 2.54 | 96.50 | 0.96 | 50185 |
| 50, 30, 10 | T0 | — | his-suc-tw | 6 | 2.37 | 96.62 | 1.01 | 50771 |

TABLE 12-continued

Storage stability at 5° C. of h1A11.1-SL-Av at different concentrations and in different buffers, excipients, and pHs (buffer key same as in Table 11)

| Protein conc (mg/ml) | time | temp (° C.) | buffer | pH | % Aggregrate | % Monomer | % Fragment | Total Area |
|---|---|---|---|---|---|---|---|---|
| 50, 30, 10 | T0 | — | PBS | 7 | 2.90 | 96.08 | 1.01 | 49170 |
| 50 | T7 d | 5 | ace | 5 | 2.96 | 95.99 | 1.05 | 49118 |
| 30 | T7 d | 5 | ace | 5 | 2.74 | 96.21 | 1.06 | 48434 |
| 10 | T7 d | 5 | ace | 5 | 2.62 | 96.23 | 1.15 | 48915 |
| 50 | T7 d | 5 | his | 6 | 2.93 | 95.87 | 1.20 | 47967 |
| 30 | T7 d | 5 | his | 6 | 2.75 | 96.06 | 1.19 | 47182 |
| 10 | T7 d | 5 | his | 6 | 2.55 | 96.31 | 1.13 | 47395 |
| 50 | T7 d | 5 | phos | 7 | 3.15 | 95.64 | 1.21 | 53843 |
| 30 | T7 d | 5 | phos | 7 | 3.10 | 95.76 | 1.14 | 53372 |
| 10 | T7 d | 5 | phos | 7 | 2.91 | 95.96 | 1.13 | 53269 |
| 50 | T7 d | 5 | ace-suc-tw | 5 | 2.75 | 96.13 | 1.12 | 50236 |
| 30 | T7 d | 5 | ace-suc-tw | 5 | 2.62 | 96.11 | 1.27 | 50026 |
| 10 | T7 d | 5 | ace-suc-tw | 5 | 2.56 | 96.18 | 1.26 | 49290 |
| 50 | T7 d | 5 | his-suc-tw | 6 | 2.84 | 96.10 | 1.07 | 50129 |
| 30 | T7 d | 5 | his-suc-tw | 6 | 2.58 | 96.19 | 1.23 | 49272 |
| 10 | T7 d | 5 | his-suc-tw | 6 | 2.64 | 96.08 | 1.28 | 50926 |
| 50 | T7 d | 5 | PBS | 7 | 3.26 | 95.59 | 1.15 | 49502 |
| 30 | T7 d | 5 | PBS | 7 | 3.07 | 95.64 | 1.29 | 49724 |
| 10 | T7 d | 5 | PBS | 7 | 2.83 | 95.87 | 1.29 | 49563 |
| 50 | T21 d | 5 | ace | 5 | 2.57 | 95.76 | 1.67 | 49722 |
| 30 | T21 d | 5 | ace | 5 | 2.37 | 96.03 | 1.60 | 48882 |
| 10 | T21 d | 5 | ace | 5 | 2.22 | 96.09 | 1.69 | 49255 |
| 50 | T21 d | 5 | his | 6 | 2.63 | 95.63 | 1.74 | 44884 |
| 30 | T21 d | 5 | his | 6 | 2.42 | 95.95 | 1.62 | 47510 |
| 10 | T21 d | 5 | his | 6 | 2.19 | 96.08 | 1.73 | 47015 |
| 50 | T21 d | 5 | phos | 7 | 3.06 | 94.96 | 1.98 | 53449 |
| 30 | T21 d | 5 | phos | 7 | 2.69 | 95.46 | 1.85 | 52938 |
| 10 | T21 d | 5 | phos | 7 | 2.35 | 95.84 | 1.81 | 52703 |
| 50 | T21 d | 5 | ace-suc-tw | 5 | 2.25 | 95.76 | 1.99 | 50960 |
| 30 | T21 d | 5 | ace-suc-tw | 5 | 2.08 | 95.90 | 2.02 | 49042 |
| 10 | T21 d | 5 | ace-suc-tw | 5 | 1.97 | 95.84 | 2.19 | 49851 |
| 50 | T21 d | 5 | his-suc-tw | 6 | 2.24 | 95.62 | 2.14 | 49983 |
| 30 | T21 d | 5 | his-suc-tw | 6 | 2.09 | 95.86 | 2.05 | 48813 |
| 10 | T21 d | 5 | his-suc-tw | 6 | 1.97 | 95.83 | 2.19 | 49984 |
| 50 | T21 d | 5 | PBS | 7 | 2.84 | 95.07 | 2.09 | 50641 |
| 30 | T21 d | 5 | PBS | 7 | 2.27 | 95.62 | 2.12 | 48441 |
| 10 | T21 d | 5 | PBS | 7 | 1.99 | 95.94 | 2.07 | 48978 |
| 50 | T10 mo | 5 | his | 6 | 8.05 | 91.04 | 0.91 | 45552 |
| 30 | T10 mo | 5 | his | 6 | 5.81 | 93.29 | 0.90 | 46607 |
| 10 | T10 mo | 5 | his | 6 | 3.62 | 95.46 | 0.92 | 46207 |
| 50 | T10 mo | 5 | his-suc-tw | 6 | 8.08 | 90.26 | 1.67 | 45430 |
| 30 | T10 mo | 5 | his-suc-tw | 6 | 5.98 | 92.43 | 1.58 | 42967 |
| 10 | T10 mo | 5 | his-suc-tw | 6 | 3.95 | 94.25 | 1.80 | 42567 |

TABLE 13

Storage stability at 5° C., accelerated stability at 40° C., and freeze-thaw stability of h1A11.1-SL-Av at different concentrations and in different buffers and pHs

| Protein conc (mg/ml) | time/FT | temp (° C.) | buffer | pH | % Aggregrate | % Monomer | % Fragment | Total Area |
|---|---|---|---|---|---|---|---|---|
| 1 | T0 | — | cit-phos | 5 | 7.07 | 92.14 | 0.80 | 46824 |
| 1 | T8 d | 40 | cit-phos | 5 | 2.23 | 96.39 | 1.38 | 47090 |
| 1 | T22 d | 40 | cit-phos | 5 | 7.10 | 89.62 | 3.28 | 47956 |
| 1 | FT2 | — | cit-phos | 5 | 7.91 | 90.75 | 1.34 | 46502 |
| 1 | FT4 | — | cit-phos | 5 | 7.41 | 92.18 | 0.41 | 52181 |
| 1 | T0 | — | cit-phos | 6 | 7.17 | 92.33 | 0.50 | 45809 |
| 1 | T8 d | 40 | cit-phos | 6 | 2.56 | 96.03 | 1.42 | 46783 |
| 1 | T22 d | 40 | cit-phos | 6 | 5.79 | 91.73 | 2.48 | 47401 |
| 1 | FT2 | — | cit-phos | 6 | 7.14 | 91.48 | 1.38 | 45256 |
| 1 | FT4 | — | cit-phos | 6 | 7.09 | 92.56 | 0.34 | 45004 |
| 1 | T0 | — | cit-phos | 7 | 6.82 | 92.67 | 0.51 | 47025 |
| 1 | T8 d | 40 | cit-phos | 7 | 2.52 | 95.95 | 1.53 | 48080 |
| 1 | T22 d | 40 | cit-phos | 7 | 5.52 | 91.58 | 2.90 | 48706 |
| 1 | FT2 | — | cit-phos | 7 | 7.23 | 91.52 | 1.25 | 46732 |
| 1 | FT4 | — | cit-phos | 7 | 7.15 | 92.49 | 0.36 | 46561 |

TABLE 13-continued

Storage stability at 5° C., accelerated stability at 40° C., and freeze-thaw stability of h1A11.1-SL-Av at different concentrations and in different buffers and pHs

| Protein conc (mg/ml) | time/FT | temp (° C.) | buffer | pH | % Aggregrate | % Monomer | % Fragment | Total Area |
|---|---|---|---|---|---|---|---|---|
| 60 and 118 | T0 | — | his | 6 | 8.03 | 91.15 | 0.82 | 43528 |
| 60 | T7 d | 40 | his | 6 | 7.17 | 91.76 | 1.07 | 45333 |
| 60 | T21 d | 40 | his | 6 | 15.77 | 82.13 | 2.10 | 44729 |
| 60 | T7 d | 5 | his | 6 | 3.83 | 95.32 | 0.86 | 46774 |
| 60 | T26 d | 5 | his | 6 | 7.14 | 92.56 | 0.30 | 63982 |
| 118 | T5 mo | 5 | his | 6 | 12.82 | 86.65 | 0.53 | 55869 |
| 60 | T5 mo | 5 | his | 6 | 9.46 | 90.03 | 0.51 | 64573 |
| 60 | FT2 | — | his | 6 | 6.71 | 92.59 | 0.70 | 42259 |
| 60 | FT4 | — | his | 6 | 6.33 | 93.62 | 0.05 | 41054 |

Key:
FT = freeze thaw
FT2 = analysis after two cycles of freeze and thaw; freezing at −80° C. and thawing in a 30° C. water bath
FT4 = analysis after four cycles of freeze and thaw; freezing at −80° C. and thawing in a 30° C. water bath
cit-phos = 10 mM citrate + 10 mM phosphate
his = 15 mM histidine + 0.02% sodium azide (azide for preventing microbial growth)

TABLE 14

Differential scanning calorimetry data of h1A11.1-SL-Av at 1 mg/ml in 10 mM citrate + 10 mM phosphate at different pHs

| pH | Onset (° C.) | Tm1 (° C.) | Tm2 (° C.) | Tm3 (° C.) | Tm4 (° C.) |
|---|---|---|---|---|---|
| 5 | 55 | 68.2 | 68.86 | 75.56 | 81.18 |
| 6 | 58 | 69.04 | 70.47 | 75.24 | 82.04 |
| 7 | 59 | 69.52 | 70.94 | 74.44 | 82.06 |

Example 8

Formulation Selection for Anti-DLL4/Anti-VEGF DVDs

Materials and Methods.

The stability of anti-DLL4/anti-VEGF DVD h1A11.1-SL-Av protein was evaluated in the six formulations listed in Table 15. All formulations were prepared in 15 mM histidine buffer. Formulations F1 to F4 were prepared at 50 mg/mL protein concentration. In these formulations, the pH ranged from 5.5 to 6.0, polysorbate 80 concentration ranged from 0 to 0.05% w/v, sucrose concentration ranged from 0 to 7.5% w/v, and arginine concentration ranged from 0 to 1% w/v. Formulation F4 was prepared in 15 mM histidine buffer at pH 6.0 without any stabilizers and served as a study control for the 50 mg/mL liquid formulation stability assessment. In addition, two formulations were prepared at 25 mg/mL protein concentration at pH 6.0 (Formulations F5 and F6). The composition of polysorbate 80 and sucrose was slightly different in these two formulations; the concentration of polysorbate 80 ranged from 0.025% w/v to 0.03% w/v and the concentration of sucrose ranged from 3.8% w/v to 4% w/v. The Formulations F1 to F5 used material from an early preparation process while the F6 formulation was formulated with material from a more optimized process. The compositions of formulations F5 and F6 are very similar, but stability differences were observed between the two. As the compositions were prepared from different processes, this may be the cause of the observed stability differences.

TABLE 15

Formulation Composition Description

| Formulation identifier | anti-DLL4/anti-VEGF DVD Concentration | Buffer | pH | Polysorbate 80 (Tween 80) (% w/v) | Sucrose (% w/v) | Arginine (% w/v) |
|---|---|---|---|---|---|---|
| F1 | 50 | 15 mM Histidine | 6.0 | 0.05 | 7.5 | 0 |
| F2 | 50 | 15 mM Histidine | 5.5 | 0.05 | 7.5 | 0 |
| F3 | 50 | 15 mM Histidine | 6.0 | 0.05 | 7.5 | 1 |
| F4 | 50 | 15 mM Histidine | 6.0 | 0 | 0 | 0 |
| F5 | 25 | 15 mM Histidine | 6.0 | 0.025 | 3.8 | 0 |
| F6 | 25 | 15 mM Histidine | 6.0 | 0.03 | 4.0 | 0 |

In the above formulations, 15 mM histidine buffer was selected because it provides adequate buffering capacity to maintain the target formulation pH. Sucrose was evaluated as a stabilizer against freeze-thaw stress (cryoprotectant) and lyophilization process-induced stress (lyoprotectant). Polysorbate 80 (surfactant) and arginine were added to potentially stabilize the formulation against aggregates and particulates formation.

The stability of liquid formulations was assessed during Freeze/thaw, and at −80, 5, 25 and 40° C. by a broad panel of analytical assays including Visual appearance, % Aggregates by Size Exclusion Chromatography (SE-HPLC), Charge heterogeneity by Cation Exchange Chromatography (CEX-HPLC), Fragmentation by reduced SDS-Capillary Electrophoresis (CE-SDS), and Sub-visible particles by Micro Flow Imaging (MFI) or Light Obscuration (HIAC). These results are provided in Tables 16-19.

TABLE 16

Freeze-Thaw and Liquid Formulation Stability Results at −80° C.

| Formulation Identifier | Time (month) | Visual Appearance | % Aggregate by SE-HPLC | CEX-HPLC % Acidic region | CEX-HPLC % Main peak | CEX-HPLC % Basic region | % Purity (CE-SDS Reduced) | Sub-visible Particle Counts by MFI/HIAC ≥2 μm/mL | ≥10 μm/mL | ≥25 μm/mL | Binding Potency by ELISA % DLL4 | % VEGF |
|---|---|---|---|---|---|---|---|---|---|---|---|---|
| F1 | 0 | EFVP | 1.0 | 21.6 | 61.7 | 16.7 | 97.7 | 3333 | 5 | 0 | 93 | 113 |
|  | 3FT | EFVP | 1.1 | 21.5 | 61.8 | 16.6 | 97.7 | 2388 | 50 | 5 | NP | NP |
|  | 1 | EFVP | 1.1 | 21.0 | 62.1 | 16.8 | 97.8 | 1364 | 15 | 5 | NP | NP |
|  | 3 | EFVP | 1.1 | 21.0 | 62.3 | 16.6 | 97.6 | 714 | 20 | 0 | NP | NP |
| F2 | 0 | EFVP | 1.3 | 21.4 | 61.8 | 16.8 | 97.5 | 1589 | 15 | 0 | 93 | 113 |
|  | 3FT | EFVP | 1.3 | 21.4 | 61.8 | 16.9 | 97.6 | 435 | 5 | 5 | NP | NP |
|  | 1 | EFVP | 1.4 | 21.0 | 62.0 | 17.0 | 97.8 | 315 | 0 | 0 | NP | NP |
|  | 3 | EFVP | 1.5 | 20.9 | 61.9 | 17.2 | 97.7 | 699 | 5 | 0 | NP | NP |
| F3 | 0 | EFVP | 1.1 | 21.5 | 61.7 | 16.7 | 97.6 | 784 | 0 | 0 | 93 | 113 |
|  | 3FT | EFVP | 1.1 | 21.3 | 61.8 | 16.9 | 97.5 | 490 | 10 | 0 | NP | NP |
|  | 1 | EFVP | 1.1 | 21.0 | 61.9 | 17.1 | 97.9 | 250 | 0 | 0 | NP | NP |
|  | 3 | EFVP | 1.2 | 21.0 | 61.8 | 17.2 | 97.7 | 1219 | 35 | 0 | NP | NP |
| F4 | 0 | EFVP | 1.2 | 21.6 | 61.8 | 16.6 | 97.4 | 23707 | 370 | 5 | 93 | 113 |
|  | 3FT | TMTC | 1.5 | 21.4 | 61.8 | 16.8 | 97.4 | 105467 | 5906 | 30 | NP | NP |
|  | 1 | TMTC | 1.2 | 21.1 | 62.0 | 16.9 | 97.8 | 42024 | 1329 | 60 | NP | NP |
|  | 3 | TMTC | 1.5 | 21.1 | 61.9 | 17.0 | 97.8 | 40065 | 3203 | 625 | NP | NP |
| F5 | 0 | EFVP | 0.9 | 21.6 | 61.6 | 16.7 | 97.7 | 2808 | 5 | 5 | 93 | 113 |
|  | 3FT | EFVP | 1.2 | 21.5 | 61.8 | 16.8 | 97.6 | 1949 | 0 | 0 | NP | NP |
|  | 1 | EFVP | 1.1 | 21.0 | 62.2 | 16.8 | 97.8 | 270 | 5 | 0 | NP | NP |
|  | 3 | EFVP | 1.1 | 21.0 | 62.2 | 16.8 | 97.6 | 759 | 0 | 0 | NP | NP |
| F6 | 0 | EFVP | 1.0 | 21.6 | 56.4 | 22.0 | 98.1 | 426 | 58 | 1 | 109 | 97 |
|  | 3FT | EFVP | 1.1 | 21.7 | 55.9 | 22.4 | 98.2 | 193 | 24 | 0 | 115 | 100 |
|  | 1 | EFVP | 1.0 | 21.6 | 55.8 | 22.7 | 98.2 | 50 | 3 | 0 | NP | NP |
|  | 3 | EFVP | 1.1 | 22.0 | 55.9 | 22.1 | 98.3 | 254 | 31 | 0 | 89 | 96 |

Key:
EFVP: Essentially Free of Visible Particles,
TMTC: Too Many To Count,
NP: Not Performed

TABLE 17

Liquid Formulation Stability Results at 5° C.

| Formulation Identifier | Time (month) | Visual Appearance | % Aggregates by SE-HPLC | CEX-HPLC % Acidic region | CEX-HPLC % Main peak | CEX-HPLC % Basic region | % Purity (CE-SDS Reduced) | Sub-visible Particle Counts by MFI/HIAC ≥2 μm/mL | ≥10 μm/mL | ≥25 μm/mL | Binding Potency by ELISA % DLL4 | % VEGF |
|---|---|---|---|---|---|---|---|---|---|---|---|---|
| F1 | 0 | EFVP | 1.0 | 21.6 | 61.7 | 16.7 | 97.7 | 3333 | 5 | 0 | 93 | 113 |
|  | 1 | EFVP | 2.0 | 21.2 | 62.4 | 16.3 | 97.8 | 1064 | 0 | 0 | NP | NP |
|  | 3 | EFVP | 3.0 | 21.6 | 62.5 | 15.9 | 97.6 | 3452 | 15 | 0 | NP | NP |
| F2 | 0 | EFVP | 1.3 | 21.4 | 61.8 | 16.8 | 97.5 | 1589 | 15 | 0 | 93 | 113 |
|  | 1 | EFVP | 2.1 | 20.9 | 62.3 | 16.8 | 97.8 | 230 | 5 | 5 | NP | NP |
|  | 3 | EFVP | 3.0 | 21.1 | 62.5 | 16.3 | 97.8 | 1454 | 0 | 0 | NP | NP |
| F3 | 0 | EFVP | 1.1 | 21.5 | 61.7 | 16.7 | 97.6 | 784 | 0 | 0 | 93 | 113 |
|  | 1 | EFVP | 2.0 | 20.8 | 62.0 | 17.2 | 97.8 | 225 | 5 | 0 | NP | NP |
|  | 3 | EFVP | 3.2 | 20.8 | 61.1 | 18.1 | 97.6 | 1369 | 5 | 0 | NP | NP |
| F4 | 0 | EFVP | 1.2 | 21.6 | 61.8 | 16.6 | 97.4 | 23707 | 370 | 5 | 93 | 113 |
|  | 1 | EFVP | 2.0 | 21.3 | 62.3 | 16.5 | 97.8 | 1189 | 0 | 0 | NP | NP |
|  | 3 | EFVP | 3.3 | 21.6 | 62.6 | 15.8 | 97.8 | 6046 | 145 | 0 | NP | NP |
| F5 | 0 | EFVP | 0.9 | 21.6 | 61.6 | 16.7 | 97.7 | 2808 | 5 | 5 | 93 | 113 |
|  | 1 | EFVP | 1.5 | 21.2 | 61.9 | 16.8 | 97.8 | 709 | 10 | 0 | NP | NP |
|  | 3 | EFVP | 2.2 | 21.4 | 62.4 | 16.1 | 97.6 | 3203 | 50 | 0 | NP | NP |
| F6* | 0 | EFVP | 1.0 | 21.6 | 57.0 | 21.5 | 98.1 | 426 | 58 | 1 | 109 | 97 |
|  | 1 | EFVP | 1.1 | 21.6 | 55.9 | 22.5 | 98.1 | 2458 | 164 | 1 | 116 | 99 |
|  | 3 | EFVP | 1.2 | 22.4 | 55.9 | 21.7 | 98.0 | 34 | 1 | 0 | 101 | 100 |

Key:
EFVP: Essentially Free of Visible Particles,
NP: Not Performed

TABLE 18

Liquid Formication Stability Results at 25° C.

| Formulation Identifier | Time (month) | Visual Appearance | % Aggregates by SE-HPLC | CEX-HPLC % Acidic region | CEX-HPLC % Main peak | CEX-HPLC % Basic region | % Purity (CE-SDS Reduced) | Sub-visible Particle Counts by MFI/HIAC ≥2 µm/mL | Sub-visible Particle Counts by MFI/HIAC ≥10 µm/mL | Sub-visible Particle Counts by MFI/HIAC ≥25 µm/mL | Binding Potency by ELISA % DLL4 | Binding Potency by ELISA % VEGF |
|---|---|---|---|---|---|---|---|---|---|---|---|---|
| F1 | 0 | EFVP | 1.0 | 21.6 | 61.7 | 16.7 | 97.7 | 3333 | 5 | 0 | 93 | 113 |
|    | 1 | EFVP | 4.3 | 23.5 | 62.2 | 14.2 | 97.4 | 1559 | 5 | 5 | NP | NP |
|    | 3 | EFVP | 6.7 | 29.2 | 57.0 | 13.9 | 96.3 | 9358 | 964 | 150 | NP | NP |
| F2 | 0 | EFVP | 1.3 | 21.4 | 61.8 | 16.8 | 97.5 | 1589 | 15 | 0 | 93 | 113 |
|    | 1 | EFVP | 4.4 | 22.8 | 61.6 | 15.6 | 97.4 | 1149 | 5 | 0 | NP | NP |
|    | 3 | EFVP | 7.1 | 27.2 | 56.6 | 16.2 | 95.4 | 6170 | 95 | 0 | NP | NP |
| F3 | 0 | EFVP | 1.1 | 21.5 | 61.7 | 16.7 | 97.6 | 784 | 0 | 0 | 93 | 113 |
|    | 1 | EFVP | 4.9 | 21.5 | 58.3 | 20.2 | 97.3 | 834 | 10 | 0 | NP | NP |
|    | 3 | EFVP | 9.3 | 24.7 | 52.2 | 23.0 | 96.4 | 3677 | 150 | 10 | NP | NP |
| F4 | 0 | EFVP | 1.2 | 21.6 | 61.8 | 16.6 | 97.4 | 23707 | 370 | 5 | 93 | 113 |
|    | 1 | EFVP | 4.5 | 23.5 | 61.8 | 14.7 | 97.2 | 89299 | 3053 | 165 | NP | NP |
|    | 3 | EFVP | 7.5 | 28.6 | 57.4 | 14.1 | 96.6 | 10527 | 1279 | 275 | NP | NP |
| F5 | 0 | EFVP | 0.9 | 21.6 | 61.6 | 16.7 | 97.7 | 2808 | 5 | 5 | 93 | 113 |
|    | 1 | EFVP | 2.6 | 23.5 | 62.0 | 14.6 | 97.2 | 944 | 15 | 0 | NP | NP |
|    | 3 | EFVP | 3.9 | 29.4 | 57.7 | 12.9 | 96.2 | 13575 | 1259 | 225 | NP | NP |
| F6 | 0 | EFVP | 1.0 | 21.6 | 57.0 | 21.5 | 98.1 | 426 | 58 | 1 | 109 | 97 |
|    | 1 | EFVP | 1.2 | 23.5 | 54.8 | 21.7 | 97.7 | 386 | 50 | 0 | 100 | 96 |
|    | 3 | EFVP | 1.6 | 28.8 | 52.5 | 18.7 | 96.2 | 40 | 1 | 0 | 94 | 100 |

Key:
EFVP: Essentially Free of Visible Particles,
NP: Not Performed

TABLE 19

Liquid Formulation Stability Results at 40° C.

| Formulation Identifier | Time (month) | Visual Appearance | % Aggregates by SE-HPLC | CEX-HPLC % Acidic region | CEX-HPLC % Main peak | CEX-HPLC % Basic region | % Purity (CE-SDS Reduced) | Sub-visible Particle Counts by MFI/HIAC ≥2 µm/mL | Sub-visible Particle Counts by MFI/HIAC ≥10 µm/mL | Sub-visible Particle Counts by MFI/HIAC ≥25 µm/mL | Binding Potency by ELISA % DLL4 | Binding Potency by ELISA % VEGF |
|---|---|---|---|---|---|---|---|---|---|---|---|---|
| F1 | 0 | EFVP | 1.0 | 21.6 | 61.7 | 16.7 | 97.7 | 3333 | 5 | 0 | 93 | 113 |
|    | 1 | EFVP | 7.2 | 35.8 | 43.0 | 21.2 | 95.0 | 1219 | 15 | 0 | 94 | 104 |
|    | 3 | EFVP | 12.8 | 57.0 | 23.0 | 20.0 | 85.9 | 21464 | 635 | 30 | 73 | 72 |
| F2 | 0 | EFVP | 1.3 | 21.4 | 61.8 | 16.8 | 97.5 | 1589 | 15 | 0 | 93 | 113 |
|    | 1 | EFVP | 7.9 | 33.8 | 40.9 | 25.3 | 95.1 | 655 | 5 | 0 | 95 | 97 |
|    | 3 | EFVP | 13.3 | 52.8 | 22.7 | 24.5 | 86.7 | 6041 | 90 | 0 | 68 | 73 |
| F3 | 0 | EFVP | 1.1 | 21.5 | 61.7 | 16.7 | 97.6 | 784 | 0 | 0 | 93 | 113 |
|    | 1 | EFVP | 11.3 | 32.1 | 42.3 | 25.6 | 95.0 | 1464 | 5 | 0 | 97 | 101 |
|    | 3 | EFVP | 18.1 | 48.6 | 25.2 | 26.2 | 86.3 | 9103 | 165 | 15 | 81 | 72 |
| F4 | 0 | EFVP | 1.2 | 21.6 | 61.8 | 16.6 | 97.4 | 23707 | 370 | 5 | 93 | 113 |
|    | 1 | EFVP | 7.7 | 34.9 | 44.2 | 20.9 | 94.8 | 61754 | 5051 | 670 | 101 | 97 |
|    | 3 | EFVP | 13.5 | 52.8 | 25.9 | 21.4 | 86.3 | 14000 | 1729 | 480 | 73 | 76 |
| F5 | 0 | EFVP | 0.9 | 21.6 | 61.6 | 16.7 | 97.7 | 2808 | 5 | 5 | 93 | 113 |
|    | 1 | EFVP | 3.9 | 37.0 | 44.4 | 18.6 | 95.0 | 974 | 20 | 0 | 92 | 95 |
|    | 3 | EFVP | 7.4 | 59.6 | 24.5 | 15.9 | 87.0 | 11836 | 610 | 55 | 68 | 69 |
| F6 | 0 | EFVP | 1.0 | 21.6 | 56.4 | 22.0 | 98.1 | 426 | 58 | 1 | 109 | 97 |
|    | 1 | EFVP | 1.9 | 35.0 | 42.8 | 22.2 | 94.5 | 60 | 0 | 0 | 96 | 95 |

Key:
EFVP: Essentially Free of Visible Particles

Lyophilized Formulation Stability Testing.

The stability of select formulations was also evaluated after the formulations were lyophilized. The lyophilized drug product stability was assessed for all sucrose-containing formulations (F1, F2, F3, F5 and F6). Stability was assessed after 2 weeks storage at 55° C. Stability was tested by a broad panel of analytical assays including Visual appearance (before and after reconstitution), Reconstitution time, % Aggregates by Size Exclusion Chromatography (SE-HPLC), Charge heterogeneity by Cation Exchange Chromatography (CEX-HPLC), Fragmentation by reduced SDS-Capillary Electrophoresis (CE-SDS), Sub-visible particles by Micro Flow Imaging (MFI) or light obscuration (HIAC), and Water Content by Karl Fischer titration.

The lyophilized formulation stability testing results are provided in Table 20. Reconstitution time for all evaluated formulations was approximately 1 to 2 minutes. A slight increase in aggregation by SEC and % basic region by CEX was observed for all formulations under the stressed storage condition of 55° C. Minimal changes were observed in all other measured product stability attributes.

TABLE 20

Lyophilized Formulation Stability Results at 55° C.

| Formulation Identifier | Time (month) | Visual Appearance Before Recon | Visual Appearance After Recon | % Aggregates by SE-HPLC | CEX-HPLC % Acidic region | CEX-HPLC % Main peak | CEX-HPLC % Basic region | % Purity (CE-SDS Reduced) | Sub-visible Particle Counts by MFI/HIAC ≥2 μm/mL | ≥10 μm/mL | ≥25 μm/mL |
|---|---|---|---|---|---|---|---|---|---|---|---|
| F1 | 0 | WTOWC | EFVP | 1.1 | 21.3 | 61.9 | 16.8 | 97.6 | 749 | 20 | 10 |
|  | 2 weeks at 55° C. | WTOWC | EFVP | 1.6 | 20.6 | 58.1 | 21.3 | 97.5 | 1639 | 15 | 0 |
| F2 | 0 | WTOWC | EFVP | 1.3 | 21.2 | 61.8 | 17.0 | 97.6 | 1254 | 15 | 0 |
|  | 2 weeks at 55° C. | WTOWC | EFVP | 2.0 | 20.4 | 57.8 | 21.8 | 97.6 | 1609 | 10 | 0 |
| F3 | 0 | WTOWC | EFVP | 1.1 | 21.2 | 61.9 | 16.9 | 97.6 | 719 | 5 | 0 |
|  | 2 weeks at 55° C. | WTOWC | EFVP | 1.4 | 20.8 | 59.5 | 19.8 | 97.5 | 475 | 10 | 5 |
| F5 | 0 | WTOWC | EFVP | 1.0 | 21.3 | 61.8 | 16.9 | 97.5 | 844 | 35 | 5 |
|  | 2 weeks at 55° C. | WTOWC | EFVP | 1.5 | 20.5 | 58.0 | 21.5 | 97.7 | 270 | 5 | 0 |
| F6 | 0 | WTOWC | EFVP | 1.0 | 21.5 | 56.5 | 22.0 | 98.2 | 205 | 7 | 0 |
|  | 2 weeks at 55° C. | WTOWC | EFVP | 1.5 | 21.1 | 53.4 | 25.5 | 98.2 | 126 | 5 | 1 |

Key:
WTOWC: White to off-white cake,
EFVP: Essentially Free of Visible Particle

Dose Solution Stability Testing.

The anti-DLL4/anti-VEGF binding protein is tested for intravenous administration (IV). Prior to administration, the lyophilized drug product is reconstituted with sterile water for injection (SWFI). Subsequently, the reconstituted product is diluted in a solution that is suitable for IV infusion. The final concentration to which the dose solution is diluted is determined based on the clinical dose administered.

A study was conducted to evaluate the stability of the diluted anti-DLL4/anti-VEGF binding protein when in dose solutions containing one of two commonly used IV diluents, 0.9% saline and 5% dextrose (D5W). The protein concentrations evaluated were 0.5 and 1 mg/mL. To assess the dose solution stability and compatibility with the infusion components, the dose solutions per test condition were prepared and stored in IV bags (n=2) for 6 hours at RT/RL, and subsequently, a mock infusion study was performed using the commonly used infusion administration components, including an in-line filter. Test samples were pulled directly from the bag after preparing dose solutions in IV bags (T0). In addition, samples collected at the end of the 30 minutes infusion process were tested. The samples were tested by a panel of analytical assays including Visual appearance, % Aggregates by Size Exclusion Chromatography (SE-HPLC) and Sub-visible particles by Light obscuration (HIAC).

The dose solution stability studies results are provided in Table 21. The aggregate level in the starting material was 0.7%. After the dose solutions were prepared in saline, a clear trend indicating increase in aggregate level upon dilution in saline (T0) and at the end of infusion was observed. In addition, sub-visible particle counts in these samples were high. In comparison, the dose solutions prepared in 5% dextrose (D5W) showed consistently lower % aggregate levels with acceptable stability trends with respect to particulates.

TABLE 21

Clinical In-Use Stability Results

| Diluent | Dose Solution Conc. (mg/mL) | Time Point | Visual Appearance | % Aggregates by SE-HPLC | Sub-visible Particle Counts by HIAC ≥2 μm/mL | ≥10 μm/mL | ≥25 μm/mL |
|---|---|---|---|---|---|---|---|
| 0.9% Saline | 0.5 mg/mL (Bag #1) | T0 | EFVP | 2.7 | 2139 | 86 | 8 |
|  |  | Post pump infusion | EFVP | 4.7 | 4398 | 63 | 1 |
|  | 0.5 mg/mL (Bag #2) | T0 | EFVP | 2.7 | 2729 | 189 | 12 |
|  |  | Post pump infusion | EFVP | 3.5 | 1879 | 31 | 2 |
|  | 1.0 mg/mL (Bag #1) | T0 | EFVP | 2.4 | 1774 | 85 | 3 |
|  |  | Post pump infusion | EFVP | 3.0 | 2300 | 24 | 0 |
|  | 1.0 mg/mL (Bag #2) | T0 | EFVP | 1.8 | 914 | 23 | 0 |
|  |  | Post pump infusion | EFVP | 2.5 | 3056 | 42 | 2 |
| 5% Dextrose | 0.5 mg/mL (Bag #1) | T0 | EFVP | 0.6 | 1679 | 31 | 0 |
|  |  | Post pump infusion | EFVP | 0.6 | 7 | 0 | 0 |
|  | 0.5 mg/mL (Bag #2) | T0 | EFVP | 0.6 | 2944 | 135 | 0 |
|  |  | Post pump infusion | EFVP | 0.6 | 3 | 0 | 0 |
|  | 1 mg/mL (Bag #1) | T0 | EFVP | 0.6 | 1652 | 23 | 0 |
|  |  | Post pump infusion | EFVP | 0.6 | 2 | 0 | 0 |
|  | 1 mg/mL (Bag #2) | T0 | EFVP | 0.6 | 2105 | 38 | 0 |
|  |  | Post pump infusion | EFVP | 0.6 | 6 | 0 | 0 |

EFVP: Essentially free of visible particles

Example 9

Extended Preformulation Characterization

Extended preformulation characterization on anti-DLL4/-antiVEGF DVDs was performed to explore how different formulations conditions impact the stability of the DVDs. Data for h1A11.1-LS-Av is presented in Tables 22 and 23. The storage stability (5° C.) and accelerated stability (40° C.) of the DVD was evaluated in the formulations and protein concentrations listed below. Stability was evaluated by size exclusion chromatography (SE-HPLC) and % aggregate, % monomer, % fragment, and total species recovered were quantitated. Overall, the formulations cover a pH range of 5 to 7 and a protein concentration range of 10 to 50 mg/ml.

At 5° C. and 40° C. temperatures and at concentrations of 50, 30, and 10 mg/ml the following formulations were evaluated: 15 mM acetate pH 5, 15 mM histidine pH 6, 15 mM phosphate pH 7, 30 mM acetate, 80 mg/ml sucrose, 0.02% Tween 80 at pH 5, 30 mM histidine, 80 mg/ml sucrose, 0.02% Tween 80 at pH 6, and PBS (phosphate buffered saline). All formulations contained 0.02% sodium azide to prevent microbial growth during storage.

TABLE 22

Accelerated stability at 40° C. of h1A11.1-LS-Av

| Protein conc (mg/ml) | time | temp (° C.) | buffer | pH | % Aggregate | % Monomer | % Fragment | Total Area |
|---|---|---|---|---|---|---|---|---|
| — | pre-dialysis | — | — | — | 0.21 | 98.42 | 1.36 | 56054 |
| 50, 30, 10 | T0 | — | ace | 5 | 0.28 | 98.41 | 1.31 | 56381 |
| 50, 30, 10 | T0 | — | his | 6 | 0.46 | 98.23 | 1.31 | 54316 |
| 50, 30, 10 | T0 | — | phos | 7 | 0.74 | 97.86 | 1.40 | 53212 |
| 50, 30, 10 | T0 | — | ace-suc-tw | 5 | 0.24 | 98.16 | 1.60 | 56244 |
| 50, 30, 10 | T0 | — | his-suc-tw | 6 | 0.30 | 98.11 | 1.59 | 54076 |
| 50, 30, 10 | T0 | — | PBS | 7 | 0.52 | 98.05 | 1.43 | 50085 |
| 50 | T7 d | 40 | ace | 5 | 1.63 | 96.74 | 1.63 | 55563 |
| 30 | T7 d | 40 | ace | 5 | 1.13 | 97.24 | 1.62 | 55194 |
| 10 | T7 d | 40 | ace | 5 | 0.84 | 97.49 | 1.67 | 55029 |
| 50 | T7 d | 40 | his | 6 | 2.00 | 96.62 | 1.38 | 53566 |
| 30 | T7 d | 40 | his | 6 | 1.17 | 97.46 | 1.38 | 52443 |
| 10 | T7 d | 40 | his | 6 | 0.60 | 98.00 | 1.40 | 53812 |
| 50 | T7 d | 40 | phos | 7 | 4.31 | 94.02 | 1.67 | 52934 |
| 30 | T7 d | 40 | phos | 7 | 2.85 | 95.46 | 1.69 | 52663 |
| 10 | T7 d | 40 | phos | 7 | 1.20 | 97.11 | 1.69 | 52411 |
| 50 | T7 d | 40 | ace-suc-tw | 5 | 1.10 | 96.23 | 2.66 | 54837 |
| 30 | T7 d | 40 | ace-suc-tw | 5 | 0.77 | 96.40 | 2.83 | 52474 |
| 10 | T7 d | 40 | ace-suc-tw | 5 | 0.43 | 96.39 | 3.17 | 50855 |
| 50 | T7 d | 40 | his-suc-tw | 6 | 1.69 | 96.27 | 2.05 | 53017 |
| 30 | T7 d | 40 | his-suc-tw | 6 | 1.14 | 96.84 | 2.02 | 52153 |
| 10 | T7 d | 40 | his-suc-tw | 6 | 0.59 | 97.30 | 2.11 | 52208 |
| 50 | T7 d | 40 | PBS | 7 | 2.77 | 95.30 | 1.93 | 51623 |
| 30 | T7 d | 40 | PBS | 7 | 1.73 | 96.28 | 1.99 | 49973 |
| 10 | T7 d | 40 | PBS | 7 | 0.78 | 97.25 | 1.97 | 50851 |
| 50 | T21 d | 40 | ace | 5 | 3.66 | 94.30 | 2.04 | 55920 |
| 30 | T21 d | 40 | ace | 5 | 2.56 | 95.33 | 2.10 | 54188 |
| 10 | T21 d | 40 | ace | 5 | 1.85 | 96.00 | 2.15 | 55213 |
| 50 | T21 d | 40 | his | 6 | 4.14 | 94.28 | 1.58 | 54807 |
| 30 | T21 d | 40 | his | 6 | 2.67 | 95.79 | 1.54 | 53071 |
| 10 | T21 d | 40 | his | 6 | 1.59 | 96.82 | 1.58 | 54053 |
| 50 | T21 d | 40 | phos | 7 | 8.52 | 89.32 | 2.16 | 53273 |
| 30 | T21 d | 40 | phos | 7 | 5.58 | 92.54 | 1.89 | 53162 |
| 10 | T21 d | 40 | phos | 7 | 3.01 | 94.89 | 2.10 | 52747 |
| 50 | T21 d | 40 | ace-suc-tw | 5 | 4.12 | 93.78 | 2.10 | 56278 |
| 30 | T21 d | 40 | ace-suc-tw | 5 | 2.93 | 94.94 | 2.13 | 55481 |
| 10 | T21 d | 40 | ace-suc-tw | 5 | 1.99 | 95.75 | 2.26 | 54696 |
| 50 | T21 d | 40 | his-suc-tw | 6 | 4.94 | 93.21 | 1.85 | 54034 |
| 30 | T21 d | 40 | his-suc-tw | 6 | n/a | n/a | n/a | n/a |
| 10 | T21 d | 40 | his-suc-tw | 6 | 2.00 | 96.30 | 1.70 | 52686 |
| 50 | T21 d | 40 | PBS | 7 | 8.44 | 89.65 | 1.90 | 51697 |
| 30 | T21 d | 40 | PBS | 7 | 5.54 | 92.43 | 2.03 | 50282 |
| 10 | T21 d | 40 | PBS | 7 | 2.89 | 95.05 | 2.06 | 51580 |

Buffer key (all buffers contain 0.02% sodium azide to prevent microbial growth):
ace = 15 mM acetate pH 5;
his = 15 mM histidine pH 6;
phos = 15 mM phosphate pH 7;
ace-suc-tw = 30 mM acetate, 80 mg/ml sucrose, 0.02% Tween80;
his-suc-tw = 30 mM histidine, 80 mg/ml sucrose, 0.02% Tween80;
PBS = phosphate buffered saline

TABLE 23

Storage stability at 5° C. of h1A11.1-LS-Av

| Protein conc (mg/ml) | time | temp (° C.) | buffer | pH | % Aggregate | % Monomer | % Fragment | Total Area |
|---|---|---|---|---|---|---|---|---|
| — | pre-dialysis | — | — | — | 0.21 | 98.42 | 1.36 | 56054 |
| 50, 30, 10 | T0 | — | ace | 5 | 0.28 | 98.41 | 1.31 | 56381 |
| 50, 30, 10 | T0 | — | his | 6 | 0.46 | 98.23 | 1.31 | 54316 |
| 50, 30, 10 | T0 | — | phos | 7 | 0.74 | 97.86 | 1.40 | 53212 |
| 50, 30, 10 | T0 | — | ace-suc-tw | 5 | 0.24 | 98.16 | 1.60 | 56244 |
| 50, 30, 10 | T0 | — | his-suc-tw | 6 | 0.30 | 98.11 | 1.59 | 54076 |
| 50, 30, 10 | T0 | — | PBS | 7 | 0.52 | 98.05 | 1.43 | 50085 |
| 50 | T7 d | 5 | ace | 5 | 0.18 | 98.17 | 1.64 | 57599 |
| 30 | T7 d | 5 | ace | 5 | 0.16 | 98.21 | 1.64 | 55889 |
| 10 | T7 d | 5 | ace | 5 | 0.13 | 98.17 | 1.70 | 53289 |
| 50 | T7 d | 5 | his | 6 | 0.18 | 98.14 | 1.68 | 55742 |
| 30 | T7 d | 5 | his | 6 | 0.12 | 98.06 | 1.82 | 53603 |
| 10 | T7 d | 5 | his | 6 | 0.13 | 98.07 | 1.80 | 53505 |
| 50 | T7 d | 5 | phos | 7 | 0.23 | 97.72 | 2.05 | 54355 |
| 30 | T7 d | 5 | phos | 7 | 0.18 | 97.77 | 2.04 | 53561 |
| 10 | T7 d | 5 | phos | 7 | 0.13 | 97.72 | 2.15 | 53151 |
| 50 | T7 d | 5 | ace-suc-tw | 5 | 0.09 | 97.40 | 2.51 | 57158 |
| 30 | T7 d | 5 | ace-suc-tw | 5 | 0.08 | 97.43 | 2.49 | 55025 |
| 10 | T7 d | 5 | ace-suc-tw | 5 | 0.08 | 97.34 | 2.58 | 53882 |
| 50 | T7 d | 5 | his-suc-tw | 6 | 0.10 | 97.48 | 2.43 | 55272 |
| 30 | T7 d | 5 | his-suc-tw | 6 | 0.08 | 97.63 | 2.29 | 52763 |
| 10 | T7 d | 5 | his-suc-tw | 6 | 0.05 | 97.41 | 2.53 | 52903 |
| 50 | T7 d | 5 | PBS | 7 | 0.12 | 97.31 | 2.58 | 51698 |
| 30 | T7 d | 5 | PBS | 7 | 0.09 | 97.24 | 2.67 | 50144 |
| 10 | T7 d | 5 | PBS | 7 | 0.08 | 97.28 | 2.64 | 50428 |
| 50 | T21 d | 5 | ace | 5 | 0.87 | 98.45 | 0.68 | 57706 |
| 30 | T21 d | 5 | ace | 5 | 0.80 | 98.55 | 0.65 | 56566 |
| 10 | T21 d | 5 | ace | 5 | 0.83 | 98.47 | 0.70 | 54226 |
| 50 | T21 d | 5 | his | 6 | 1.05 | 98.29 | 0.66 | 55911 |
| 30 | T21 d | 5 | his | 6 | 0.92 | 98.40 | 0.68 | 54225 |
| 10 | T21 d | 5 | his | 6 | 0.90 | 98.41 | 0.70 | 54128 |
| 50 | T21 d | 5 | phos | 7 | 1.25 | 98.09 | 0.66 | 54980 |
| 30 | T21 d | 5 | phos | 7 | 1.20 | 98.11 | 0.69 | 53903 |
| 10 | T21 d | 5 | phos | 7 | 1.01 | 98.29 | 0.69 | 53271 |
| 50 | T21 d | 5 | ace-suc-tw | 5 | 0.92 | 98.36 | 0.72 | 61574 |
| 30 | T21 d | 5 | ace-suc-tw | 5 | 0.89 | 98.39 | 0.72 | 55532 |
| 10 | T21 d | 5 | ace-suc-tw | 5 | 0.83 | 98.46 | 0.71 | 55841 |
| 50 | T21 d | 5 | his-suc-tw | 6 | 1.00 | 98.27 | 0.73 | 55484 |
| 30 | T21 d | 5 | his-suc-tw | 6 | 0.92 | 98.37 | 0.70 | 53335 |
| 10 | T21 d | 5 | his-suc-tw | 6 | 0.82 | 98.49 | 0.69 | 53736 |
| 50 | T21 d | 5 | PBS | 7 | 1.49 | 97.79 | 0.71 | 52405 |
| 30 | T21 d | 5 | PBS | 7 | 1.29 | 98.02 | 0.70 | 51284 |
| 10 | T21 d | 5 | PBS | 7 | 1.12 | 98.18 | 0.70 | 51377 |

The buffer key for Table 23 is the same as in Table 22.

Example 10

Effect of VEGF on the Neutralization Activity of Anti-DLL4/Anti-VEGF DVD in DLL4 Cellular Assay To evaluate whether VEGF binding will affect the DLL4 neutralization potency of anti-DLL4/anti-VEGF DVDs, VEGF was included in the DLL4-Notch reporter assay as described in Example 3.3. Briefly, the HEK293G cells expressing human DLL4 were co-cultured with EA.hy926 Notch reporter cells for 24 hrs in the presence of h1A11.1-SL-Av DVD or the mixture of anti-DLL4 mAb (h1A11.1) and anti-VEGF mAb (Av) serially diluted from 300 nM. Recombinant human $VEGF_{165}$ (a physiologically relevant human splice isoform of VEGF) or a negative control protein (BSG2) was also included. DLL4 neutralization potency was determined by evaluating $IC_{50}$ values, the concentration of antibody needed to achieve 50% reduction of DLL4-induced Notch activation. As shown in Table 24, the presence of 6 or 150 nM VEGF greatly increased the DLL4 neutralization potency of h1A11.1-SL-Av DVD. This increased potency is unique to the anti-DLL4/anti-VEGF DVD as the parental mAb mixture exhibited similar potency with or without VEGF included.

TABLE 24

VEGF Enhances the DLL4 Potency of Anti-DLL4/Anti-VEGF DVD but not the Anti-DLL4/Anti-VEGF Mixture

| | IC50 (nM) | | |
|---|---|---|---|
| | 0 nM VEGF | 6 nM VEGF | 6 nM BSG2 |
| h1A11.1-SL-Av | 12.50 | 0.61 | 16.76 |
| h1A11.1 + Av mixture | 8.64 | 9.97 | 9.55 |

| | $IC_{50}$ (nM) | | |
|---|---|---|---|
| | 0 nM VEGF | 150 nM VEGF | 150 nM BSG2 |
| h1A11.1-SL-Av | 12.69 | 0.40 | 14.11 |
| h1A11.1 + Av mixture | 9.17 | 10.32 | 10.93 |

In another experiment, the monovalent Fab fragment of h1A11.1-SL-Av DVD was also evaluated in the DLL4 neutralization cellular assay. In contrast to the DVD Ig, the monovalent DVD Fab has weaker DLL4 neutralization potency. The presence of VEGF improved the potency of the DVD-Fab, but not to the degree as seen with the DVD-Ig (Table 25).

TABLE 25

Effect of VEGF on the DLL4 Neutralization Potency of Anti-DLL4/ Anti-VEGF DVD Ig and DVD Fab

| | $IC_{50}$ (nM) | | |
|---|---|---|---|
| | 0 nM VEGF | 150 nM VEGF | 150 nM BSG2 |
| h1A11.1-SL-Av | 13.46 | 0.41 | 16.55 |
| h1A11.1-SL-Av Fab | >40* | 4.56 | >40* |

*Precise $IC_{50}$ could not be determined due to inability to fully neutralize DLL4

In another experiment, VEGF concentrations were serially titrated down and applied to the DLL4-Notch reporter assay described above. As shown in Table 26, VEGF can enhance the DLL4 neutralization activity of h1A11.1-SL-Av DVD at a concentration as low as 1.2 nM.

TABLE 26

VEGF Enhances the DLL4 Neutralization Potency of Anti-DLL4/Anti-VEGF DVD

| | nM | h1A11.1-SL-Av $IC_{50}$ (nM) |
|---|---|---|
| BSG2 | 150 | 11.0 |
| VEGF | 150 | 0.6 |
| | 30 | 0.7 |
| | 6 | 0.6 |
| | 1.2 | 1.1 |
| | 0.24 | 12.7 |
| | 0.048 | 12.3 |
| | 0.0096 | 11.5 |
| | 0 | 11.8 |

Example 11

In Vivo Combination Efficacy of DLL4-VEGF DVD-Igs

The effect of anti-DLL4-VEGF DVD-Igs in combination with chemotherapy on tumor growth was evaluated on SW-48 human colon xenograft tumors in female SCID mice. Briefly, $5 \times 10^6$ cells were inoculated subcutaneously into the right hind flank. Tumors were allowed to establish for 13 days, at which point tumor volume was determined using electronic caliper measurements using the formula: $L \times W^2/2$. Mice were allocated into treatment groups (n=10 per group) so that each cohort had equivalent mean tumor volume of 211 mm$^3$ prior to initiation of therapy. Animals were dosed with irinotecan, anti-VEGF mAb, and/or anti-DLL4-VEGF DVD-Ig at the dose and schedule in Table 27. Tumor volume was measured twice a week for the duration of the experiment. Results are shown in Table 27.

TABLE 27

Combination efficacy of anti-DLL4-VEGF DVD-Ig and irinotecan in the SW-48 colon xenograft model

| Treatment | Dose Route, Regimen | % TGI$^a$ | % TGD$^b$ |
|---|---|---|---|
| Irinotecan | 60 mg/kg IP, q3dX4 | 77*** | 106*** |
| Anti-VEGF mAb | 10 mg/kg IP, q7dX4 | 39* | 50* |
| h1A11.1-SL-Av | 13.3 mg/kg IP, q7dX4 | 72*** | 150*** |
| Anti-VEGF mAb + Irinotecan | 10 mg/kg IP, q7dX4 + 60 mg/kg IP, q3dX4 | 78*** | 150*** |
| h1A11.1-SL-Av + Irinotecan | 13.3 mg/kg IP, q7dX4 + 60 mg/kg IP, q3dX4 | 90*** | 228*** |

Table 27 key.
$^a$% TGI = Percent tumor growth inhibition = $100 - (T/C \times 100)$, where T = mean tumor volume of treatment group and C = mean tumor volume of treatment control group. Based on day 18 post size match measurements. P values (as indicated by asterisks) are derived from Student's T test comparison of treatment group vs. treatment control group.
$^b$% TGD = Percent tumor growth delay = $(T - C)/C \times 100$, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group: *p < 0.05; p < 0.001; *p < 0.0001. "q3dX4" indicates administration every three days for four cycles (i.e., 4 doses), while "q7dX4" indicates administration every seven days for four cycles.

The effect of anti-DLL4-VEGF DVD-Igs in combination with chemotherapy on tumor growth was evaluated on HCT-116 human colon xenograft tumors in female SCID mice. Briefly, $5 \times 10^6$ cells were inoculated subcutaneously into the right hind flank. Tumors were allowed to establish for 14 days, at which point tumor volume was determined using electronic caliper measurements using the formula: $L \times W^2/2$. Mice were allocated into treatment groups (n=9 per group) so that each cohort had equivalent mean tumor volume of 192 mm$^3$ prior to initiation of therapy. Animals were dosed with 5-FU, leucovorin, irinotecan, anti-VEGF mAb, and/or anti-DLL4-VEGF DVD-Ig at the dose and schedule in Table 28. Tumor volume was measured twice a week for the duration of the experiment. Results are shown in Table 28.

TABLE 28

Combination efficacy of anti-DLL4-VEGF DVD-Ig and FOLFIRI in the HCT-116 colon xenograft model

| Treatment | Dose Route, Regimen | % TGI$^a$ |
|---|---|---|
| 5-FU | 50 mg/kg IV, q7dX3 | 63*** |
| Leucovorin | 25 mg/kg PO, q7dX3 | |
| Irinotecan (FOLFIRI) | 30 mg/kg IV, q7dX3 | |
| Anti-VEGF mAb | 5 mg/kg IP, q7dX4 | 49*** |
| h1A11.1-SL-Av | 6.7 mg/kg IP, q7dX4 | 67*** |
| Anti-VEGF mAb + FOLFIRI | 5 mg/kg IP, q7dX4 + (above) q7dX3 | 81*** |
| h1A11.1-SL-Av + FOLFIRI | 6.7 mg/kg IP, q7dX4 + (above) q7dX3 | 90*** |

Table 28 key.
$^a$% TGI = Percent tumor growth inhibition = $100 - (T/C \times 100)$, where T = mean tumor volume of treatment group and C = mean tumor volume of treatment control group. Based on day 26 post size match measurements.
P values (as indicated by asterisks) are derived from Student's T test comparison of treatment group vs. treatment control group: *p < 0.05; p < 0.001; *p < 0.0001. "q7dX3" indicates administration every seven days for three cycles (i.e., 3 doses), while "q7dX4" indicates administration every seven days for four cycles.

The effect of anti-DLL4-VEGF DVD-Igs in combination with chemotherapy on tumor growth was evaluated on HT-29 human colon xenograft tumors in female SCID mice. Briefly, $2 \times 10^6$ cells were inoculated subcutaneously into the right hind flank. Tumors were allowed to establish for 25 days, at which point tumor volume was determined using electronic caliper measurements using the formula: $L \times W^2/2$. Mice were allocated into treatment groups (n=10 per group) so that each cohort had equivalent mean tumor volume of 209 mm$^3$ prior to initiation of therapy. Animals were dosed with irinotecan and/or anti-DLL4-VEGF DVD-Ig, at the dose and schedule in Table 29. Tumor volume was measured twice a week for the duration of the experiment. Results are shown in Table 29.

TABLE 29

Combination efficacy of anti-DLL4-VEGF DVD-Ig and irinotecan in the HT-29 colon xenograft model

| Treatment | Dose Route, Regimen | % TGI[a] | % TGD[b] |
|---|---|---|---|
| Irinotecan | 60 mg/kg IP, q3dX4 | 47* | 60* |
| h1A11.1-SL-Av | 6.7 mg/kg IP, q7dX4 | 42* | 45* |
| h1A11.1-SL-Av + Irinotecan | 6.7 mg/kg IP, q7dX4 + 60 mg/kg IP, q3dX4 | 74** | 76* |

Table 29 key.
[a]% TGI = Percent tumor growth inhibition = 100 − (T/C × 100), where T = mean tumor volume of treatment group and C = mean tumor volume of treatment control group. Based on day 20 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group: *p < 0.05; p < 0.001; *p < 0.0001.
"q3dX4" indicates administration every three days for four cycles (i.e., 4 doses), while "q7dX4" indicates administration every seven days for four cycles.

The effect of anti-DLL4-VEGF DVD-Igs in combination with chemotherapy on tumor growth was evaluated on U87-MG human glioblastoma xenograft tumors in female SCID mice. Briefly, $3 \times 10^6$ cells were inoculated subcutaneously into the right hind flank. Tumors were allowed to establish for 13 days, at which point tumor volume was determined using electronic caliper measurements using the formula: $L \times W^2/2$. Mice were allocated into treatment groups (n=10 per group) so that each cohort had equivalent mean tumor volume of 207 mm$^3$ prior to initiation of therapy. Animals were dosed with temozolomide, anti-VEGF mAb, and/or anti-DLL4-VEGF DVD-Ig at the dose and schedule in Table 30. Tumor volume was measured twice a week for the duration of the experiment. Results are shown in Table 30.

TABLE 30

Combination efficacy of anti-DLL4-VEGF DVD-Ig and temozolomide in the U87-MG glioblastoma xenograft model

| Treatment | Dose Route, Regimen | % TGI[a] | % TGD[b] |
|---|---|---|---|
| Temozolomide | 5 mg/kg IP, qdX1 | 65*** | 45*** |
| Anti-VEGF mAb | 5 mg/kg IP, q7dX4 | 47** | 45** |
| h1A11.1-SL-Av | 6.7 mg/kg IP, q7dX4 | 69*** | 100*** |
| Anti-VEGF mAb + Temozolomide | 5 mg/kg IP, q7dX4 + 5 mg/kg IP, qdX1 | 68*** | 89*** |
| h1A11.1-SL-Av + Temozolomide | 6.7 mg/kg IP, q7dX4 + 5 mg/kg IP, qdX1 | 78*** | 155*** |

Table 30 key.
[a]% TGI = Percent tumor growth inhibition = 100 − (T/C × 100), where T = mean tumor volume of treatment group and C = mean tumor volume of treatment control group. Based on day 19 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group: *p < 0.05; p < 0.001; *p < 0.0001.

The effect of anti-DLL4-VEGF DVD-Igs in combination with chemotherapy on tumor growth was evaluated on PA0123 patient-derived human pancreatic xenograft tumors in female NSG mice. Briefly, frozen tumor fragments were implanted subcutaneously into the right hind flank. Tumors were allowed to establish for 28 days, at which point tumor volume was determined using electronic caliper measurements using the formula: $L \times W^2/2$. Mice were allocated into treatment groups (n=7 per group) so that each cohort had equivalent mean tumor volume of 193 mm$^3$ prior to initiation of therapy. Animals were dosed with gemcitabine and/or anti-DLL4-VEGF DVD-Ig, at the dose and schedule in Table 31. Tumor volume was measured twice a week for the duration of the experiment. Results are shown in Table 31.

TABLE 31

Combination efficacy of anti-DLL4-VEGF DVD-Ig and gemcitabine in the PA0123 patient-derived pancreatic xenograft model

| Treatment | Dose Route, Regimen | % TGI[a] | % TGD[b] |
|---|---|---|---|
| Gemcitabine | 100 mg/kg IP, [q3dX4]X2 | 48** | 43** |
| h1A11.1-SL-Av | 13.3 mg/kg IP, q7dX5 | 54** | 75** |
| h1A11.1-SL-Av + Gemcitabine | 13.3 mg/kg IP, q7dX5 + 100 mg/kg IP, [q3dX4]X2 | 75*** | 114*** |

Table 31 key.
[a]% TGI = Percent tumor growth inhibition = 100 − (T/C × 100), where T = mean tumor volume of treatment group and C = mean tumor volume of treatment control group. Based on day 38 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group: *p < 0.05; p < 0.001; *p < 0.0001.

The effect of anti-DLL4-VEGF DVD-Igs in combination with chemotherapy on tumor growth was evaluated on MDA-MB-231-luc human breast xenograft tumors in female SCID mice. Briefly, $2 \times 10^6$ cells were implanted in the mammary fat pad. Tumors were allowed to establish for 13 days, at which point tumor volume was determined using electronic caliper measurements using the formula: $L \times W^2/2$. Mice were allocated into treatment groups (n=10 per group) so that each cohort had equivalent mean tumor volume of 150 mm$^3$ prior to initiation of therapy. Animals were dosed with paclitaxel and/or anti-DLL4-VEGF DVD-Ig, at the dose and schedule in Table 32. Tumor volume was measured twice a week for the duration of the experiment. Additionally, bioluminescent images were acquired to monitor and track spontaneous metastasis of cancer cell to the lung and/or lymph nodes Results are shown in Table 32.

TABLE 32

Combination efficacy of anti-DLL4-VEGF DVD-Ig and paclitaxel in the MDA-MB-231-luc breast xenograft model

| Treatment | Dose Route, Regimen | % TGI[a] | TGD[b] | % % met incidence[c] |
|---|---|---|---|---|
| Paclitaxel | 25 mg/kg IP, q4dX3 | 78*** | 106*** | 40* |
| h1A11.1-SL-Av | 6.7 mg/kg IP, q7dX4 | 56*** | 85*** | 50* |
| h1A11.1-SL-Av + Paclitaxel | 6.7 mg/kg IP, q7dX4 + 25 mg/kg IP, q4dX3 | 92*** | 179*** | 0*** |

Table 32 key.
[a]% TGI = Percent tumor growth inhibition = 100 − (T/C × 100), where T = mean tumor volume of treatment group and C = mean tumor volume of treatment control group. Based on day 15 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$. P values (as indicated by asterisks) derived from Kaplan Meier log-rank comparison of treatment group vs. treatment control group.
[c]% metastasis incidence = Percent of animals with detectable signal in the lung and/or lymph nodes based on bioluminescent imaging. Treatment control group had 100%. Based on day 22 post size match measurements.
P values (as indicated by asterisks) are derived from Student's T test comparison of treatment group vs. treatment control group: *p < 0.05; p < 0.001; *p < 0.0001.

The effect of anti-DLL4-VEGF DVD-Igs in combination with chemotherapy on tumor growth was evaluated on SUM149PT human breast xenograft tumors in female SCID mice. Briefly, $1 \times 10^6$ cells were inoculated subcutaneously into the right hind flank. Tumors were allowed to establish for 28 days, at which point tumor volume was determined using electronic caliper measurements using the formula: $L \times W^2/2$.

Mice were allocated into treatment groups (n=9 per group) so that each cohort had equivalent mean tumor volume of 183 mm$^3$ prior to initiation of therapy. Animals were dosed with paclitaxel and/or anti-DLL4-VEGF DVD-Ig, at the dose and schedule in Table 33. Tumor volume was measured twice a week for the duration of the experiment. Results are shown in Table 33.

TABLE 33

Combination efficacy of anti-DLL4-VEGF DVD-Ig and paclitaxel in the SUM149PT breast xenograft model

| Treatment | Dose Route, Regimen | % TGI[a] | % TGD[b] |
|---|---|---|---|
| Paclitaxel | 25 mg/kg IP, [q4dX3]X4 | 60*** | 173*** |
| h1A11.1-SL-Av | 6.7 mg/kg IP, q7dX8 | 88*** | 282*** |
| h1A11.1-SL-Av + Paclitaxel | 6.7 mg/kg IP, q7dX8 + 25 mg/kg IP, [q4dX3]X4 | 93*** | 459*** |

Table 33 key.
[a]% TGI = Percent tumor growth inhibition = 100 − (T/C × 100), where T = mean tumor volume of treatment group and C = mean tumor volume of treatment control group. Based on day 22 post size match measurements. P values (as indicated by asterisks) are derived from Student's T test comparison of treatment group vs. treatment control group.
[b]% TGD = Percent tumor growth delay = (T − C)/C × 100, where T = median time to endpoint of treatment group and C = median time to endpoint of treatment control group. Based on an endpoint of 1000 mm$^3$.
P values (as indicated by asterisks) derived from Kaplan Meier log-rank comparison of treatment group vs. treatment control group: *p < 0.05; p < 0.001; *p < 0.0001.

The effect of anti-DLL4-VEGF DVD-Igs in combination with chemotherapy on tumor growth was evaluated on SUM149PT human breast xenograft tumors in female SCID mice. Briefly, 1×10$^6$ cells were inoculated subcutaneously into the right hind flank. Tumors were allowed to establish for 25 days, at which point tumor volume was determined using electronic caliper measurements using the formula: L×W$^2$/2. Mice were allocated into treatment groups (n=10 per group) so that each cohort had equivalent mean tumor volume of 228 mm$^3$ prior to initiation of therapy. Animals were dosed with paclitaxel, anti-VEGF mAb and/or anti-DLL4-VEGF DVD-Ig, at the dose and schedule in Table 34. Tumor volume was measured twice a week for the duration of the experiment. Results are shown in Table 34.

TABLE 34

Combination efficacy of anti-DLL4-VEGF DVD-Ig and paclitaxel in the SUM149PT breast xenograft model

| Treatment | Dose Route, Regimen | % TGI[a] |
|---|---|---|
| Paclitaxel | 25 mg/kg IP, [q4dX3]X4 | 50* |
| Anti-VEGF mAb | 5 mg/kg IP, q7dX8 | 54* |
| h1A11.1-SL-Av | 6.7 mg/kg IP, q7dX8 | 78** |
| Anti-VEGF mAb + Paclitaxel | 5 mg/kg IP, q7dX8 + 25 mg/kg IP, [q4dX3]X4 | 81** |
| h1A11.1-SL-Av + Paclitaxel | 6.7 mg/kg IP, q7dX8 + 25 mg/kg IP, [q4dX3]X4 | 87** |

Table 34 key.
[a]% TGI = Percent tumor growth inhibition = 100 − (T/C × 100), where T = mean tumor volume of treatment group and C = mean tumor volume of treatment control group. Based on day 18 post size match measurements.
P values (as indicated by asterisks) are derived from Student's T test comparison of treatment group vs. treatment control group: *p < 0.05; p < 0.001; *p < 0.0001.

The preceding examples are intended to illustrate and in no way limit the present disclosure. Other embodiments of the disclosed devices and methods will be apparent to those skilled in the art from consideration of the specification and practice of the devices and methods disclosed herein

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Ausubel et al. (eds.), CURRENT PROTOCOLS IN MOLECULAR BIOLOGY, John Wiley & Sons, NY (1993);

Ausubel, F. M. et al. eds., SHORT PROTOCOLS IN MOLECULAR BIOLOGY (4th Ed. 1999) John Wiley & Sons, NY. (ISBN 0-471-32938-X);

CONTROLLED DRUG BIOAVAILABILITY, DRUG PRODUCT DESIGN AND PERFORMANCE, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, N.Y., (1999);

Goodson, in MEDICAL APPLICATIONS OF CONTROLLED RELEASE, vol. 2, pp. 115-138 (1984);

Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, NY (1990);

Lu and Weiner eds., CLONING AND EXPRESSION VECTORS FOR GENE FUNCTION ANALYSIS (2001) BioTechniques Press. Westborough, Mass. 298 pp. (ISBN 1-881299-21-X).

MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).

SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

We claim:

1. A binding protein comprising first and second polypeptide chains, each independently comprising VD1-(X1)n-VD2-C-(X2)n, wherein VD1 is a first variable domain;

VD2 is a second variable domain;

C is a constant domain;

X1 is a linker;

X2 is an Fc region;

n is 0 or 1, wherein the VD1 domains on the first and second polypeptide chains form a first functional target binding site and the VD2 domains on the first and second polypeptide chains form a second functional target binding site, and wherein the binding protein is capable of binding DLL4 and VEGF, wherein the first polypeptide chain of the binding protein comprises SEQ ID NO: 56 and the second polypeptide chain of the binding protein comprises SEQ ID NO: 64.

2. The binding protein of claim 1, wherein the binding protein comprises a first polypeptide chain comprising a first VD1-(X1)n-VD2-C-(X2)n, wherein VD1 is a first heavy chain variable domain;

VD2 is a second heavy chain variable domain;

C is a heavy chain constant domain;

X1 is a linker;

X2 is an Fc region;

n is 0 or 1, and wherein the binding protein comprises a second polypeptide chain comprising a second VD1-(X1)n-VD2-C-(X2)n, wherein VD1 is a first light chain variable domain;

VD2 is a second light chain variable domain;

C is a light chain constant domain;

X1 is a linker;

n is 0 or 1 for (X1)n;

n is 0 for (X2)n, wherein the VD1 domains on the first and second polypeptide chains form a first functional target binding site and the VD2 domains on the first and second polypeptide chains form a second functional target binding site.

3. The binding protein of claim 1, wherein the binding protein comprises two first and two second polypeptide chains and four functional target binding sites.

4. The binding protein of claim 1, wherein the binding protein is capable of binding:

(a) VEGF with a dissociation constant ($K_D$) of at most about $7.40 \times 10^{-9}$ M, as measured by surface plasmon resonance; and/or (b) DLL4 with a dissociation constant ($K_D$) of at most about $3.40 \times 10^{-8}$ M or $5.00 \times 10^{-8}$ M, as measured by surface plasmon resonance.

5. The binding protein of claim 1, wherein the Fc region of the binding protein is an Fc region from an IgG1, IgG2, IgG3, IgG4, IgA, IgM, IgE, or IgD, or a variant thereof.

6. The binding protein of claim 1, wherein the Fc region of the binding protein is a variant sequence Fc region.

7. The binding protein of claim 1, wherein the binding protein comprises the constant region sequences from SEQ ID NO: 73 and/or SEQ ID NO: 74.

8. The binding protein of claim 1, wherein the first and second polypeptide chains of the binding protein comprise SEQ ID NOs: 74 and 73.

9. The binding protein of claim 8, wherein the binding protein is capable of:
  (a) binding to VEGF with a dissociation constant ($K_D$) of at most about $7.0 \times 10^{-10}$ M, as measured by surface plasmon resonance, and/or blocking VEGF activity with an IC50 of at most about 3.8 nM, as measured in a VEGFR1 Competition ELISA; and/or
  (b) binding to DLL4 with a dissociation constant ($K_D$) of at most about $1.0 \times 10^{-8}$ M, as measured by surface plasmon resonance, and/or blocking DLL4 activity with an IC50 of at most about 1.09 nM, as measured in a Notch Competition ELISA.

10. A composition comprising the binding protein of claim 1 and at least one additional agent.

11. The composition of claim 10, wherein the at least one additional agent comprises one or more of a cytotoxic agent, a chemotherapeutic agent, an anti-angiogenic agent, an anti-CTLA4 antibody, a calcium channel blocker, an ACE inhibitor, FOLFIRI, paclitaxel, carboplatin, doxil, topotecan, and cisplatin.

* * * * *